United States Patent
Bergstrom et al.

(10) Patent No.: US 7,642,251 B2
(45) Date of Patent: Jan. 5, 2010

(54) COMPOUNDS FOR THE TREATMENT OF HEPATITIS C

(75) Inventors: Carl P. Bergstrom, Madison, CT (US); Scott W. Martin, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/184,791

(22) Filed: Aug. 1, 2008

(65) Prior Publication Data

US 2009/0042860 A1    Feb. 12, 2009

Related U.S. Application Data

(60) Provisional application No. 60/954,813, filed on Aug. 9, 2007.

(51) Int. Cl.
*A61P 31/00* (2006.01)
*A61K 31/55* (2006.01)
*C07D 223/14* (2006.01)

(52) U.S. Cl. .................. 514/214.01; 540/576
(58) Field of Classification Search ............ 514/214.01; 540/576
See application file for complete search history.

(56) References Cited

U.S. PATENT DOCUMENTS

| 7,153,848 | B2 | 12/2006 | Hudyma et al. |
| 7,399,758 | B2 | 7/2008 | Meanwell et al. |
| 2007/0078122 | A1 | 4/2007 | Bergstrom et al. |
| 2007/0185083 | A1 | 8/2007 | Bergstrom et al. |
| 2007/0270405 | A1 | 11/2007 | Bender et al. |
| 2007/0270406 | A1 | 11/2007 | Gentles et al. |
| 2007/0275930 | A1 | 11/2007 | Gentles et al. |
| 2007/0275947 | A1 | 11/2007 | Bergstrom |
| 2007/0287694 | A1 | 12/2007 | Yeung et al. |
| 2008/0171015 | A1 | 7/2008 | Bender et al. |
| 2008/0206191 | A1 | 8/2008 | Nickel et al. |
| 2008/0226590 | A1 | 9/2008 | Bender et al. |
| 2008/0226591 | A1 | 9/2008 | Gentles et al. |
| 2008/0226592 | A1 | 9/2008 | Yeung et al. |
| 2008/0226593 | A1 | 9/2008 | Hewawasam et al. |
| 2008/0227769 | A1 | 9/2008 | Gentles et al. |

FOREIGN PATENT DOCUMENTS

| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/129119 | 11/2007 |

OTHER PUBLICATIONS

U.S. Appl. No. 60/894,881, filed Mar. 14, 2007, Yeung et al.
U.S. Appl. No. 60/989,472, filed Nov. 21, 2007, Bender et al.
U.S. Appl. No. 60/989,524, filed Nov. 21, 2007, Hewawasam et al.
U.S. Appl. No. 61/039,973, filed Mar. 27, 2008, Yang et al.
U.S. Appl. No. 61/039,976, filed Mar. 27, 2008, Yeung et al.
U.S. Appl. No. 12/169,874, filed Jul. 9, 2008, Schmitz et al.
U.S. Appl. No. 12/180,994, filed Jul. 28, 2008, Martin et al.

*Primary Examiner*—Brenda L Coleman
(74) *Attorney, Agent, or Firm*—James Epperson

(57) ABSTRACT

The invention encompasses compounds of formula I as well as compositions and methods of using the compounds. The compounds have activity against hepatitis C virus (HCV) and are useful in treating those infected with HCV.

16 Claims, No Drawings

COMPOUNDS FOR THE TREATMENT OF HEPATITIS C

CROSS-REFERENCE TO RELATED APPLICATIONS

This application claims the benefit of U.S. Provisional Application Ser. No. 60/954,813 filed Aug. 9, 2007.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

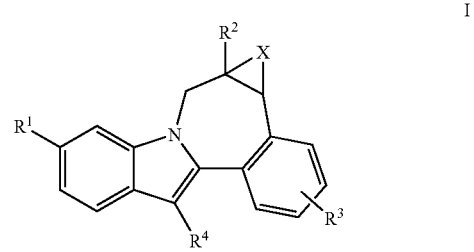

where:
$R^1$ is $CO_2R^5$ or $CONR^6R^7$;
$R^2$ is pyridinyl, pyrazinyl, pyrimidinyl, or pyridazinyl, and is substituted with 0-1 substituents selected from the group consisting of $(R^5)_2N$, $R^{12}$, $COR^{13}$, and $SO_2R^{14}$;
or $R^2$ is phenyl and is substituted with 0-2 substituents selected from halo, alkyl, alkoxy, and haloalkoxy and is substituted with 0-1 substituents selected from the group consisting of $(R^5)_2N$, $((R^5)_2N)alkyl(R^5)N$, $(R^{12})alkyl(R^5)N$, $alkylCON(R^5)$, $cycloalkylCON(R^5)$, (methyl)oxadiazolyl, $((R^5)_2N)alkoxy$, $(R^{12})alkoxy$, $R^{12}$, $((R^5)_2N)alkyl$, $(R^{12})alkyl$, $COR^{13}$, $(alkylSO_2)alkyl$, and $SO_2R^{14}$;
or $R^2$ is indolyl, indazolyl, benzimidazolyl, benzotriazolyl, pyrrolopyridinyl, benzoxazolyl, benzothiazolyl, and is substituted with 0-2 substituents selected from halo, alkyl, haloalkyl, nitro, cyano, alkoxy, and haloalkoxy;
or $R^2$ is benzodioxolyl or dihydrobenzodioxinyl, and is substituted with 0-2 substituents selected from halo and alkyl;
$R^3$ is hydrogen, halo, alkyl, alkenyl, hydroxy, benzyloxy, or alkoxy;
$R^4$ is cycloalkyl;
$R^5$ is hydrogen or alkyl;
$R^6$ is hydrogen, alkyl, $alkylSO_2$, $cycloalkylSO_2$, $haloalkylSO_2$, $(R^9)(R^{10})NSO_2$, or $(R^{11})SO_2$;
$R^7$ is hydrogen or alkyl;
$R^8$ is hydrogen, alkyl, cycloalkyl, (cycloalkyl)alkyl, alkylcarbonyl, cycloalkylcarbonyl, haloalkylcarbonyl, alkoxycarbonyl, $alkylSO_2$, $cycloalkylSO_2$, $haloalkylSO_2$, aminocarbonyl, (alkylamino)carbonyl, (dialkylamino)carbonyl, benzyl, benzyloxycarbonyl, or pyridinyl;
$R^9$ is hydrogen or alkyl;
$R^{10}$ is hydrogen or alkyl;
$R^{11}$ is azetidinyl, pyrrolidinyl, piperidinyl, piperazinyl, N-alkylpiperazinyl, morpholinyl, thiomorpholinyl, homopiperidinyl, or homomorpholinyl;
$R^{12}$ is azetidinyl, pyrrolidinyl, piperidinyl, piperazinyl, morpholinyl, thiomorpholinyl, homopiperidinyl, or homomorpholinyl, and is substituted with 0-3 substituents selected from oxo and alkyl;
$R^{13}$ is hydroxy, alkoxy, amino, alkylamino, dialkylamino, azetidinyl, pyrrolidinyl, piperidinyl, hydroxypiperidinyl, piperazinyl, N-alkylpiperazinyl, morpholinyl, thiomorpholinyl, homopiperidinyl, homomorpholinyl,

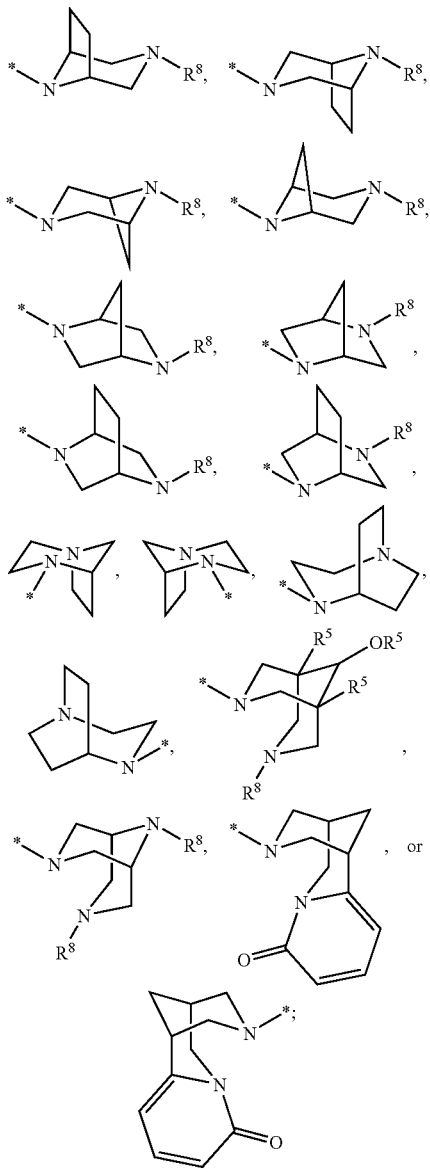

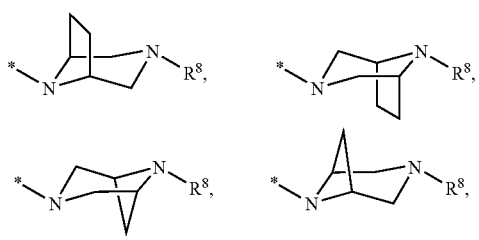

$R^{14}$ is hydroxy, alkoxy, $(R^5)_2N$, $((R^5)_2N)$alkyl, $((R^5)_2N)$alkyl$(R^5)N$, $(R^{12})$alkyl, $(R^{12})$alkyl$(R^5)N$, azetidinyl, pyrrolidinyl, piperidinyl, hydroxypiperidinyl, piperazinyl, N-alkylpiperazinyl, morpholinyl, thiomorpholinyl, homopiperidinyl, homomorpholinyl,

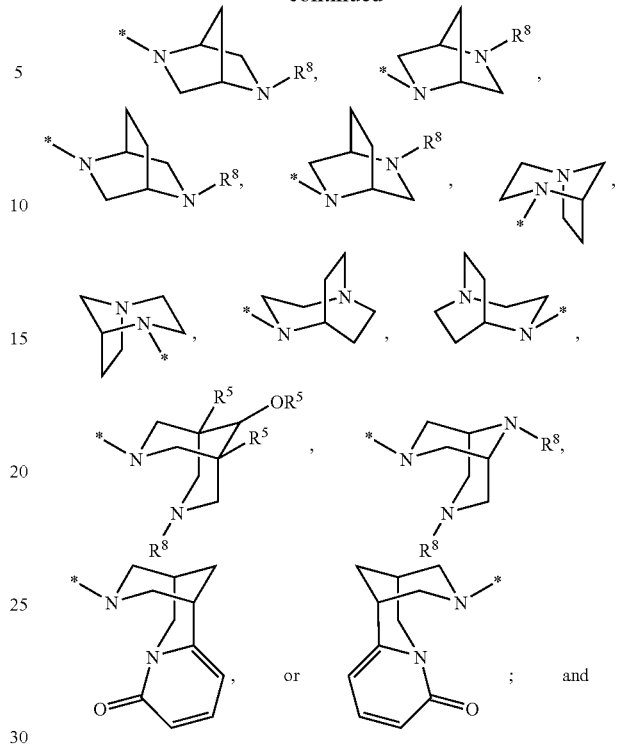

X is methylene, a bond, or absent;
or a pharmaceutically acceptable salt thereof.

Another aspect of the invention is a compound of formula I where:

$R^1$ is $CO_2R^5$ or $CONR^6R^7$;

$R^2$ is pyridinyl, pyrazinyl, pyrimidinyl, or pyradazinyl, and is substituted with 0-1 substituents selected from the group consisting of amino, alkylamino, dialkylamino, $R^{12}$, $COR^{13}$, and $SO_2R^{14}$;

or $R^2$ is phenyl and is substituted with 0-2 substituents selected from halo, alkyl, and alkoxy and is substituted with 0-1 substituents selected from the group consisting of amino, alkylamino, dialkylamino, $R^{12}$, $COR^{13}$, and $SO_2R^{14}$;

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkylSO$_2$, cycloalkylSO$_2$, haloalkylSO$_2$, $(R^9)(R^{10})$NSO$_2$, or $(R^{11})$SO$_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, piperazinyl, N-alkylpiperazinyl, morpholinyl, thiomorpholinyl, homopiperidinyl, or homomorpholinyl;

$R^{12}$ is azetidinyl, pyrrolidinyl, piperidinyl, piperazinyl, morpholinyl, thiomorpholinyl, homopiperidinyl, or homomorpholinyl, and is substituted with 0-3 substituents selected from oxo and alkyl;

$R^{13}$ is hydroxy, alkoxy, amino, alkylamino, dialkylamino, azetidinyl, pyrrolidinyl, piperidinyl, hydroxypiperidinyl, piperazinyl, N-alkylpiperazinyl, morpholinyl, thiomorpholinyl, homopiperidinyl, homomorpholinyl,

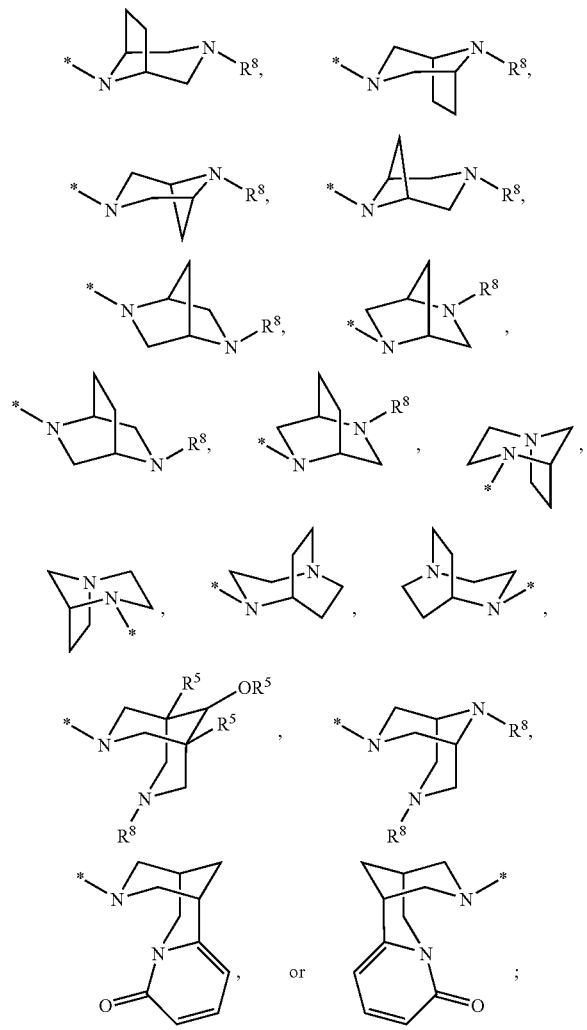

$R^{14}$ is hydroxy, alkoxy, amino, alkylamino, dialkylamino, azetidinyl, pyrrolidinyl, piperidinyl, hydroxypiperidinyl, piperazinyl, N-alkylpiperazinyl, morpholinyl, thiomorpholinyl, homopiperidinyl, homomorpholinyl,

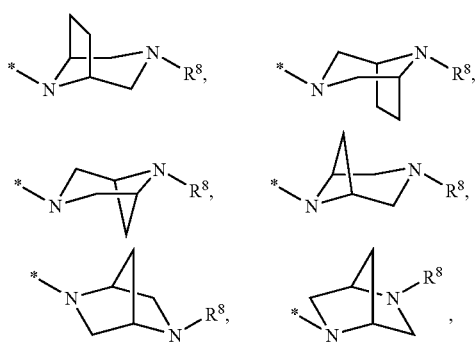

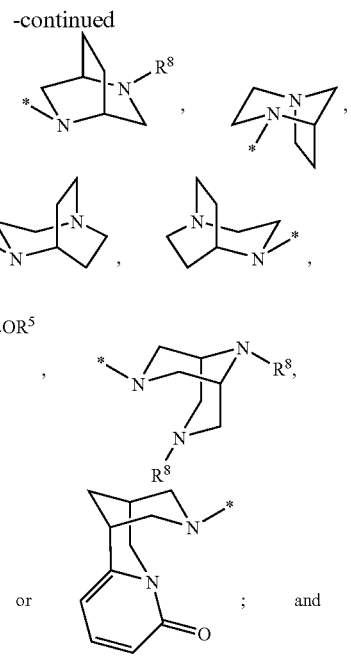

X is methylene, a bond, or absent;
or a pharmaceutically acceptable salt thereof.

Another aspect of the invention is a compound of formula I where $R^1$ is $CONR^6R^7$; $R^6$ is alkylSO$_2$, cycloalkylSO$_2$, haloalkylSO$_2$, $(R^9)_2NSO_2$, or $(R^{10})SO_2$; and $R^7$ hydrogen.

Another aspect of the invention is a compound of formula I where $R^2$ is pyridinyl, pyrazinyl, pyrimidinyl, or pyradazinyl, and is substituted with 0-1 substituents selected from the group consisting of amino, alkylamino, dialkylamino, $R^{12}$, $COR^{13}$, and $SO_2R^{14}$.

Another aspect of the invention is a compound of formula I where $R^2$ is phenyl and is substituted with 0-2 substituents selected from halo, alkyl, alkoxy, and haloalkoxy and is substituted with 0-1 substituents selected from the group consisting of $(R^5)_2N$, $((R^5)_2N)$alkyl$(R^5)N$, $(R^{12})$alkyl$(R^5)N$, alkyl-$CON(R^5)$, cycloalkylCON$(R^5)$, (methyl)oxadiazolyl, $((R^5)_2N)$alkoxy, $(R^{12})$alkoxy, $R^{12}$, $((R^5)_2N)$alkyl, $(R^{12})$alkyl, $COR^{13}$, (alkylSO$_2$)alkyl, and $SO_2R^{14}$;

Another aspect of the invention is a compound of formula I where $R^2$ is phenyl and is substituted with 0-2 substituents selected from halo, alkyl, and alkoxy and is substituted with 0-1 substituents selected from the group consisting of amino, alkylamino, dialkylamino, $R^{12}$, $COR^{13}$, and $SO_2R^{14}$.

Another aspect of the invention is a compound of formula I where $R^2$ is indolyl, indazolyl, benzimidazolyl, benzotriazolyl, pyrrolopyridinyl, benzoxazolyl, benzothiazolyl, and is substituted with 0-2 substituents selected from halo, alkyl, haloalkyl, nitro, cyano, alkoxy, and haloalkoxy;

Another aspect of the invention is a compound of formula I where $R^2$ is benzodioxolyl or dihydrobenzodioxinyl, and is substituted with 0-2 substituents selected from halo and alkyl;

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is alkylSO$_2$, $(R^9)(R^{10})NSO_2$ or $(R^{11})SO_2$.

Another aspect of the invention is a compound of formula I where $R^6$ is $(R^9)(R^{10})NSO_2$ or $(R^{11})SO_2$.

Another aspect of the invention is a compound of formula I where X is methylene.

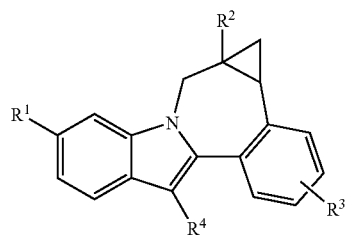

Another aspect of the invention is a compound of formula I where X is a bond.

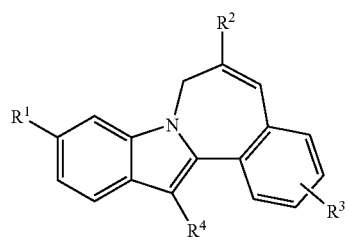

Another aspect of the invention is a compound of formula I where X is absent.

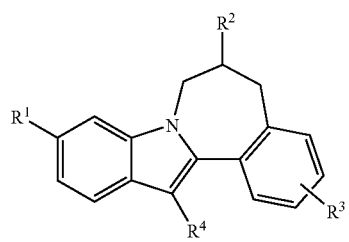

Another aspect of the invention is a compound of formula I according to the following stereochemistry.

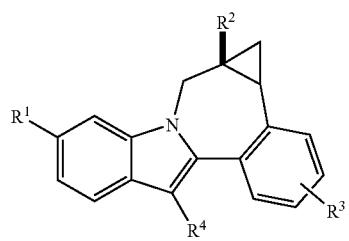

Another aspect of the invention is a compound of formula I according to the following stereochemistry.

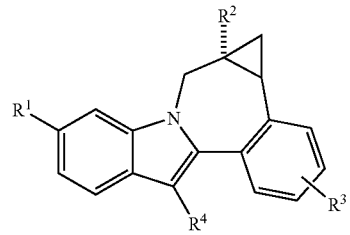

Another aspect of the invention is a compound of formula I according to the following stereochemistry.

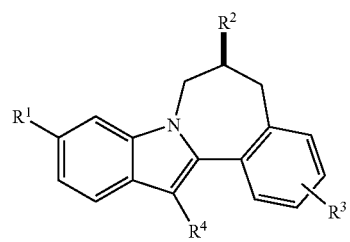

Another aspect of the invention is a compound of formula I according to the following stereochemistry.

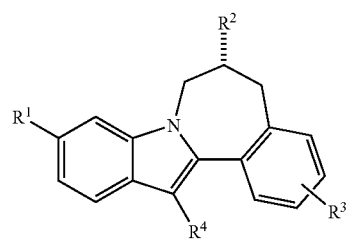

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and X, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

Benzodioxolyl means the moiety

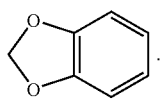

Dihydrobenzodioxinyl means the moiety

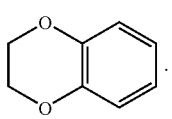

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compound below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art.

Synthetic Methods

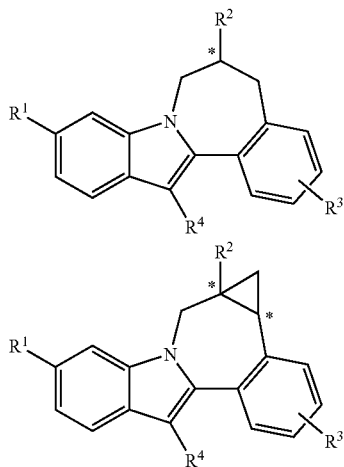

The compounds may be made by methods known in the art including those described below. Some reagents and intermediates are known in the art. Other reagents and intermediates can be made by methods known in the art using available materials. The variables (e.g. numbered "R" substituents) used to describe the synthesis of the compounds are intended only to illustrate how to make the compounds and are not to be confused with variables used in the claims or in other sections of the specification. Abbreviations used within the schemes generally follow conventions used in the art.

Scheme 1.

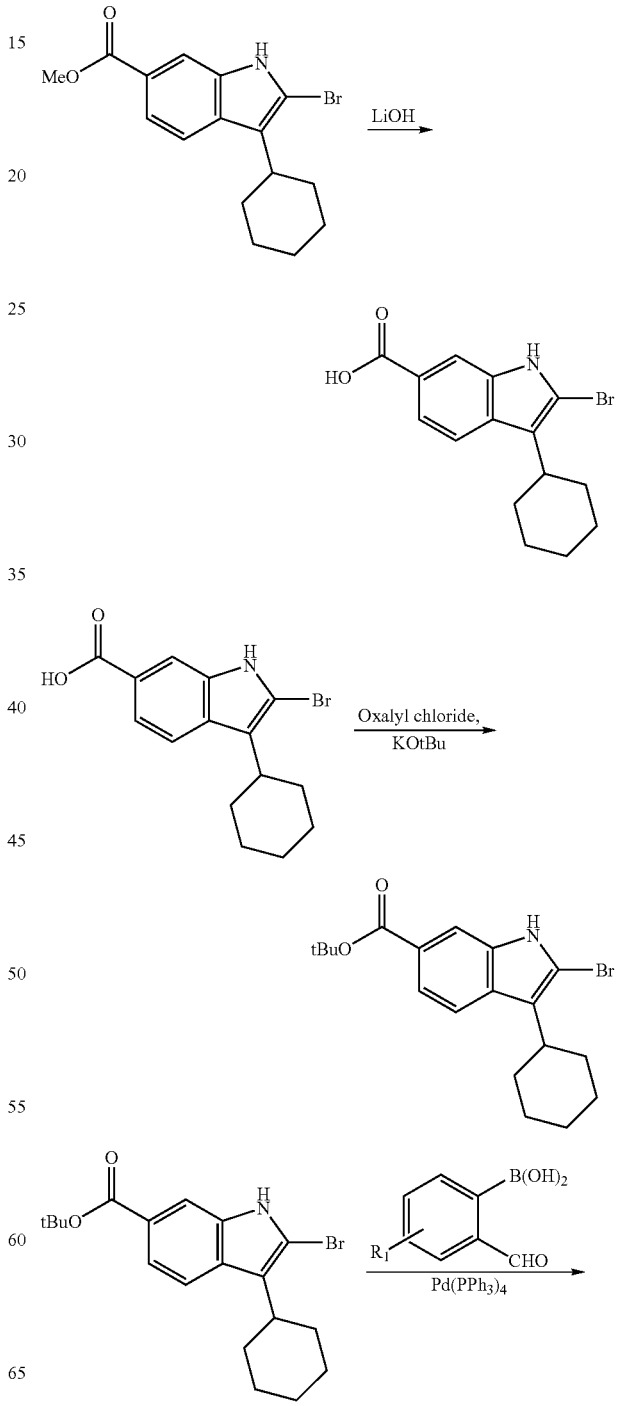

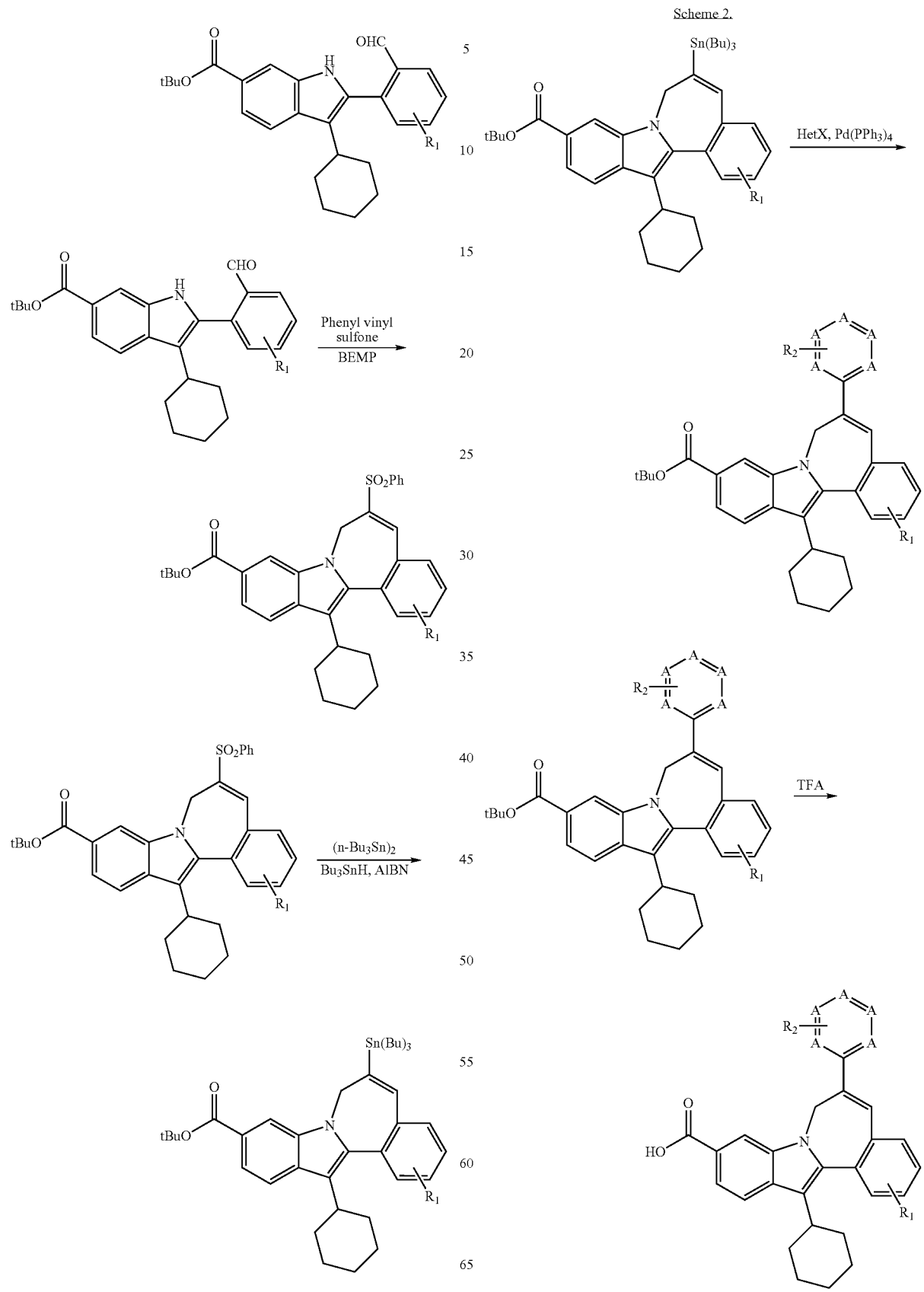

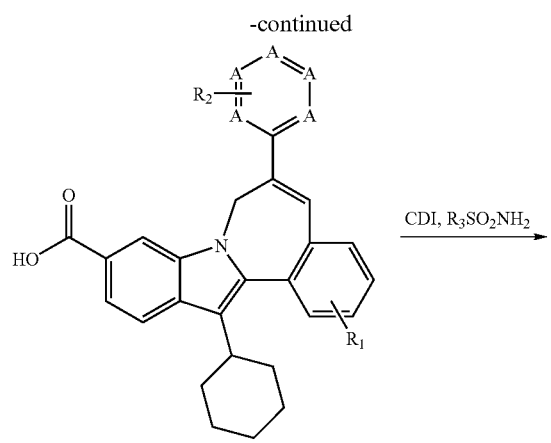
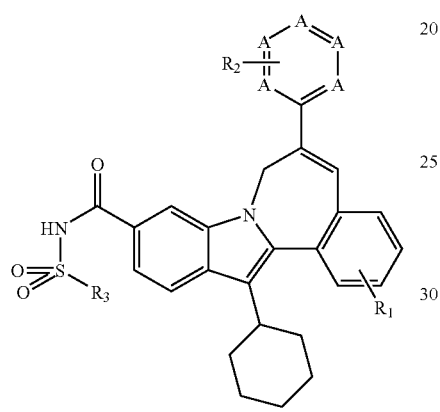
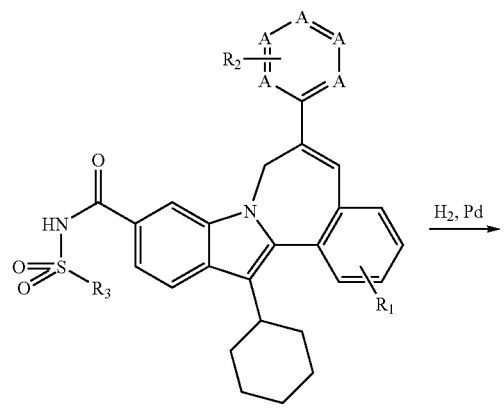
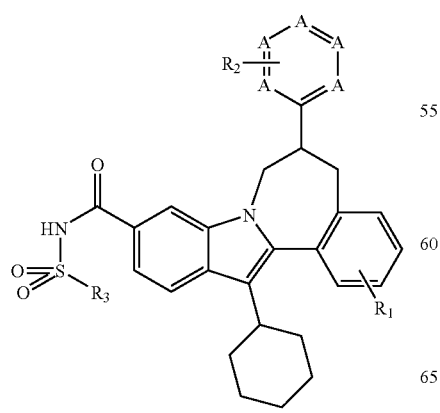
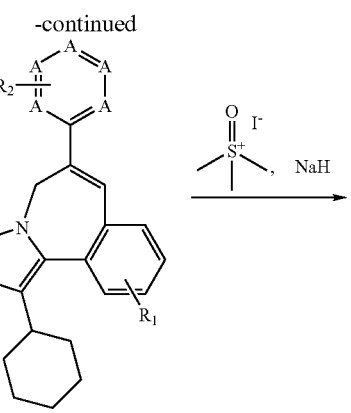
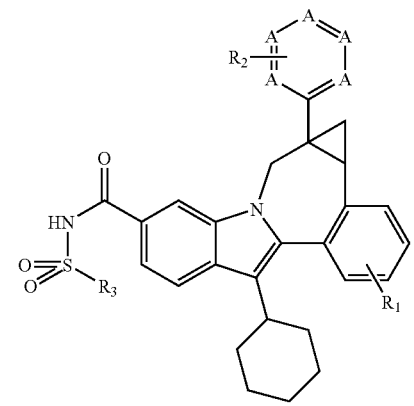
Scheme 3.
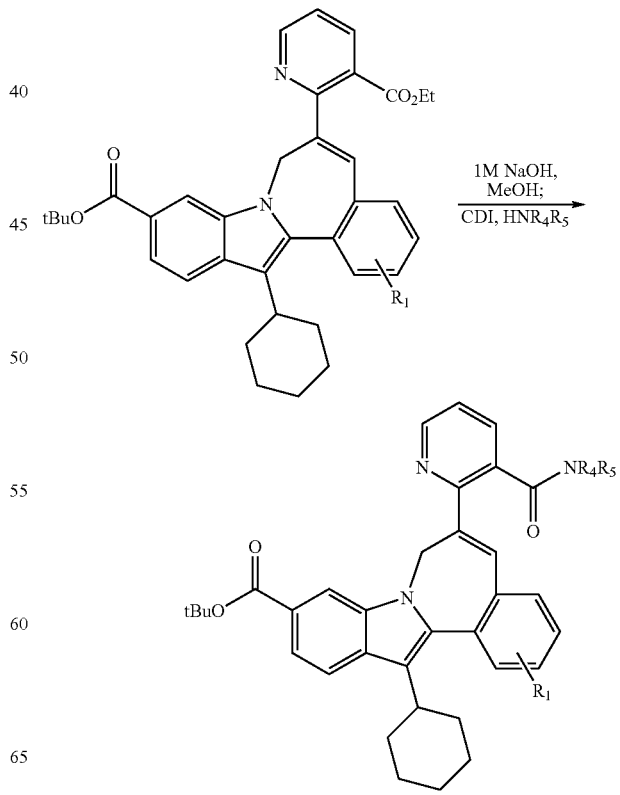

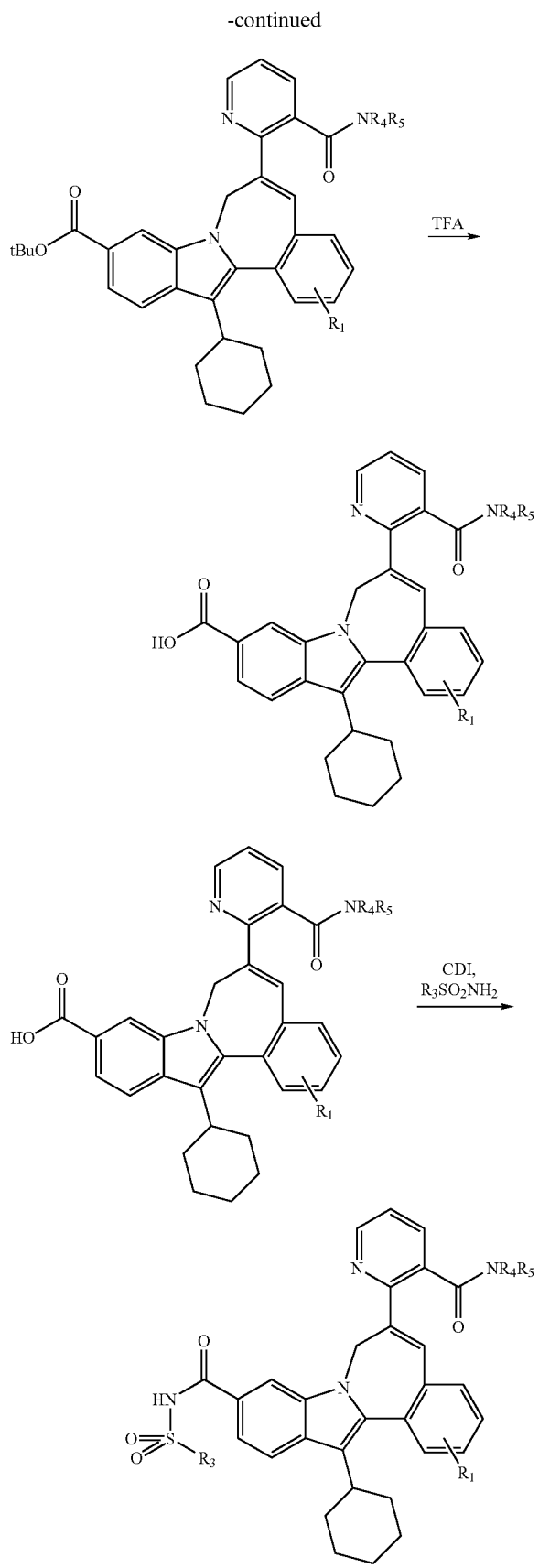

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete™ protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 μM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Structure | $IC_{50}$(uM) | $EC_{50}$(uM) |
|---|---|---|
| 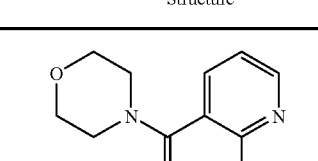 | B | B |

TABLE 1-continued
| Structure | IC$_{50}$(uM) | EC$_{50}$(uM) |
| --- | --- | --- |
| 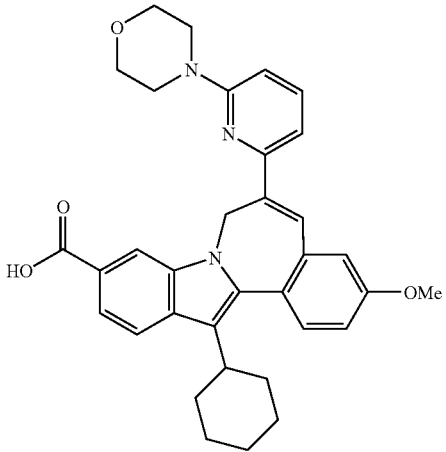 | A | A |
| 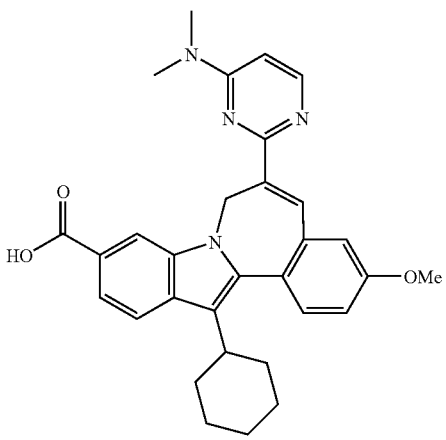 | A | A |
| 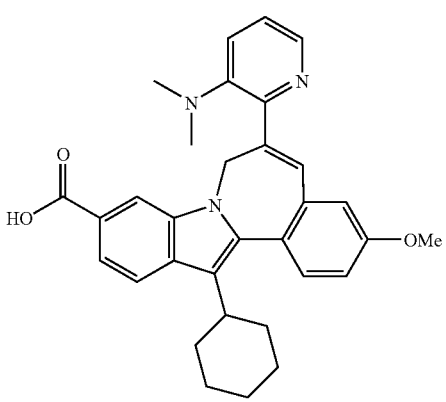 | B | B |

TABLE 1-continued
| Structure | IC$_{50}$(uM) | EC$_{50}$(uM) |
|---|---|---|
| 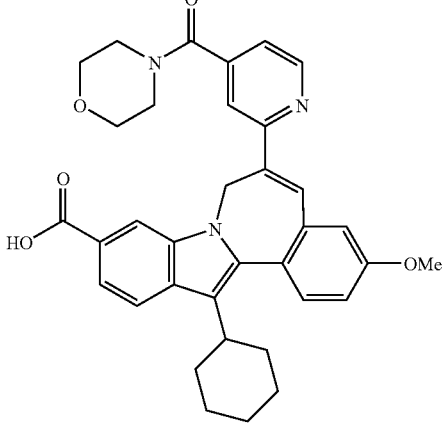 | A | A |
| 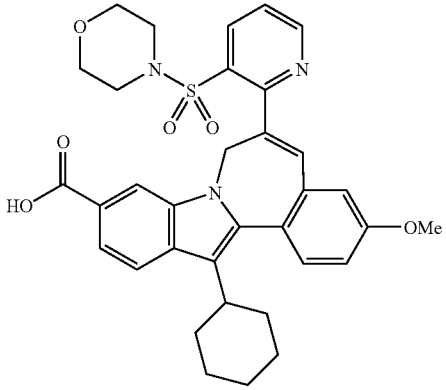 | B | B |
| 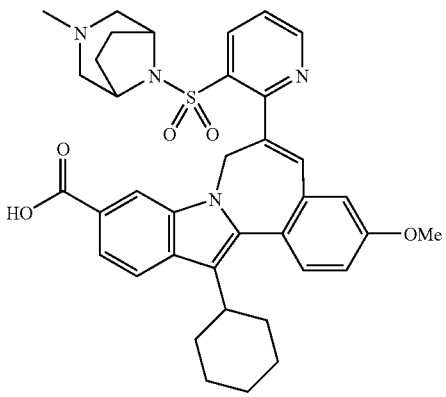 | A | B |

TABLE 1-continued
| Structure | IC$_{50}$(uM) | EC$_{50}$(uM) |
|---|---|---|
| 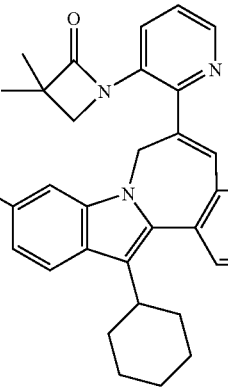 | B | B |
| 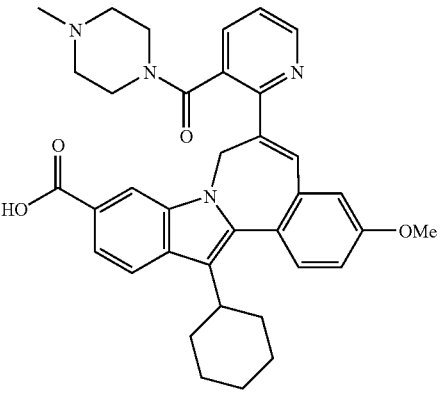 | B | B |
| 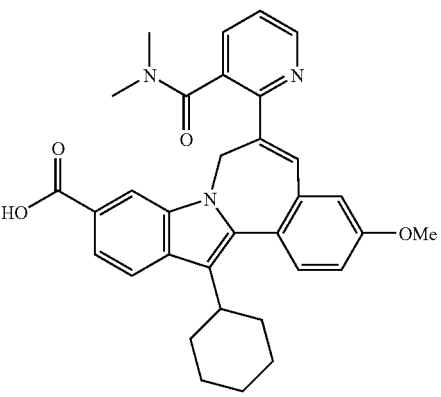 | B | B |
| 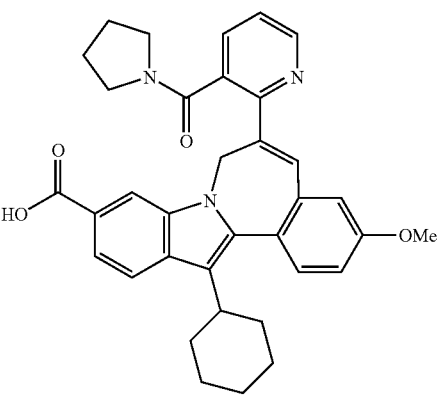 | B | B |

TABLE 1-continued
| Structure | IC$_{50}$(uM) | EC$_{50}$(uM) |
|---|---|---|
| 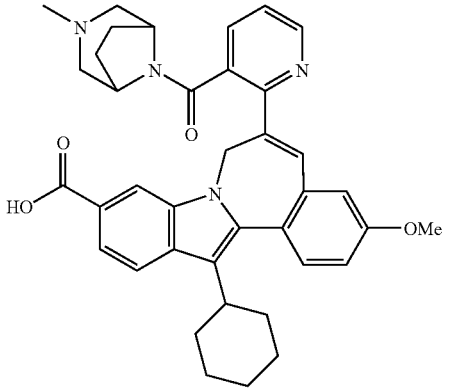 | B | B |
| 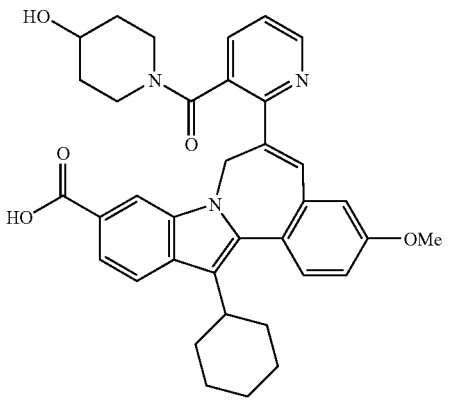 | B | B |
| 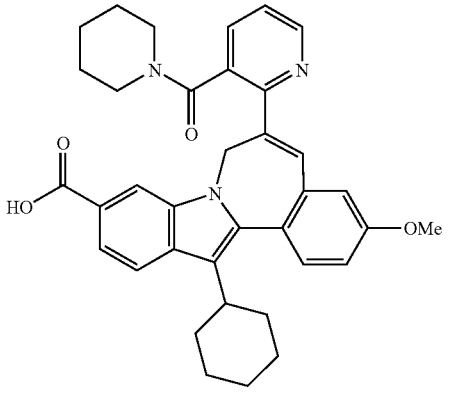 | B | B |
| 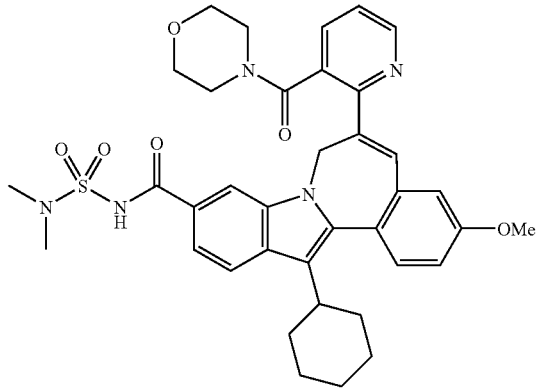 | B | B |

TABLE 1-continued
| Structure | IC$_{50}$(uM) | EC$_{50}$(uM) |
|---|---|---|
| 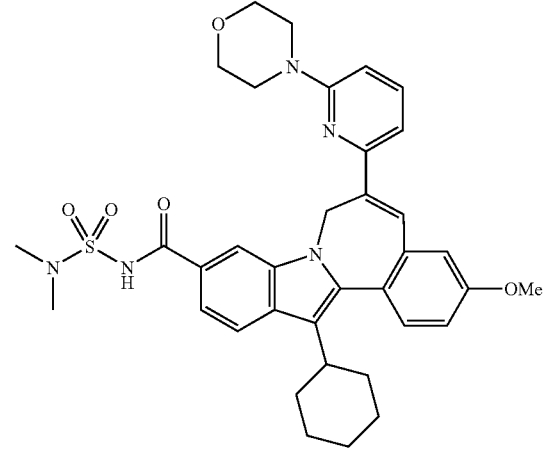 | B | B |
| 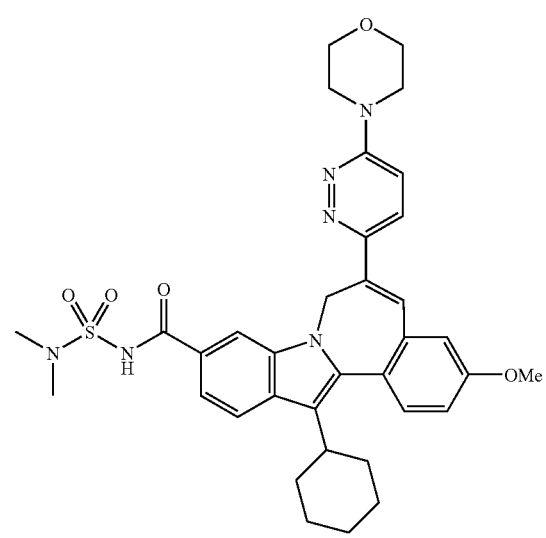 | B | A |
| 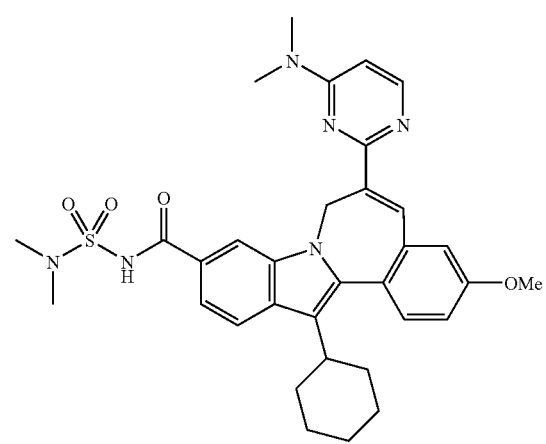 | B | A |

TABLE 1-continued

| Structure | IC$_{50}$(uM) | EC$_{50}$(uM) |
|---|---|---|
| | B | B |
| | B | B |
| | B | B |

TABLE 1-continued

| Structure | IC₅₀(uM) | EC₅₀(uM) |
|---|---|---|
| (structure) | B | B |
| (structure) | B | B |
| (structure) | B | B |
| (structure) | B | B |

TABLE 1-continued
| Structure | IC$_{50}$(uM) | EC$_{50}$(uM) |
|---|---|---|
| 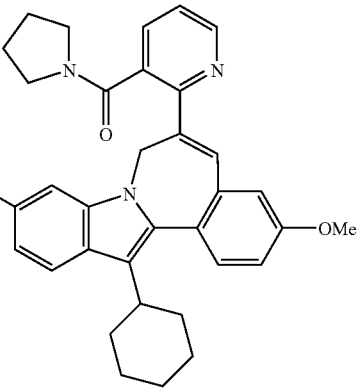 | B | B |
| 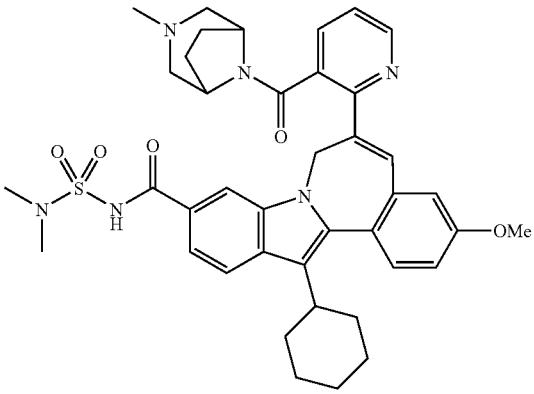 | B | B |
| 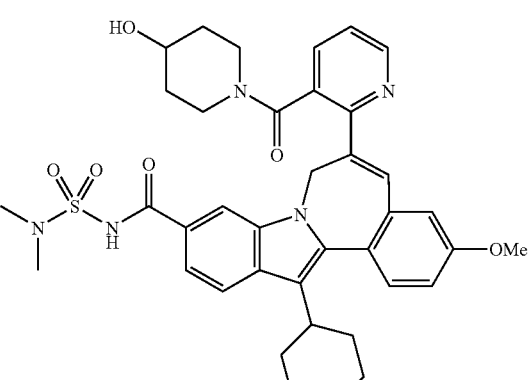 | B | B |
| 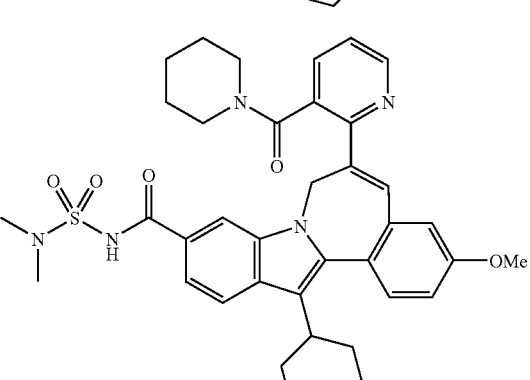 | B | B |

TABLE 1-continued
| Structure | IC$_{50}$(uM) | EC$_{50}$(uM) |
|---|---|---|
| 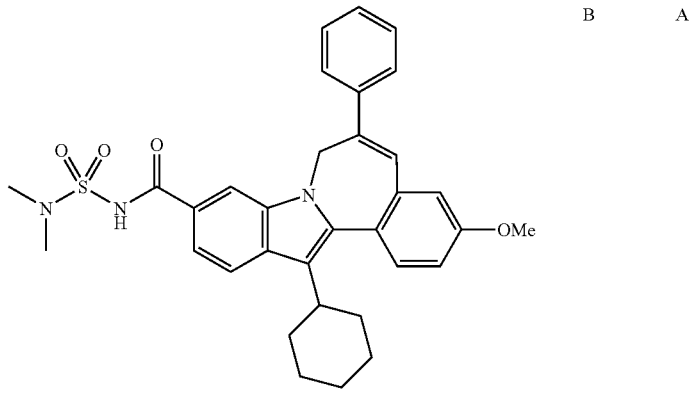 | B | A |
| 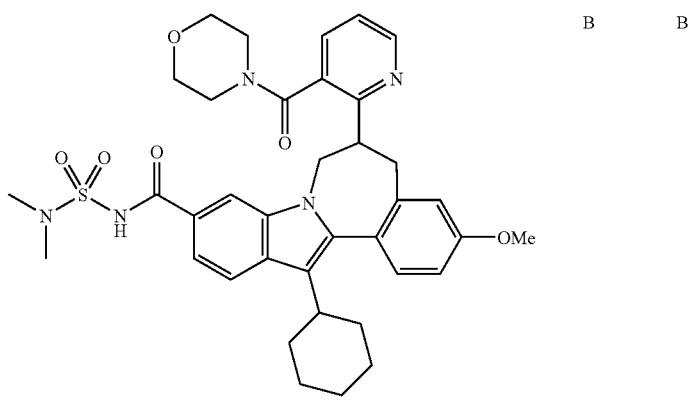 | B | B |
| 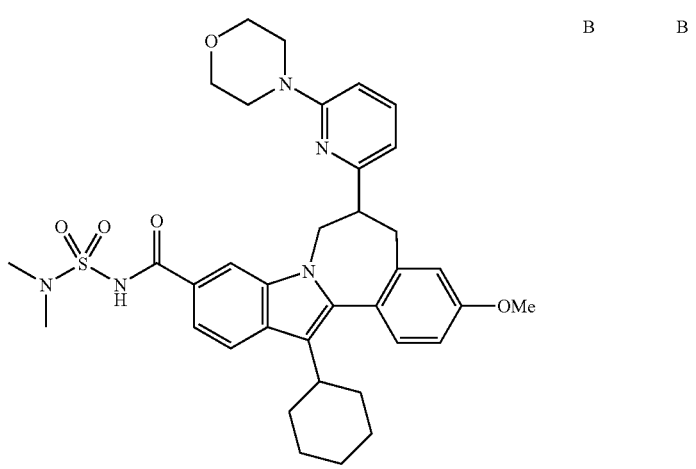 | B | B |

TABLE 1-continued
| Structure | IC$_{50}$(uM) | EC$_{50}$(uM) |
|---|---|---|
| 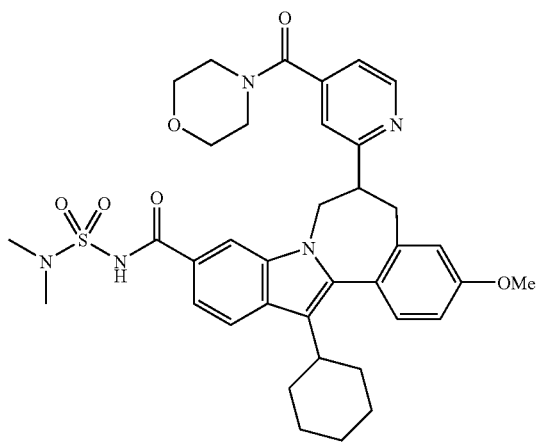 | B | B |
| 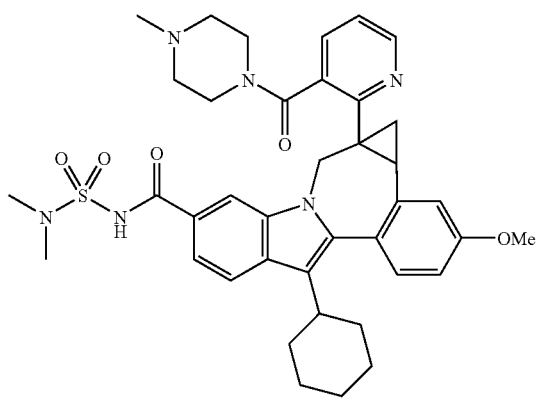 | B | B |
| 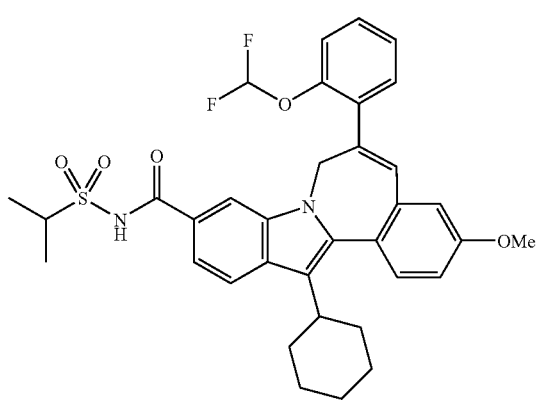 | B | A |

TABLE 1-continued

| Structure | IC$_{50}$(uM) | EC$_{50}$(uM) |
|---|---|---|
| | B | A |
| | B | B |
| | B | A |

TABLE 1-continued
| Structure | IC$_{50}$(uM) | EC$_{50}$(uM) |
|---|---|---|
| 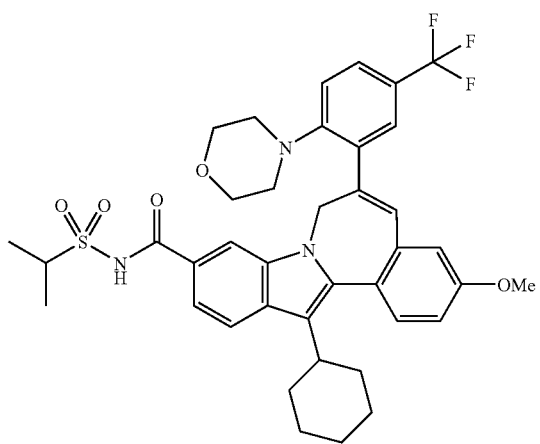 | A | A |
| 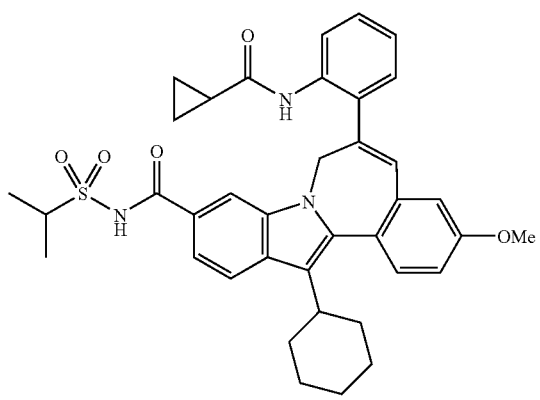 | B | B |
| 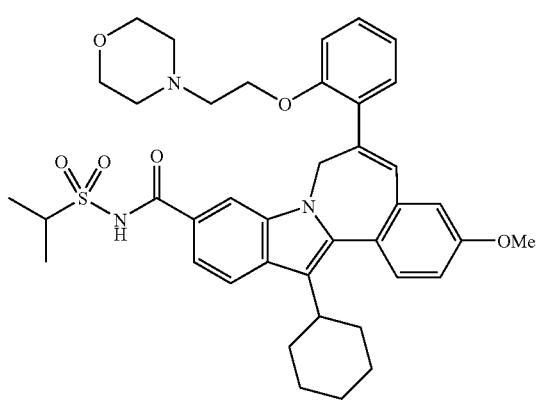 | B | B |

TABLE 1-continued

| Structure | IC$_{50}$(uM) | EC$_{50}$(uM) |
|---|---|---|
| | B | B |
| | B | B |
| | B | A |
| | B | A |

TABLE 1-continued
| Structure | IC$_{50}$(uM) | EC$_{50}$(uM) |
| --- | --- | --- |
| 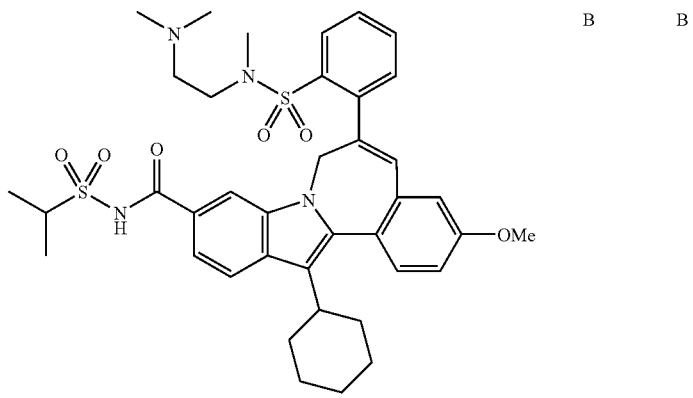 | B | B |
| 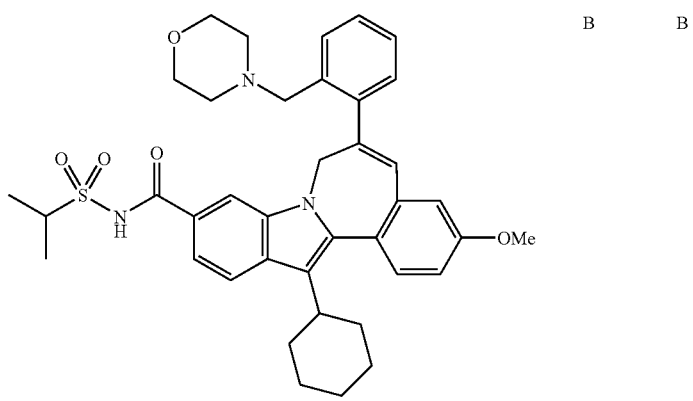 | B | B |
| 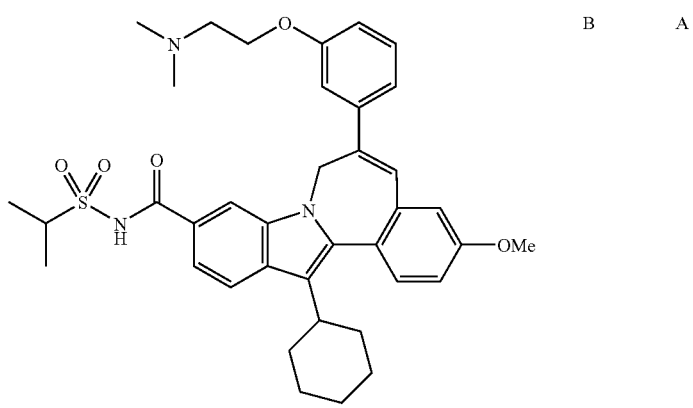 | B | A |

TABLE 1-continued
| Structure | IC$_{50}$(uM) | EC$_{50}$(uM) |
|---|---|---|
| 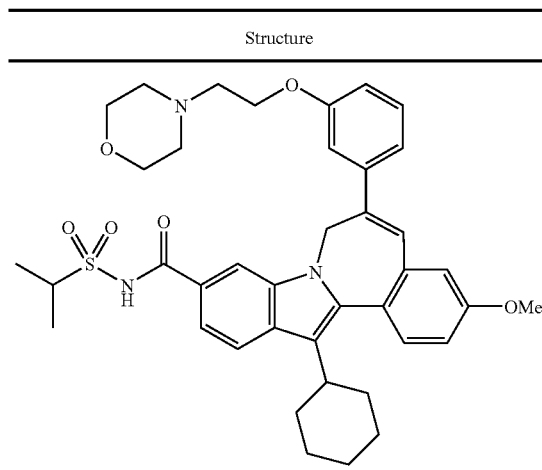 | B | A |
| 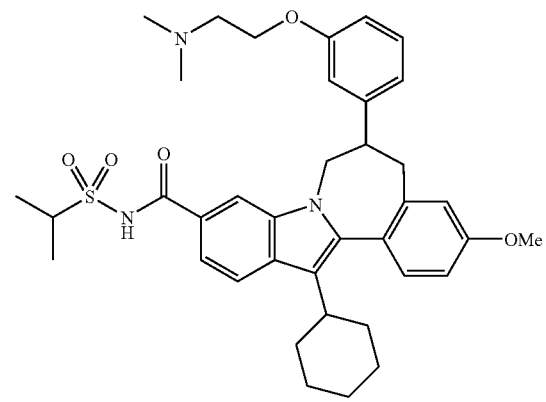 | B | B |
| 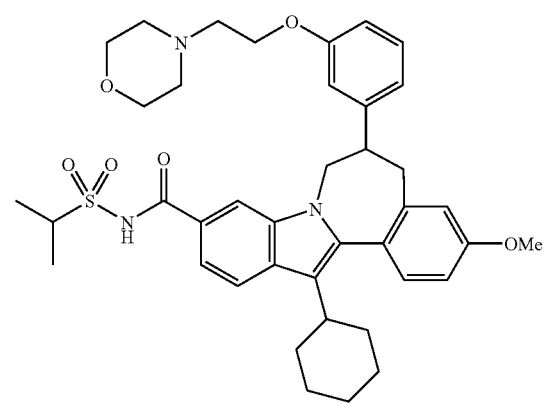 | B | B |

TABLE 1-continued

| Structure | IC$_{50}$(uM) | EC$_{50}$(uM) |
|---|---|---|
| | B | A |
| | B | A |
| | B | A |
| | B | B |

TABLE 1-continued
| Structure | IC$_{50}$(uM) | EC$_{50}$(uM) |
|---|---|---|
| 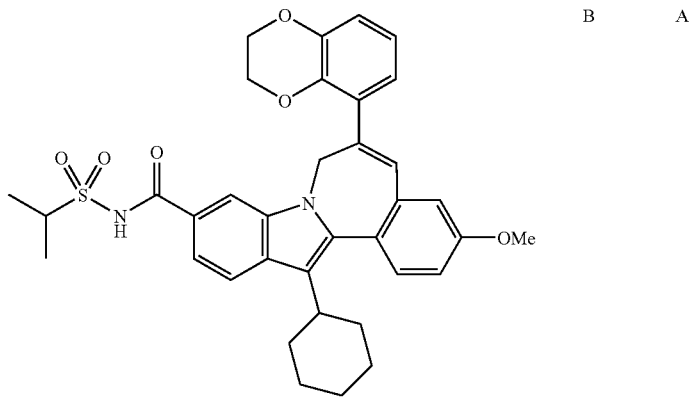 | B | A |
| 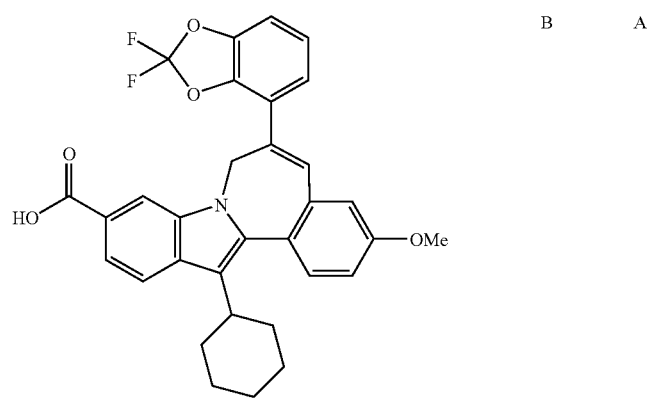 | B | A |
| 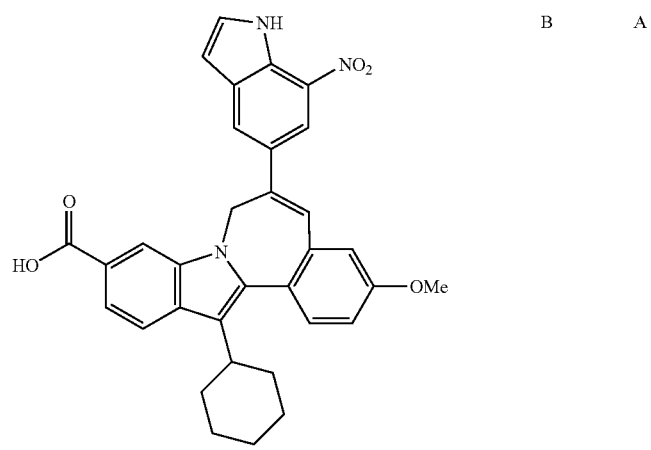 | B | A |

TABLE 1-continued
| Structure | IC$_{50}$(uM) | EC$_{50}$(uM) |
|---|---|---|
| 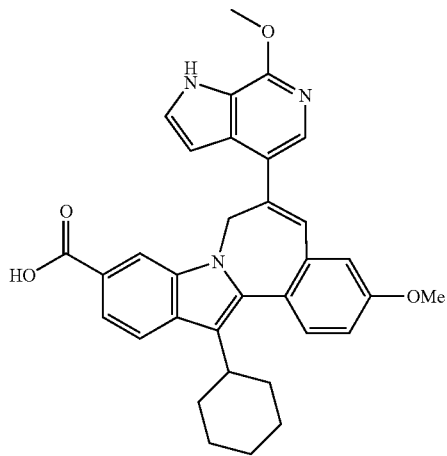 | B | B |
| 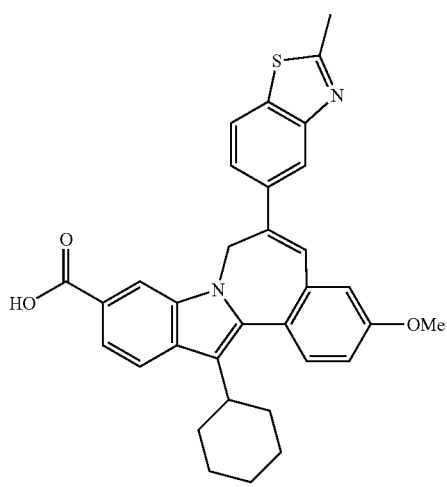 | B | A |
| 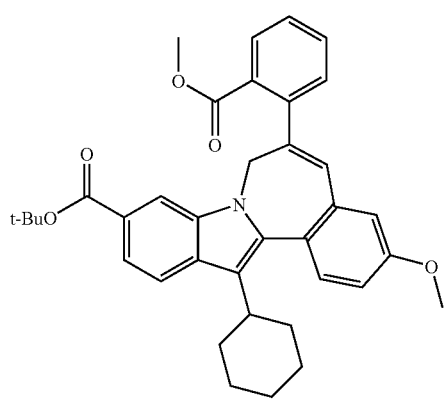 | | |

TABLE 1-continued

| Structure | IC$_{50}$(uM) | EC$_{50}$(uM) |
|---|---|---|
| 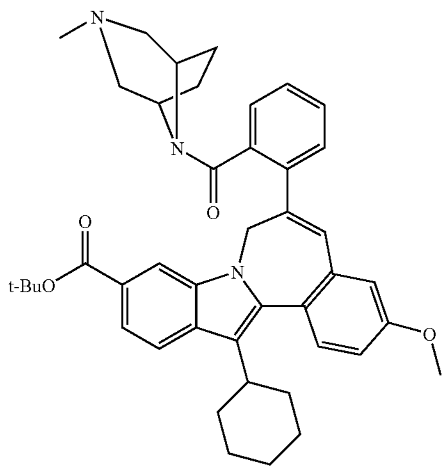 | A | A |
| | B | B |
| | B | B |

TABLE 1-continued

| Structure | IC$_{50}$(uM) | EC$_{50}$(uM) |
|---|---|---|
| (structure shown) | A | A |

A >0.5 μM;
B 0.00458 μM-0.5 μM;
IC$_{50}$ values were determined using the preincubation protocol.
EC$_{50}$ values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt or solvate thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable solvate or salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable solvate or salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |

TABLE 2-continued

| Brand Name | Type of Inhibitor or Target | Source Company |
|---|---|---|
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

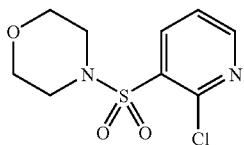

2-Chloro-3-(4-morpholinosulfonyl)-pyridine. To a solution of 2-chloropyridine-3-sulfonyl chloride (200 mg, 0.43 mmol) in triethylamine (0.158 mL, 1.13 mmol) and chloroform (2.80 mL) was added morpholine (0.090 mL, 1.04 mmol) at 0° C. The resulting solution was stirred for 1 hr at 0° C. and 3 hr at 22° C. 1M HCl (50 mL) was added and the aqueous layer was extracted with $CHCl_3$ (2×100 mL). The organic phase was dried over $Na_2SO_4$, filtered, and concentrated under reduced pressure to afford the title compound (226 mg, 91%) as a beige solid. MS m/z 263 (MH$^+$).

The following compound was synthesized by an analogous method as described above for 2-chloro-3-(4-morpholinosulfonyl)-pyridine:

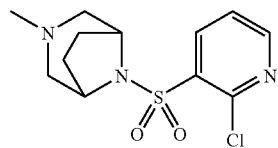

2-Chloro-3-[(3-methyl-3,8-diazabicyclo[3.2.1]oct-8-yl) carbonyl]-pyridine. MS m/z 302 (MH$^+$).

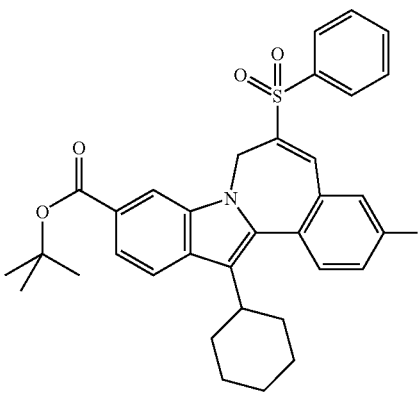

7H-Indolo[2,1-a][2]benzazepine-10-carboxylic acid, 13-cyclohexyl-3-methoxy-6-(phenyllsulfonyl)-, 1,1-dimethylethyl ester. To a solution of 1,1-dimethylethyl3-cyclohexyl-2-(2-formyl-4-methoxyphenyl)-1H-indole-6-carboxylate (6.00 g, 13.8 mmol) in dioxane (28.0 mL) and BEMP (7.97 mL, 27.6 mmol) was added phenyl vinyl sulfone (27.6 g, 2.21 mmol). The resulting mixture was stirred in a sealed tube in a microwave at 120° C. for 15 min. The resulting solution was concentrated under reduced pressure. Silica gel chromatography ($CH_2Cl_2$) of the concentrate afforded the title compound (6.36 g, 79%) as a yellow oil. MS m/z 584 (MH$^+$). 1H NMR(500 MHz, CHLOROFORM-d) δ ppm 1.18-1.33 (1 H, m), 1.34-1.45 (2 H, m), 1.49-57 (1 H, m), 1.64 (9H, s.), 1.74-1.82 (2 H, m), 1.90-2.09 (4 H, m), 2.73 (1 H, m,), 3.93 (3 H, s), 4.38 (1 H, broad d), 5.08 (1 H, br. d), 7.09 (1 H, d, J=2.75 Hz), 7.12-7.18 (3 H, m), 7.22 (1 H, d, J=7.45 Hz), 7.30 (1 H, s), 7.48 (1H, d, J=8.85 Hz), 7.54 (1 H, dd, J=8.55, 1.22 Hz), 7.61 (2 H, m), 7.67 (1 H, d, J=8.55), 8.01 (1 H, s).

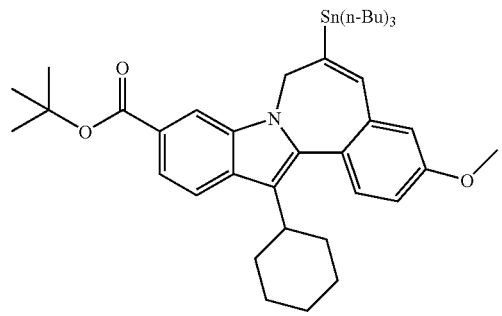

7H-indolo[2,1-a][2]benzazepine-10-carboxylic acid, 13-cyclohexyl-3-methoxy-6-(tributylstannyl)-, 1,1-dimethylethyl ester. Dissolve 7H-indolo[2,1-a][2]benzazepine-10-carboxylic acid, 13-cyclohexyl-3-methoxy-6-(phenylsulfonyl)-, 1,1-dimethylethyl ester (1.00 g, 1.71 mMol) in 26 mL of benzene along with bis(tributyltin) (2.8 mL, 5.54 mMol), tributyltin hydride (136 uL, 0.513 mMol) and triethylamine (1.05 mL, 7.5 mMol). The solution was sparged for approximately for 10 minutes with nitrogen then 2,2'-bisazoisobutyronitrile (AIBN) (96 mg, 0.58 mMol) added to the reaction. The reaction was heated to reflux under nitrogen for 2 hr. The reaction was followed by LC-MS using the following HPLC conditions: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=10 min; Flow rate=5 ml/min; Wavelength=220 nm; Column=Waters Xterra, 3 mm×50 mm, S7. To the reaction was added tributyltin hydride (0.45 mL, 1.7 mMol) and AIBN(95 mg, 0.58 mMol), the reaction heated to reflux for 2 hrs, and analyzed for progress. AIBN (99 mg, 0.60 mMol) added to the reaction and the reaction heated to reflux under for an additional 6 hrs using a timer. The reaction was analyzed by LC-MS for progress then tributyltin hydride(1.0 ml, 3.8 mMol) and AIBN (97 mg, 0.59 mMol) was added and the reaction heated to reflux for 2 hrs 20 min. The reaction was analyzed by LC-MS and AIBN (97 mg, 0.59 mMol) added to the reaction. The reaction was heated for 1 hr under nitrogen at reflux and the cooled and analyzed by LC-MS. Volatiles were removed in vacuo from the reaction and the reaction was purified by column chromatography using a $C_{18}$ packing of 190 g of YMC GEL ODS-A, 120A spherical 75 uM. The reaction residue (6.67 g of yellow oil) was dissolved in a minimum of dichloromethane and the solution applied onto the reverse phase column packed in 10% dichloromethane in acetonitrile. Initial elution was done using 10% dichloromethane in acetonitrile followed by elution with 15% dichloromethane in acetonitrile. The chromatography was monitored by TLC using Whatman MKC18F reverse phase 1"×3" 200 uM thickness TLC plates eluting using 15% dichloromethane in acetonitrile. Compound observation was accomplished by UV lamp at 254 nm and iodine staining of TLC plates. Product fractions were collected and volatiles removed in vacuuo to yield 647 mg (52%) as a pale yellow foam. 1H NMR (500 MHz, CHLOROFORM-D) δ ppm 0.71-0.83 (m, 9 H) 0.85-0.96 (m, 3H) 0.95-1.08 (m, 6 H) 1.15-1.27 (m, 7 H) 1.27-1.49 (m, 11 H) 1.53 (s, 5 H) 1.60-1.67 (m, 9 H) 1.68-1.82 (m, 2 H) 1.84-1.96 (m, 1 H) 1.96-2.16 (m, 3 H) 2.74-2.91 (m, 1 H) 3.90 (s, 3 H) 4.16-4.40 (m, 1 H) 4.82-5.03 (m, 1 H) 6.72-6.90 (m, 2 H) 6.96 (dd, J=8.55, 2.44 Hz, 1 H) 7.43 (d, J=8.55 Hz, 1 H) 7.66 (dd, J=8.39, 1.37 Hz, 1 H) 7.81 (d, J=8.55 Hz, 1 H) 8.04 (s, 1 H); LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=10 min; Flow rate=5 ml/min; Wavelength=220 nm; Column=Waters Xterra, 3 mm×50 mm, S7; Retention Time=4.2 min, MS m/z 734 (MH+).

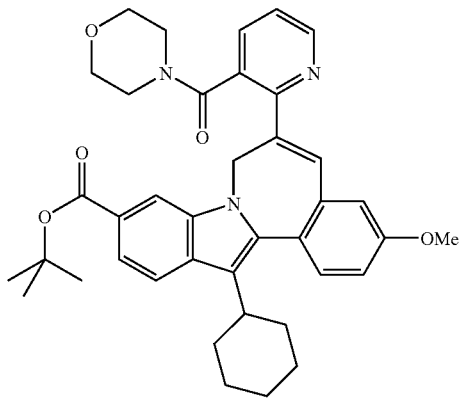

7H-indolo[2,1-a][2]benzazepine-10-carboxylic acid, 13-cyclohexyl-3-methoxy-6-[3-(4-morpholinylcarbonyl)-2-pyridinyl]-, 1,1-dimethylethyl ester. To a solution of 7H-Indolo[2,1-a][2]benzazepine-10-carboxylic acid, 13-cyclohexyl-3-methoxy-6-(tributylstannyl)-, 1,1-dimethylethyl ester (100 mg, 0.136 mmol) dissolved in THF (2 mL) was added 4-[(2-chloropyridin-3-yl)carbonyl]morpholine (47 mg, 0.21 mmol), TEA (0.029 mL), and tetrakis(triphenylphosphine)palladium (16 mg, 0.014 mmol). This mixture was capped under nitrogen and heated in a microwave at 160° C. for 2 hr. The reaction mixture was filtered purified by prep HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. This afforded the title compound (38 mg, 44%) as a yellow paste. MS m/z 634 (MH+).

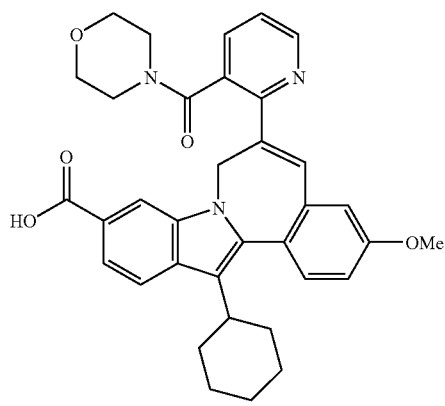

7H-indolo[2,1-a][2]benzazepine-10-carboxylic acid, 13-cyclohexyl-3-methoxy-6-[3-(4-morpholinylcarbonyl)-2-pyridinyl]-. 7H-indolo[2,1-a ][2]benzazepine-10-carboxylic acid, 13-cyclohexyl-3-methoxy-6-[3-(4-morpholinylcarbonyl)-2-pyridinyl]-, 1,1-dimethylethyl ester (50 mg, 0.079 mmol) was dissolved in 1,2-dichloroethane (1 mL) and trifluoroacetic acid (1 mL). The resulting solution was stirred at 22° C. for 2 hr. The solution was concentrated under reduced pressure to afford a yellow solid. This afforded the title compound (41 mg, 64%) as a yellow paste. 1H NMR (500 MHz, CHLOROFORM-D) δ ppm 1.14-2.27 (m, 10H) 2.42 (m, 1 H) 2.92 (m, 3 H) 3.30 (m, 3 H) 3.61-3.80 (m, 2 H) 3.89 (s, 3 H) 4.53 (br d, 1 H) 5.90 (br d, 1 H) 6.92 (d, 1 H) 7.07 (dd, j=8.55, 2.44 Hz, 1 H) 7.17 (s, 1 H) 7.40 (m, 1 H) 7.52 (d, j=8.55 Hz, 1 H) 7.70 (m, 2 H) 7.86 (d, J=8.55 Hz, 1 H) 7.99 (s, 1 H) 8.82 (s, 1 H). MS m/z 578 (MH+).

The following compounds were synthesized by an analogous method as described above for 7H-indolo[2,1-a][2]benzazepine-10-carboxylic acid, 13-cyclohexyl-3-methoxy-6-[3-(4-morpholinylcarbonyl)-2-pyridinyl]-:

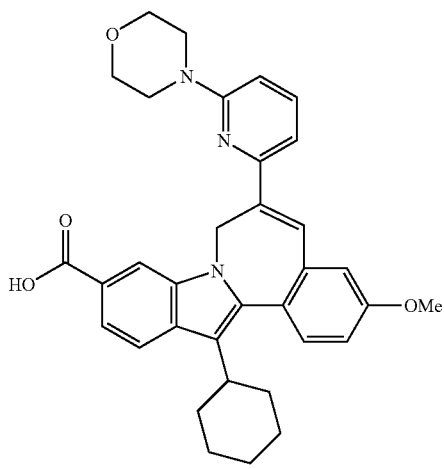

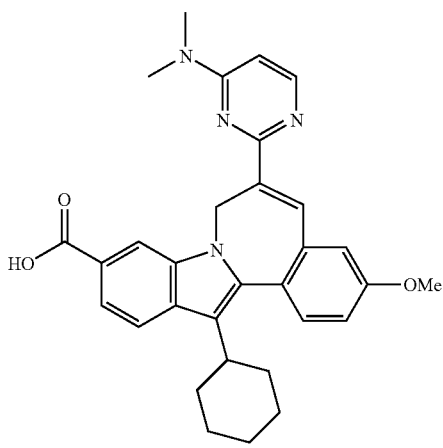

7H-indolo[2,1-a][2]benzazepine-10-carboxylic acid, 13-cyclohexyl-3-methoxy-6-[6-(4-morpholinyl)-2-pyridinyl]-. 1H NMR (500 MHz, CHLOROFORM-D) δ ppm 1.14-2.27 (m, 10 H) 2.88 (m, 1 H) 3.47 (br m, 2 H) 3.70 (m, 3 H) 3.92 (s, 3 H) 3.96 (m, 3 H) 4.38 (br d, 1 H) 6.02 (br d, 1 H) 6.70 (m, 1 H) 7.02 (m, 2 H) 7.13 (d, 1 H) 7.44 (s, 1 H) 7.52 (d, 1 H) 7.57 (t, 1 H) 7.82 (d, 1 H) 8.25 (s, 1 H). LCMS: m/e 550 (M+H).

7H-indolo[2,1-a][2]benzazepine-10-carboxylic acid, 13-cyclohexyl-6-[4-(dimethylamino)-2-pyrimidinyl]-3-methoxy-. 1H NMR (500 MHz, CHLOROFORM-D) δ ppm 1.13-2.16 (m, 10 H) 2.91 (m, 1 H) 3.71 (br s, 3 H) 3.85 (br s, 3 H) 3.90 (s, 3 H) 4.22 (br d, 1 H) 6.12 (br d, 1 H) 6.68 (s, 1 H) 6.72 (m, 1 H) 6.90 (s, 1 H) 7.06 (m, 2 H) 7.55 (d, 1 H) 7.79 (d, 1 H) 7.90 (d, 1 H) 8.43 (s, 1 H). LCMS: m/e 509 (M+H).

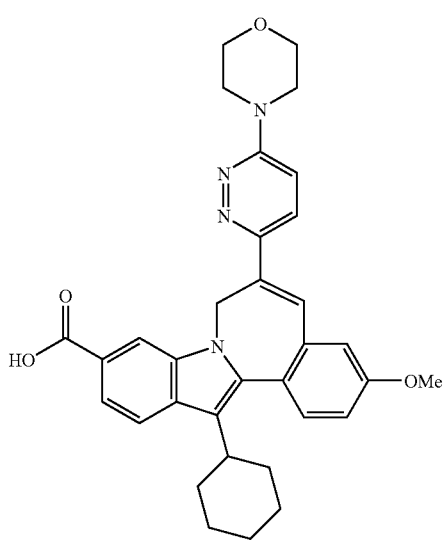

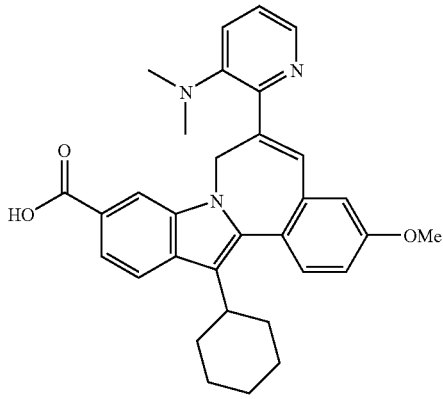

7H-indolo[2,1-a][2]benzazepine-10-carboxylic acid, 13-cyclohexyl-3-methoxy-6-[6-(4-morpholinyl)-3-pyridazinyl]-. 1H NMR (500 MHz, CHLOROFORM-D) δ ppm 1.14-2.14 (m, 10 H) 2.88 (m, 1 H) 3.70 (br m, 4 H) 3.91 (s, 3 H) 3.96 (m, 4 H) 4.42 br d, 1 H) 5.78 (br d, 1 H) 6.79 (d, 1 H) 7.06 (m, 2 H) 7.33 (d, 1 H) 7.42 (s, 1 H) 7.49 (d, 1 H) 7.59 (t, 1 H) 7.87 (d, 1 H) 8.18 (s, 1 H). LCMS: m/e 551 (M+H).

7H-indolo[2,1-a][2]benzazepine-10-carboxylic acid, 13-cyclohexyl-6-[3-(dimethylamino)-2-pyridinyl]-3-methoxy-. 1H NMR (500 MHz, CHLOROFORM-D) δ ppm 1.17-2.11 (m, 10 H) 2.87 (m, 1 H) 3.30 (br s, 3 H) 3.69 (br s, 3 H) 3.95 (s, 3 H) 4.40 (br d, 1 H) 5.95 (br d, 1 H) 6.52 (d, 1 H) 7.14 (dd, 1 H) 7.20 (s, 1 H) 7.32 (m, 1 H) 7.52 (d, 1 H) 7.90 (d, 1 H) 8.29 (d, 1 H) 8.33 (m, 1 H) 8.50 (s, 1 H). LCMS: m/e 508 (M+H).

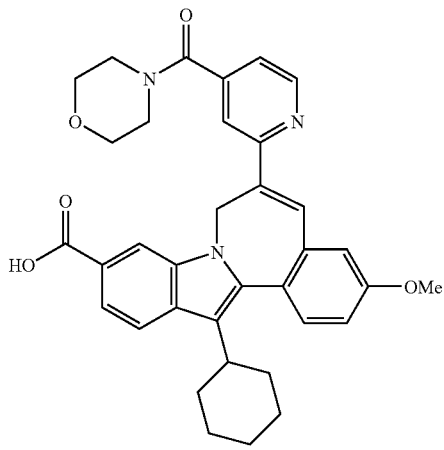

7H-indolo[2,1-a][2]benzazepine-10-carboxylic acid, 13-cyclohexyl-3-methoxy-6-[4-(4-morpholinylcarbonyl)-2-pyridinyl]-. 1H NMR (500 MHz, CHLOROFORM-D) δ ppm 1.16-2.15 (m, 10 H) 2.90 (m, 1 H) 3.42 (m, 2 H) 3.53 (m, 2 H) 3.80 (m, 4 H) 3.92 (s, 3 H) 4.51 (br d, 1 H) 5.92 (br d, 1 H) 7.06 (d, 1 H) 7.12 (dd, 1 H) 7.38 (d, 1 H) 7.56 (d, 1 H) 7.60 (s, 1 H) 7.79 (m, 2 H) 7.90 (d, 1 H) 8.39 (s, 1 H) 8.90 (d, 1 H) LCMS: m/e 578 (M+H).

7H-indolo[2,1-a][2]benzazepine-10-carboxylic, 13-cyclohexyl-3-methoxy-6-[3[(3-methyl-3,8-diazabicyclo[3.2.1]oct-8-yl)sulfonyl]-2-pyridinyl]-. 1H NMR (500 MHz, CHLOROFORM-D) δ ppm 1.16-2.13 (m, 13 H) 2.30 (m, 1 H) 2.43 (m, 1 H) 2.81 (s, 3 H) 2.89-3.12 (m, 3 H) 3.32 (m, 2 H) 3.67 (m, 1 H) 3.89 (s, 3 H) 4.50 (br d, 1 H) 6.02 (br d, 1 H) 6.93 (d, 1 H) 7.07 (dd, 1 H) 7.20 (s, 1 H) 7.35 (m, 2 H) 7.52 (d, 1 H) 7.58 (m, 1 H) 7.88 (m, 2 H) 8.75 (d, 1 H). LCMS: m/e 653 (M+H).

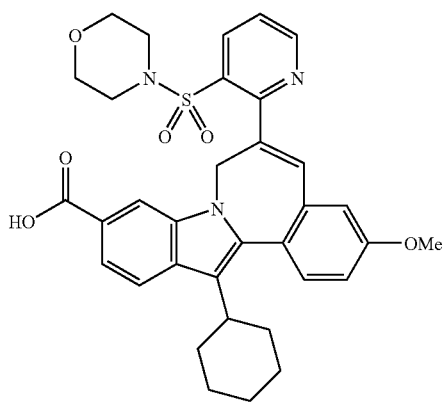

7H-indolo[2,1-a][2]benzazepine-10-carboxylic acid, 13-cyclohexyl-3-methoxy-6-[3-(4-morpholinylsulfonyl)-2-pyridinyl]-. 1H NMR (500 MHz, CHLOROFORM-D) δ ppm 1.14-2.13 (m, 10 H) 2.51 (m, 4 H) 2.91 (m, 1 H) 3.24 (m, 4 H) 3.88 (s, 3 H) 4.65 (br d, 1 H) 5.47 (br d, 1 H) 6.91 (d, 1 H) 7.05 (dd, 1 H) 7.30 (s, 1 H) 7.47 (m, 1 H) 7.53 (d, 1 H) 7.71 (d, 1 H) 7.88 (d, 1 H) 8.02 (s, 1 H) 8.40 (d, 1 H) 8.87 (d, 1 H). LCMS: m/e 614 (M+H).

7H-indolo[2,1-a][2]benzazepine-10-carboxylic acid, 13-cyclohexyl-6-[3-(3,3-dimethyl-2-oxo-1-azetidinyl)-2-pyridinyl]-3-methoxy-. 1H NMR (500 MHz, CHLOROFORM-D) δ ppm 0.85 (br s, 3 h) 1.09 (br s, 3 H) 1.13-2.16 (m, 11 H) 2.78 (m, 1 H) 2.91 (m, 1 H) 3.90 (s, 3 H) 4.63 (br d, 1 H) 5.44 (br d, 1 H) 6.78 (s, 1 H) 6.92 (d, 1 H) 7.10 (dd, 1 H) 7.25 (m, 1 H) 7.36 (m, 1 H) 7.54 (d, 1 H) 7.88 (m, 2 H) 8.27 (d, 1 H) 8.50 (d, 1 H). LCMS: m/e 562 (M+H).

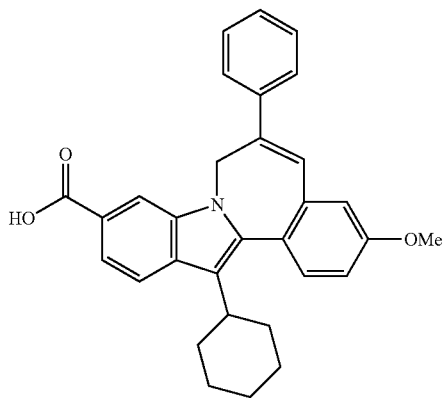

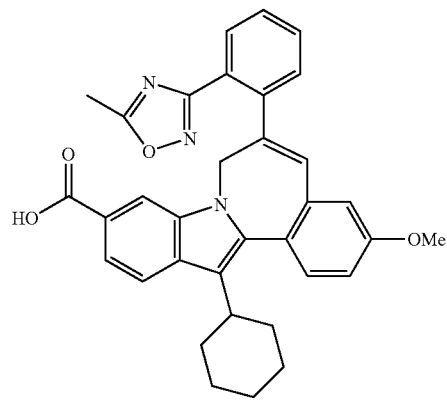

7H-indolo[2,1-a][2]benzazepine-10-carboxylic acid, 13-cyclohexyl-3-methoxy-6-phenyl-. 1H NMR (500 MHz, CHLOROFORM-D) δ ppm 1.17-2.15 (m, 10 H) 2.91 (m, 1 H) 3.92 (s, 3 H) 4.53 (br d, 1 H) 5.88 (br d, 1 H) 6.97 (dd, 1 H) 7.02 (m, 1 H) 7.32 (m, 2 H) 7.41 (m, 2 H) 7.53 (m, 3 H) 7.90 (d, 1 H) 8.05 (s, 1 H) 8.37 (s, 1 H). LCMS: m/e 464 (M+H).

7H-indolo[2,1-a][2]benzazepine-10-carboxylic acid, 13-cyclohexyl-3-methoxy-6-[2-(5-methyl-1,2,4-oxadiazol-3-yl)phenyl]-. 1H NMR (500 MHz, CHLOROFORM-D) δ ppm 1.18-2.12 (m, 10 H) 2.18 (s, 3 H) 2.93 (m, 1 H) 3.90 (s, 3 H) 4.59 (br d, 1 H) 4.76 (br d, 1 H) 6.71 (s, 1 H) 6.94 (d, 1 H) 7.02 (dd, 1 H) 7.22 (m, 1 H) 7.48 (m, 4 H) 7.91 (m, 2 H) 8.58 (s, 1 H). LCMS: m/e 546 (M+H).

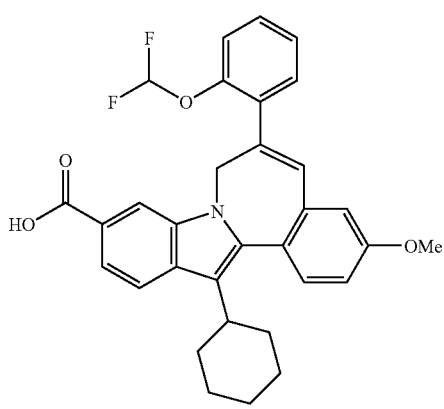

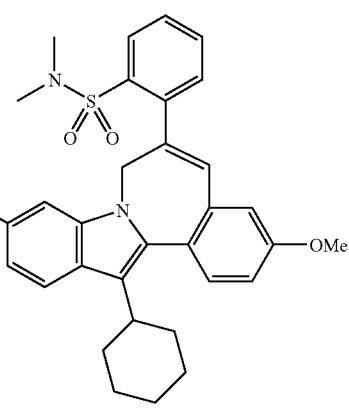

7H-indolo[2,1-a][2]benzazepine-10-carboxylic acid, 13-cyclohexyl-6-[2-(difluoromethoxy)phenyl]-3-methoxy-. 1H NMR (500 MHz, CHLOROFORM-D) δ ppm 1.17-2.13 (m, 10 H) 2.90 (m, 1 H) 3.91 (s, 3 H) 4.60 (br d, 1 H) 5.19 (br d, 1 H) 6.30 (t, 1 H) 6.83 (s, 1 H) 6.95 (d, 1 H) 7.05 (dd, 1 H) 7.21 (m, 3 H) 7.38 (m, 2 H) 7.52 (d, 1 H) 7.90 (m, 2 H). LCMS: m/e 530 (M+H).

7H-indolo[2,1-a][2]benzazepine-10-carboxylic acid, 13-cyclohexyl-6-[2-[(dimethylamino)sulfonyl]phenyl]-3-methoxy-. 1H NMR (500 MHz, CHLOROFORM-D) δ ppm 1.18-2.13 (m, 10 H) 2.73 (br s, 6 H) 2.91 (m, 1 H) 3.90 (s, 3 H) 4.70 (br d, 1 H) 5.00 (br d, 1 H) 6.87 (s, 1 H) 6.93 (br d, 1 H) 7.03 (dd, 1 H) 7.35-7.51 (m, 4 H) 7.70 (s, 1 H) 7.93 (m, 2 H) 8.17 (s, 1 H). LCMS: m/e 571 (M+H).

71

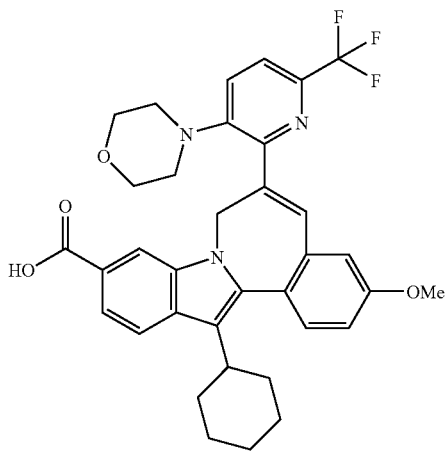

7H-indolo[2,1-a][2]benzazepine-10-carboxylic acid, 13-cyclohexyl-3-methoxy-6-[2-(4-morpholinyl)-5-(trifluoromethyl)phenyl]-. 1H NMR (500 MHz, CHLOROFORM-D) δ ppm 1.12-2.10 (m, 10 H) 2.35 (m, 1 H) 2.83 (m, 2 H) 3.15-3.81 (m, 6 H) 3.93 (s, 3 H) 5.05 (d, 1 H) 5.55 (d, 1 H) 6.30 (d, 1 H) 6.36 (s, 1 H) 6.77 (m, 2 H) 6.88 (dd, 1 H) 7.40 (m, 2 H) 7.52 (s, 1 H) 7.61 (d, 1 H) 7.80 (s, 1 H). LCMS: m/e 617 (M+H).

72

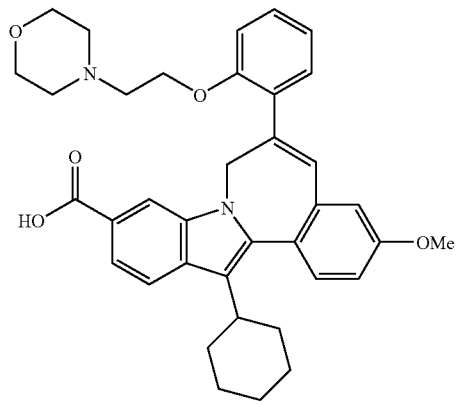

7H-indolo[2,1-a][2]benzazepine-10-carboxylic acid, 13-cyclohexyl-3-methoxy-6-[2-[2-(4-morpholinyl)ethoxy]phenyl]-. 1H NMR (500 MHz, CHLOROFORM-D) δ ppm 1.20-2.21 (m, 10 H) 2.40 (m, 1 H) 2.82 (m, 1 H) 3.00 (m, 3 H) 3.47 (m, 3 H) 3.63 (m, 3 H) 3.92 (s, 3 H) 4.27 (m, 2 H) 4.49 (br d, 1 H) 5.00 (br d, 1 H) 6.78 (s, 1 H) 6.88 (dd, 1 H) 6.93 (d, 1 H) 7.04 (m, 2 H) 7.33 (m, 1 H) 7.41 (m, 1 H) 7.51 (d, 1 H) 7.98 (m, 3 H). LCMS: m/e 593 (M+H).

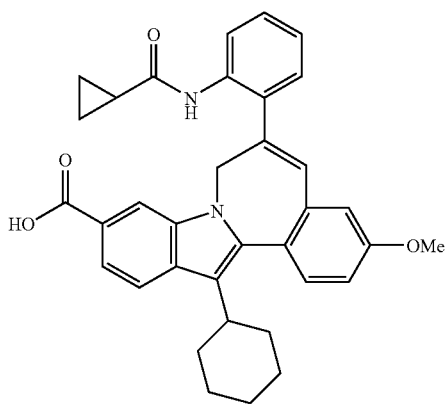

7H-indolo[2,1-a][2]benzazepine-10-carboxylic acid, 13-cyclohexyl-6-[2-[(cyclopropylcarbonyl)amino]phenyl]-3-methoxy-. 1H NMR (500 MHz, CHLOROFORM-D) δ ppm 0.30-1.09 (m, 4 H) 1.13-2.16 (m, 10 H) 2.50 (m, 1 H) 2.75 (m, 1 H) 3.90 (s, 3 H) 4.22 (d, 1 H) 4.63 (br d, 1 H) 5.44 (br d, 1 H) 6.78 (m, 2 H) 6.92 (d, 1 H) 7.10 (dd, 1 H) 7.25 (m, 1 H) 7.36 (m, 1 H) 7.54 (d, 1 H) 7.88 (m, 2 H) 8.27 (d, 1 H) 8.50 (d, 1 H). LCMS: m/e 547 (M+H).

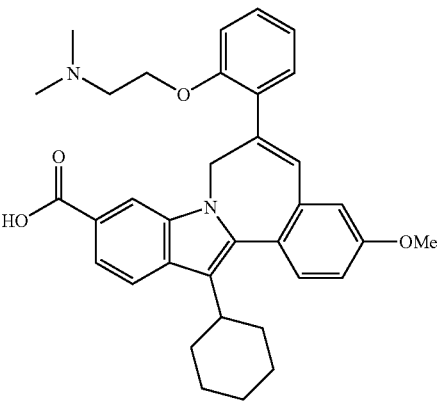

7H-indolo[2,1-a][2]benzazepine-10-carboxylic acid, 13-cyclohexyl-6-[2-[2-dimethylamino)ethoxy]phenyl]-3-methoxy-. 1H NMR (500 MHz, CHLOROFORM-D) δ ppm 1.20-2.40 (m, 16 H) 2.92 (m, 2 H) 3.50 (m, 1 H) 3.92 (s, 3 H) 4.21 (m, 2 H) 4.49 (br d, 1 H) 5.00 (br d, 1 H) 6.75 (s, 1 H) 6.87 (dd, 1 H) 6.93 (d, 1 H) 7.04 (m, 2 H) 7.25 (m, 1 H) 7.33 (m, 1 H) 7.41 (m, 1 H) 7.51 (d, 1 H) 8.00 (m, 2 H). LCMS: m/e 551 (M+H).

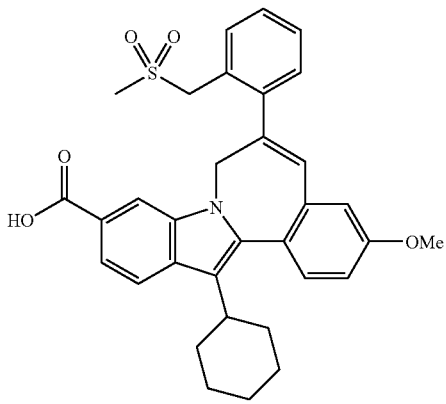

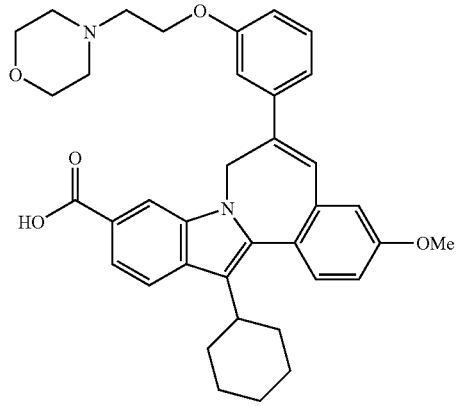

7H-indolo[2,1-a][2]benzazepine-10-carboxylic acid, 13-cyclohexyl-3-methoxy-6-[2-[(methylsulfonyl)methyl]phenyl]-. 1H NMR (500 MHz, CHLOROFORM-D) δ ppm 1.19-2.20 (m, 10 H) 2.45 (br s, 3 H) 2.90 (m, 1 H) 3.60 (br s, 1 H) 3.91 (s, 3 H) 4.19 (br s, 1 H) 4.62 (br d, 1 H) 5.03 (br d, 1 H) 6.75 (s, 1 H) 6.90 (d, 1 H) 7.04 (dd, 1 H) 7.17 (m, 1 H) 7.36 (m, 2 H) 7.45 (m, 2 H) 7.88 (s, 1 H) 7.92 (m, 2 H). LCMS: m/e 556 (M+H).

7H-indolo[2,1-a][2]benzazepine-10-carboxylic acid, 13-cyclohexyl-3-methoxy-6-[3-[2-(4-morpholinyl)ethoxy]phenyl]-. 1H NMR (500 MHz, CHLOROFORM-D) δ ppm 1.20-2.15 (m, 10 H) 2.90 (m, 1 H) 3.03 (m, 4 H) 3.42 (m, 5 H) 3.92 (s, 3 H) 3.98 (m, 2 H) 4.50 (br d, 1 H) 4.63 (m, 1 H) 5.28 (br d, 1 H) 6.75 (dd, 1 H) 6.95 (m, 2 H) 7.01 (dd, 1H) 7.20 (m, 2H) 7.27 (m, 1H) 7.50 (d, 1H) 7.69 (d, 1 H) 7.88 (d, 1 H) 8.32 (s, 1 H). LCMS: m/e 593 (M+H).

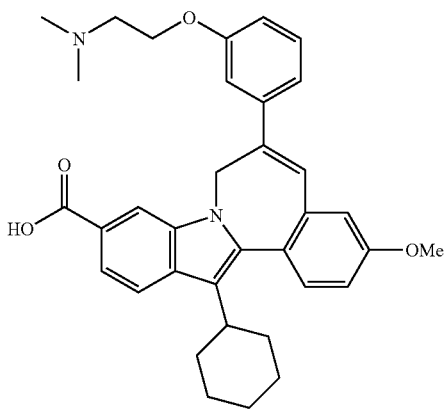

7H-indolo[2,1-a][2]benzazepine-10-carboxylic acid, 13-cyclohexyl-6-[3-[2-(dimethylamino)ethoxy]phenyl]-3-methoxy-. 1H NMR (500 MHz, CHLOROFORM-D) δ ppm 1.17-2.13 (m, 10 H) 2.90 (m, 1 H) 3.00 (br s, 6 H) 3.60 (m, 2 H) 3.92 (s, 3 H) 4.29 (m, 1 H) 4.49 (br d, 1 H) 4.72 (m, 1 H) 5.45 (br d, 1 H) 6.75 (s, 1 H) 6.87 (dd, 1 H) 6.93 (d, 1 H) 7.04 (m, 2 H) 7.25 (m, 1 H) 7.33 (m, 1 H) 7.41 (m, 1 H) 7.51 (d, 1 H) 7.90 (m, 2 H). LCMS: m/e 551 (M+H).

7H-indolo[2,1-a][2]benzazepine-10-carboxylic acid, 13-cyclohexyl-6-[2-[[[2-(dimethylamino)ethyl]methylamino]sulfonyl]phenyl]-3-methoxy-. 1H NMR (500 MHz, CHLOROFORM-D) δ ppm 1.15-2.15 (m, 10 H) 2.65-3.58 (m, 14 H) 3.92 (s, 3 H) 4.65 (br d, 1 H) 5.04 (br d, 1 H) 6.75 (m, 1 H) 6.97 (dd, 1 H) 7.02 (m, 2 H) 7.49 (m, 5 H) 7.90 (m, 2 H). LCMS: m/e 628 (M+H).

75

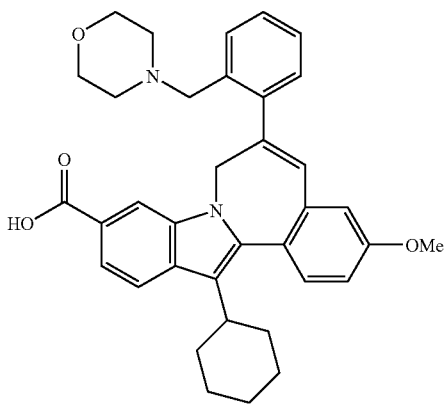

7H-indolo[2,1-a][2]benzazepine-10-carboxylic acid, 13-cyclohexyl-3-methoxy-6-[2-(4-morpholinylmethyl)phenyl]-. 1H NMR (500 MHz, CHLOROFORM-D) δ ppm 1.21-2.19 (m, 10 H) 2.58 (m, 2 H) 2.93 (m, 1 H) 3.11-3.59 (m, 4 H) 3.91 (s, 3 H) 3.95 (m, 4 H) 4.70 (br d, 1 H) 5.09 (br d, 1 H) 6.63 (s, 1 H) 6.92 (d, 1 H) 7.11 (dd, 1 H) 7.40 (m, 2 H) 7.53 (m, 4 H) 7.72 (s, 1 H) 7.97 (d, 1 H). LCMS: m/e 563 (M+H).

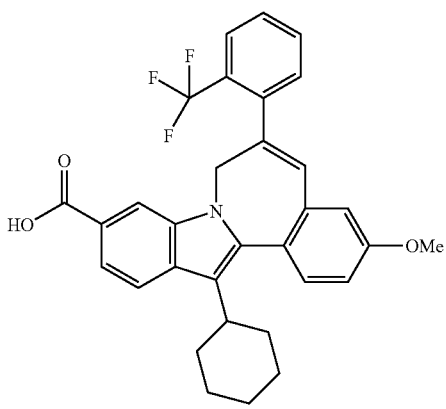

7H-indolo[2,1-a][2]benzazepine-10-carboxylic acid, 13-cyclohexyl-3-methoxy-6-[2-(trifluoromethyl)phenyl]-. LCMS: m/e 532 (M+H) retention time 2.99 min.

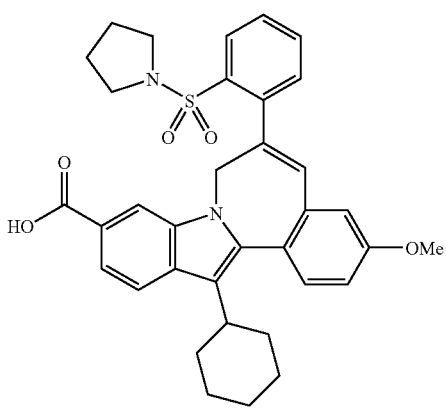

76

7H-indolo[2,1-a][2]benzazepine-10-carboxylic acid, 13-cyclohexyl-3-methoxy-6-[2-(1-pyrrolidinylsulfonyl)phenyl]-. LCMS: m/e 597 (M+H) retention time 2.83 min.

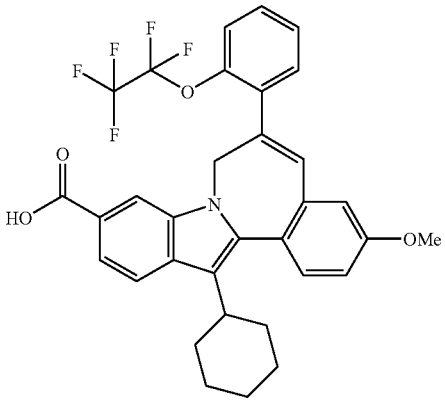

7H-indolo[2,1-a][2]benzazepine-10-carboxylic acid, 13-cyclohexyl-3-methoxy-6-[2-(1,1,2,2-tetrafluoroethoxy)phenyl]-. LCMS: m/e 598 (M+H) retention time 3.11 min.

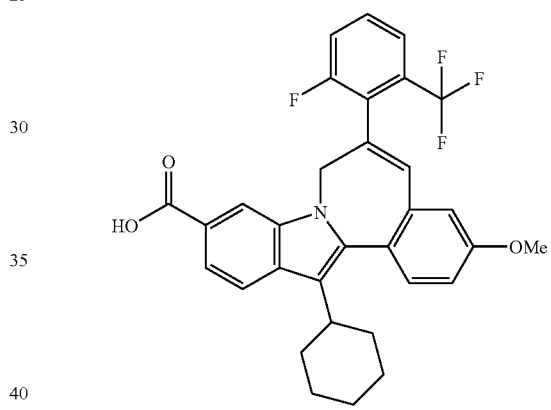

7H-indolo[2,1-a][2]benzazepine-10-carboxylic acid, 13-cyclohexyl-6-[2-fluoro-6-(trifluoromethyl)phenyl]-3-methoxy-. LCMS: m/e 550 (M+H) retention time 3.03 min.

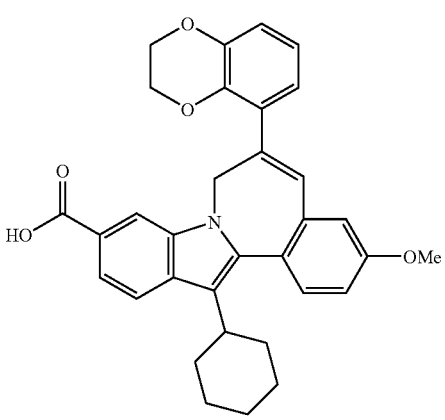

7H-indolo[2,1-a][2]benzazepine-10-carboxylic acid, 13-cyclohexyl-6-(2,3-dihydro-1,4-benzodioxin-5-yl)-3-methoxy-N. LCMS: m/e 522 (M+H) retention time 2.89 min.

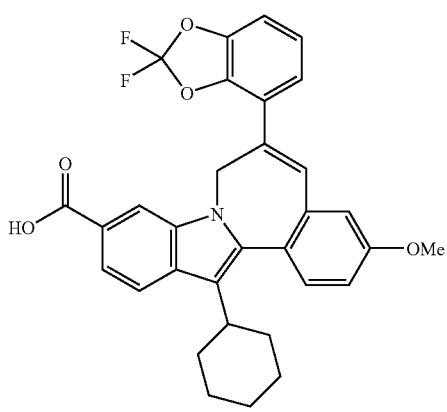

7H-indolo[2,1-a][2]benzazepine-10-carboxylic acid, 13-cyclohexyl-6-(2,2-difluoro-1,3-benzodioxol-4-yl)-3-methoxy-. LCMS: m/e 544 (M+H) retention time 2.95 min.

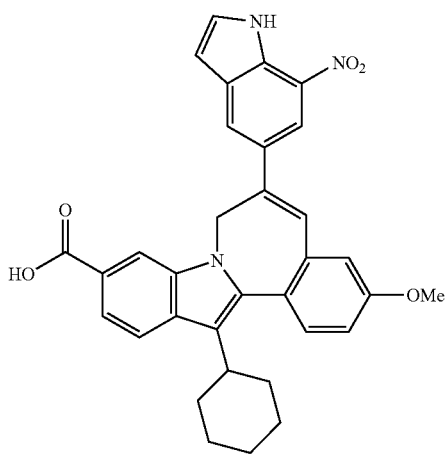

7H-indolo[2,1-a][2]benzazepine-10-carboxylic acid, 13-cyclohexyl-3-methoxy-6-(7-nitro-1H-indol-5-yl)-. LCMS: m/e 548 (M+H) retention time 2.81 min.

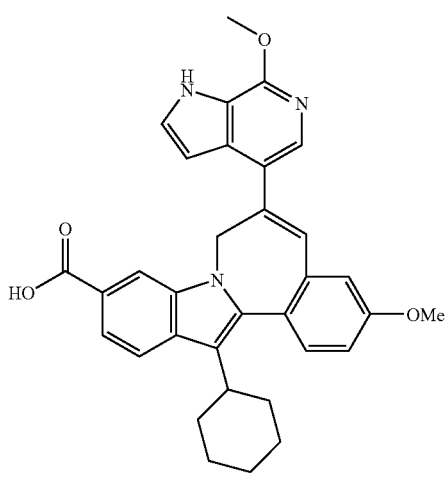

7H-indolo[2,1-a][2]benzazepine-10-carboxylic acid, 13-cyclohexyl-3-methoxy-6-(7-methoxy-1H-pyrrolo[2,3-c]pyridin-4-yl)-. LCMS: m/e 534 (M+H) retention time 2.87 min.

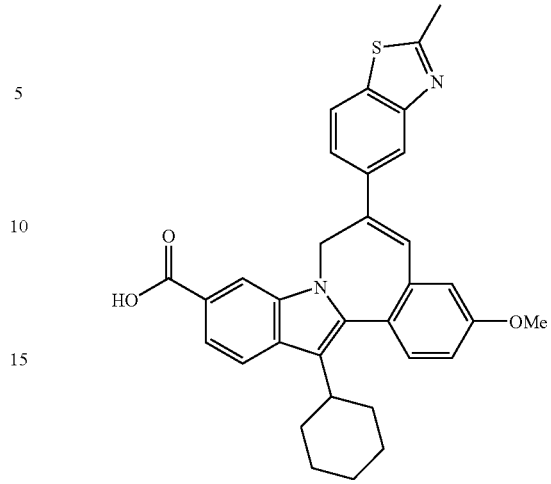

7H-indolo[2,1-a][2]benzazepine-10-carboxylic acid, 13-cyclohexyl-3-methoxy-6-(2-methyl-5-benzothiazolyl)-. LCMS: m/e 535 (M+H) retention time 2.79 min.

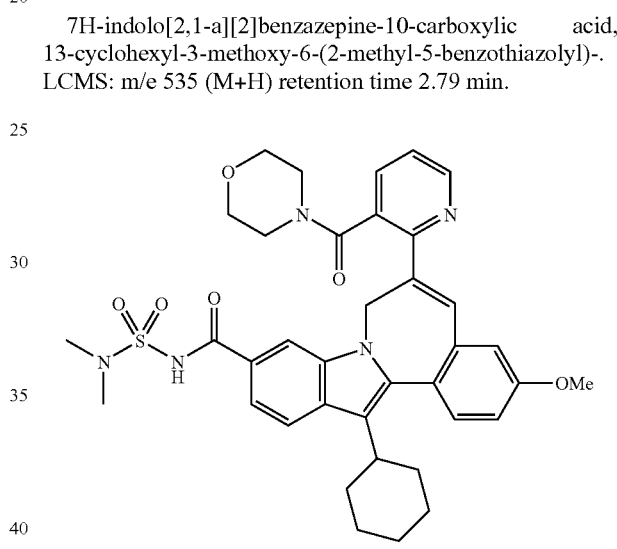

7H-indolo[2,1-a][2]benzazepine-10-carboxamide, 13-cyclohexyl-N-[(dimethylamino)sulfonyl]-3-methoxy-6-[3-(4-morpholinylcarbonyl)-2-pyridinyl]-. 7H-indolo[2,1-a][2]benzazepine-10-carboxylic acid, 13-cyclohexyl-3-methoxy-6-[3-(4-morpholinylcarbonyl)-2-pyridinyl]-(40 mg, 0.077 mmol) was dissolved in THF (1 mL) and carbonyldiimidazole (18 mg, 0.11 mmol) was added. The resulting solution was stirred at 22° C. under a nitrogen atmosphere for 1.5 hrs then heated to reflux for 1 hr. Upon cooling to room temperature under a nitrogen atmosphere, N,N-dimethylsulfamide (70 mg, 0.46 mmol) and DBU (0.012 mL, 0.92 mmol) were added. The reaction was heated to reflux for 1 hr and stirred at 22° C. for 18 hr. 1M HCl (10 mL) was added and the aqueous layer was extracted with CHCl$_3$ (2×25 mL). The organic phase was concentrated under reduced pressure and purified by prep HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. This afforded the title compound (36 mg, 67%) as a yellow paste. 1H NMR (500 MHz, CHLOROFORM-D) δ ppm 1.14-2.27 (m, 11 H) 2.48 (m, 1 H) 2.94 (m, 3 H) 3.07 (s, 3 H) 3.33 (m, 3 H) 3.60-3.80 (m, 2 H) 3.89 (s, 3 H) 4.52 (br d, 1 H) 5.91 (br d, 1

H) 6.91 (d, 1 H) 7.05 (dd, j=8.55, 2.44 Hz, 1 H) 7.16 (s, 1 H) 7.42 (m, 1 H) 7.53 (d, J=8.55 Hz, 1 H) 7.71 (m, 1 H) 7.85 (d, J=8.55 Hz, 1 H) 8.00 (s, 1 H) 8.81 (s, 1 H). MS m/z 684 (MH⁺).

The following compounds were synthesized by an analogous method as described above for 7H-indolo[2,1-a][2]benzazepine-10-carboxamide, 13-cyclohexyl-N-[(dimethylamino)sulfonyl]-3-methoxy-6-[3-(4-morpholinylcarbonyl)-2-pyridinyl]-:

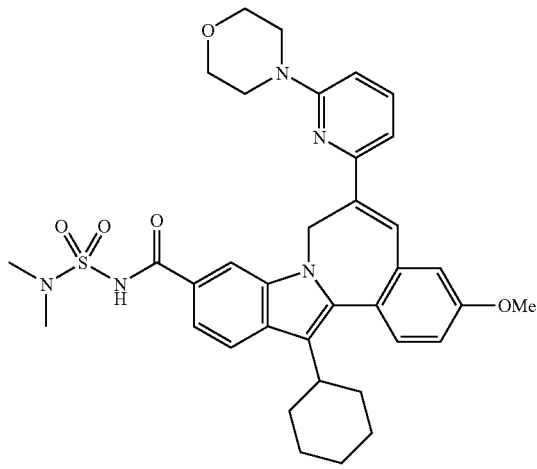

7H-indolo[2,1-a][2]benzazepine-10-carboxamide, 13-cyclohexyl-N-[(dimethylamino)sulfonyl]-3-methoxy-6-[6-(4-morpholinyl)-2-pyridinyl]-. 1H NMR (500 MHz, CHLOROFORM-D) δ ppm 1.15-2.21 (m, 10 H) 2.89 (m, 1 H) 3.05 (s, 6 H) 3.49 (br m, 2 H) 3.73 (m, 3 H) 3.91 (s, 3 H) 3.96 (m, 3 H) 4.38 (br d, 1 H) 6.01 (br d, 1 H) 6.70 (m, 1 H) 7.04 (m, 2 H) 7.13 (d, 1 H) 7.44 (s, 1 H) 7.52 (d, 1 H) 7.57 (t, 1 H) 7.63 (d, 1 H) 7.82 (d, 1 H) 8.25 (s, 1 H). LCMS: m/e 656 (M+H).

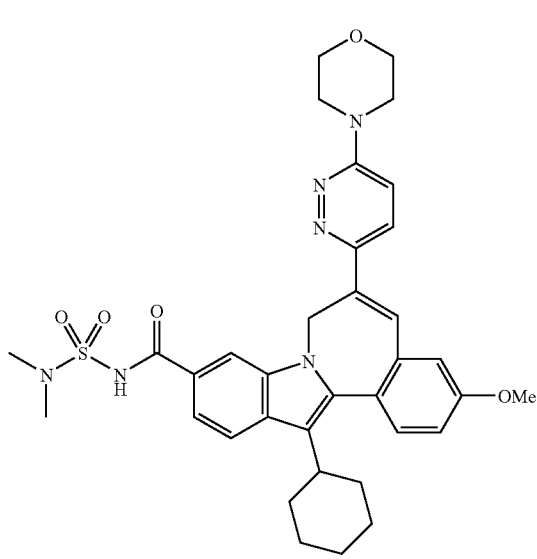

7H-indolo[2,1-a][2]benzazepine-10-carboxamide, 13-cyclohexyl-N-[(dimethylamino)sulfonyl]-3-methoxy-6-[6-(4-morpholinyl)-3-pyridazinyl]-. 1H NMR (500 MHz, CHLOROFORM-D) δ ppm 1.16-2.17 (m, 10 H) 2.89 (m, 1 H) 3.02 (s, 6 H) 3.70 (br m, 4 H) 3.91 (s, 3 H) 3.96 (m, 4 H) 4.42 (br d, 1 H) 5.78 (br d, 1 H) 6.79 (d, 1 H) 7.06 (m, 2 H) 7.33 (d, 1 H) 7.42 (s, 1 H) 7.49 (d, 1 H) 7.59 (t, 1 H) 7.87 (d, 1 H) 8.18 (s, 1 H). LCMS: m/e 657 (M+H).

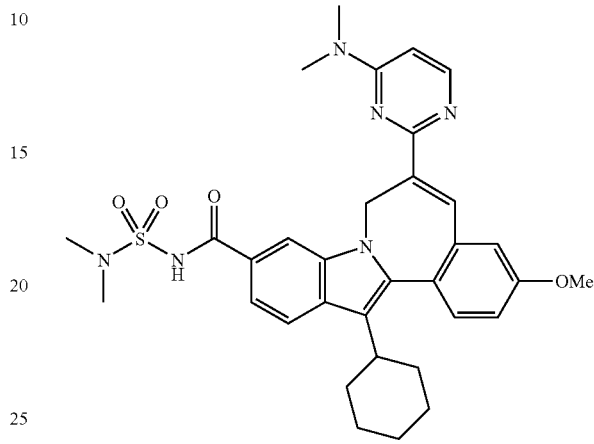

7H-indolo[2,1-a][2]benzazepine-10-carboxamide, 13-cyclohexyl-6-[4-(dimethylamino)-2-pyrimidinyl]-N-[(dimethylamino)sulfonyl]-3-methoxy-. 1H NMR (500 MHz, CHLOROFORM-D) δ ppm 1.14-2.12 (m, 10 H) 2.90 (m, 1 H) 3.06 (s, 6 H) 3.72 (br s, 3 H) 3.83 (br s, 3 H) 3.91 (s, 3 H) 4.19 (br d, 1 H) 6.15 (br d, 1 H) 6.70 (s, 1 H) 6.72 (m, 1 H) 6.90 (s, 1 H) 7.07 (m, 2 H) 7.56 (d, 1 H) 7.81 (d, 1 H) 7.90 (d, 1 H) 8.43 (s, 1 H). LCMS: m/e 615 (M+H).

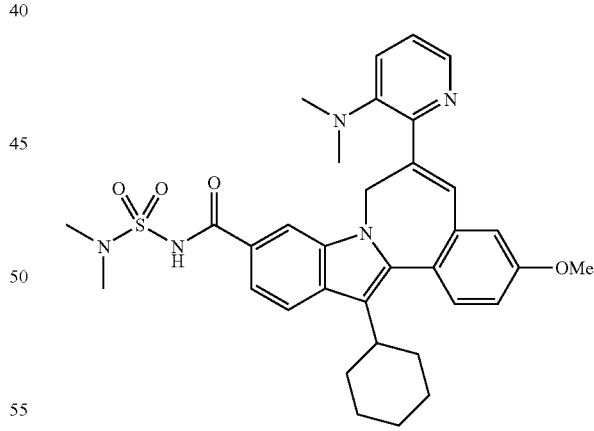

7H-indolo[2,1-a][2]benzazepine-10-carboxamide, 13-cyclohexyl-6-[3-(dimethylamino)-2-pyridinyl]-N-[(dimethylamino)sulfonyl]-3-methoxy-. 1H NMR (500 MHz, CHLOROFORM-D) δ ppm 1.17-2.11 (m, 10 H) 2.88 (m, 1 H) 3.04 (s, 6 H) 3.30 (br s, 3 H) 3.69 (br s, 3 H) 3.95 (s, 3 H) 4.40 (br d, 1 H) 5.95 (br d, 1 H) 6.52 (d, 1 H) 7.14 (dd, 1 H) 7.20 (s, 1 H) 7.32 (m, 1 H) 7.52 (d, 1 H) 7.90 (d, 1 H) 8.29 (d, 1 H) 8.30 (m, 1 H) 8.51 (s, 1 H). LCMS: m/e 614 (M+H).

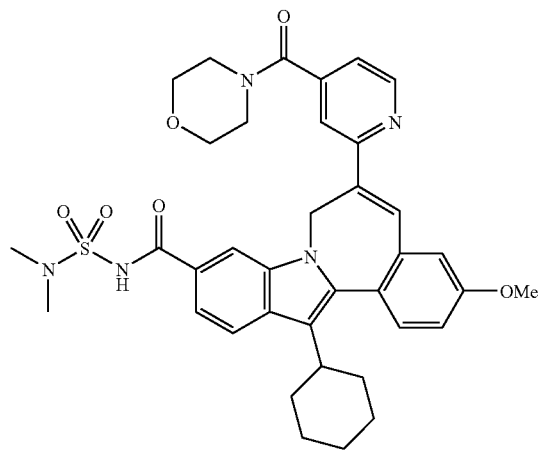

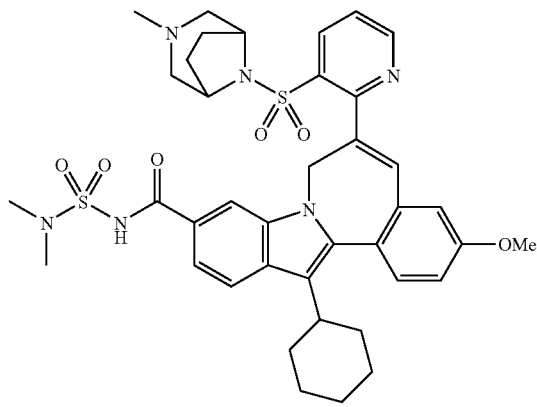

7H-indolo[2,1-a][2]benzazepine-10-carboxamide, 13-cyclohexyl-N-[(dimethylamino)sulfonyl]-3-methoxy-6-[4-(4-morpholinylcarbonyl)-2-pyridinyl]-. 1H NMR (500 MHz, CHLOROFORM-D) δ ppm 1.16-2.13 (m, 10 H) 2.91 (m, 1 H) 3.07 (s, 6 H) 3.43 (m, 2 H) 3.54 (m, 2 H) 3.80 (m, 4 H) 3.92 (s, 3 H) 4.51 (br d, 1 H) 5.92 (br d, 1 H) 7.06 (d, 1 H) 7.12 (dd, 1 H) 7.38 (d, 1 H) 7.56 (d, 1 H) 7.60 (s, 1 H) 7.79 (m, 2 H) 7.90 (d, 1 H) 8.39 (s, 1 H) 8.90 (d, 1 H). LCMS: m/e 684 (M+H).

7H-indolo[2,1-a][2]benzazepine-10-carboxamide, 13-cyclohexyl-N-[(dimethylamino)sulfonyl]-3-methoxy-6-[3-[(3-methyl-3,8-diazabicyclo[3.2.1]oct-8-yl)sulfonyl]-2-pyridinyl]-. 1H NMR (500 MHz, CHLOROFORM-D) δ ppm 1.16-2.13 (m, 13 H) 2.30 (m, 1 H) 2.43 (m, 1 H) 2.81 (s, 3 H) 2.89-3.12 (m, 3 H) 3.06 (s, 6 H) 3.32 (m, 2 H) 3.67 (m, 1 H) 3.89 (s, 3 H) 4.50 (br d, 1H) 6.02 (br d, 1 H) 6.93 (d, 1 H) 7.07 (dd, 1 H) 7.20 (s, 1 H) 7.35 (m, 2 H) 7.52 (d, 1 H) 7.58 (m, 1 H) 7.88 (m, 2 H) 8.75 (d, 1 H). LCMS: m/e 759 (M+H).

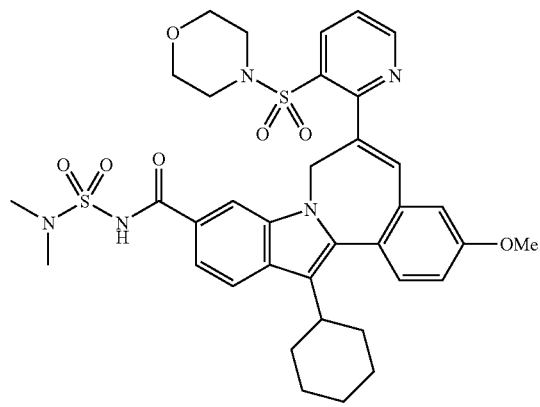

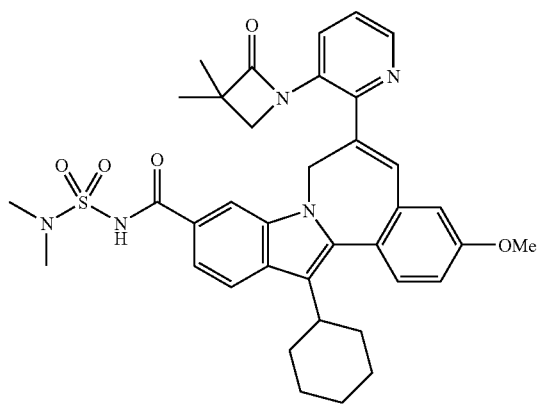

7H-indolo[2,1-a][2]benzazepine-10-carboxamide, 13-cyclohexyl-N-[(dimethylamino)sulfonyl]-3-methoxy-6-[3-(4-morpholinylsulfonyl)-2-pyridinyl]-. 1H NMR (500 MHz, CHLOROFORM-D) δ ppm 1.14-2.13 (m, 10 H) 2.51 (m, 4 H) 2.91 (m, 1 H) 3.03 (s, 6 H) 3.24 (m, 4 H) 3.88 (s, 3 H) 4.65 (br d, 1 H) 5.47 (br d, 1 H) 6.91 (d, 1 H) 7.05 (dd, 1 H) 7.30 (s, 1 H) 7.47 (m, 1 H) 7.53 (d, 1 H) 7.71 (d, 1 H) 7.88 (d, 1 H) 8.02 (s, 1 H) 8.40 (d, 1 H) 8.87 (d, 1 H). LCMS: m/e 720 (M+H).

7H-indolo[2,1-a][2]benzazepine-10-carboxamide, 13-cyclohexyl-N-[(dimethylamino)sulfonyl]-6-[3-(3,3-dimethyl-2-oxo-1-azetidinyl)-2-pyridinyl]-3-methoxy-. 1H NMR (500 MHz, CHLOROFORM-D) δ ppm 0.86 (br s, 3 h) 1.10 (br s, 3 H) 1.13-2.16 (m, 11 H) 2.79 (m, 1 H) 2.92 (m, 1 H) 3.92 (s, 3 H) 4.63 (br d, 1 H) 5.45 (br d, 1 H) 6.77 (s, 1 H) 6.91 (d, 1 H) 7.11 (dd, 1 H) 7.25 (m, 1 H) 7.35 (m, 1 H) 7.52 (d, 1 H) 7.89 (m, 2 H) 8.28 (d, 1 H) 8.52 (d, 1 H). LCMS: m/e 668 (M+H).

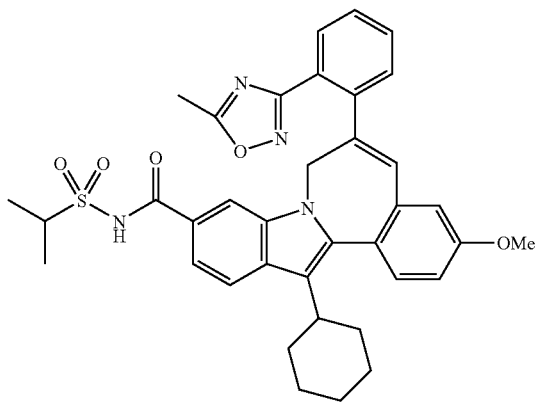

7H-indolo[2,1-a][2]benzazepine-10-carboxamide, 13-cyclohexyl-3-methoxy-N-[(1-methylethyl)sulfonyl]-6-[2-(5-methyl-1,2,4-oxadiazol-3-yl)phenyl]-. 7H-indolo[2,1-a][2]benzazepine-10-carboxylic acid, 13-cyclohexyl-3-methoxy-6-[2-(5-methyl-1,2,4-oxadiazol-3-yl)phenyl]-(90 mg, 0.17 mmol) was dissolved in THF (1.65 mL) and carbonyldiimidazole (107 mg, 0.66 mmol) was added. The resulting solution was stirred at 22° C. under a nitrogen atmosphere for 1.5 hrs then heated to reflux for 1 hr. Upon cooling to room temperature under a nitrogen atmosphere, propane-2-sulfonamide (122 mg, 0.99 mmol) and DBU (75 mg, 0.50 mmol) were added. The reaction was heated to reflux for 1 hr and stirred at 22° C. for 18 hr. 1M HCl (25 mL) was added and the aqueous layer was extracted with CHCl$_3$ (2×25 mL). The organic phase was concentrated under reduced pressure and purified by prep HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. This afforded the title compound (66 mg, 61%) as a yellow paste. 1H NMR (500 MHz, CHLOROFORM-D) δ ppm 1.15-2.14 (m, 16 H) 2.20 (s, 3 H) 2.93 (m, 1 H) 3.91 (s, 3 H) 4.04 (m, 1 H) 4.61 (br d, 1 H) 4.76 (br d, 1 H) 6.72 (s, 1 H) 6.94 (d, 1 H) 7.02 (dd, 1 H) 7.22 (m, 1 H) 7.48 (m, 4 H) 7.91 (m, 2 H) 8.58 (s, 1 H). LCMS: m/e 651 (M+H).

The following compounds were synthesized by an analogous method as described above for 7H-indolo[2,1-a][2]benzazepine-10-carboxamide, 13-cyclohexyl-3-methoxy-N-[(1-methylethyl)sulfonyl]-6-[2-(5-methyl-1,2,4-oxadiazol-3-yl)phenyl]-:

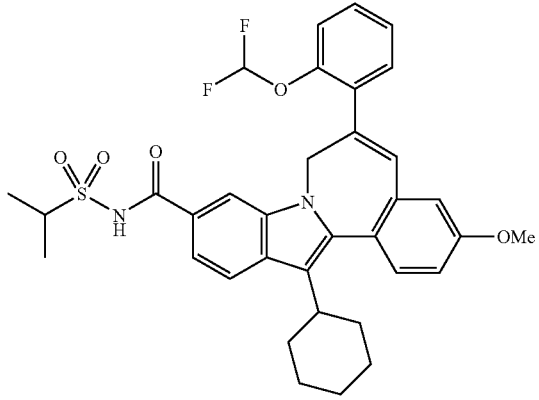

7H-indolo[2,1-a][2]benzazepine-10-carboxamide, 13-cyclohexyl-6-[2-difluoromethoxy)phenyl]-3-methoxy-N-[(1-methylethyl)sulfonyl]-. 1H NMR (500 MHz, CHLOROFORM-D) δ ppm 1.17-2.13 (m, 16 H) 2.90 (m, 1 H) 3.91 (s, 3 H) 4.05 (m, 1 H) 4.60 (br d, 1 H) 5.19 (br d, 1 H) 6.30 (t, 1 H) 6.83 (s, 1 H) 6.95 (d, 1 H) 7.05 (dd, 1 H) 7.21 (m, 3 H) 7.38 (m, 2 H) 7.52 (d, 1 H) 7.90 (m, 2 H). LCMS: m/e 635 (M+H).

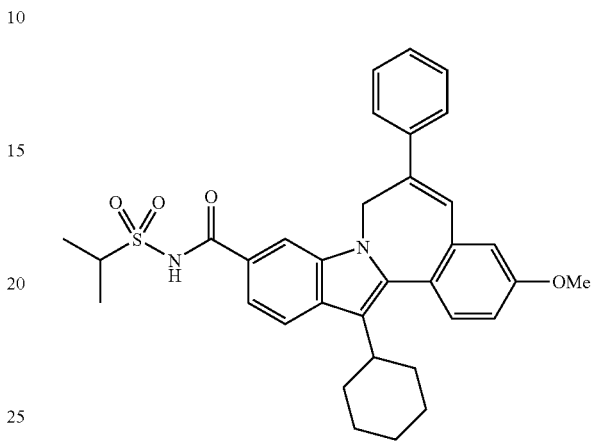

7H-indolo[2,1-a][2]benzazepine-10-carboxamide, 13-cyclohexyl-3-methoxy-N-[(1-methylethyl)sulfonyl]-6-phenyl-. 1H NMR (500 MHz, CHLOROFORM-D) δ ppm 1.17-2.15 (m, 16 H) 2.91 (m, 1 H) 3.92 (s, 3 H) 4.02 (m, 1 H) 4.52 (br d, 1 H) 5.89 (br d, 1 H) 6.99 (dd, 1 H) 7.05 (m, 1 H) 7.33 (m, 2 H) 7.41 (m, 2 H) 7.52 (m, 3 H) 7.91 (d, 1 H) 8.05 (s, 1 H) 8.38 (s, 1 H). LCMS: m/e 569 (M+H).

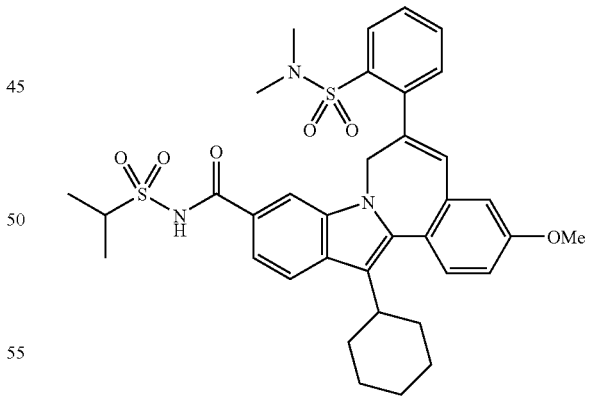

7H-indolo[2,1-a][2]benzazepine-10-carboxamide, 13-cyclohexyl-6-[2-[(dimethylamino)sulfonyl]phenyl]-3-methoxy-N-[(1-methylethyl)sulfonyl]-. 1H NMR (500 MHz, CHLOROFORM-D) δ ppm 1.18-2.13 (m, 16 H) 2.73 (br s, 6 H) 2.91 (m, 1 H) 3.90 (s, 3 H) 4.06 (m, 1 H) 4.70 (br d, 1 H) 5.00 (br d, 1 H) 6.87 (s, 1 H) 6.93 (br d, 1 H) 7.03 (dd, 1 H) 7.35-7.51 (m, 4 H) 7.70 (s, 1 H) 7.93 (m, 2 H) 8.17 (s, 1 H). LCMS: m/e 676 (M+H).

85

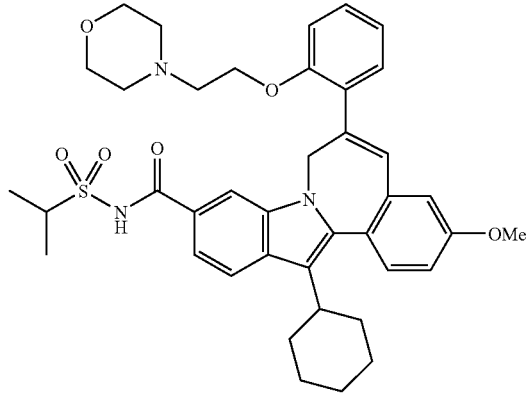

7H-indolo[2,1-a][2]benzazepine-10-carboxamide, 13-cyclohexyl-3-methoxy-N-[(1-methylethyl)sulfonyl]-6-[2-(4-morpholinyl)-5-(trifluoromethyl)phenyl]-. 1H NMR (500 MHz, CHLOROFORM-D) δ ppm 1.12-2.10 (m, 16 H) 2.35 (m, 1 H) 2.83 (m, 2 H) 3.15-3.81 (m, 6 H) 3.93 (s, 3 H) 4.02 (m, 1 H) 5.05 (d, 1 H) 5.55 (d, 1 H) 6.30 (d, 1 H) 6.36 (s, 1 H) 6.77 (m, 2 H) 6.88 (dd, 1 H) 7.40 (m, 2 H) 7.52 (s, 1 H) 7.61 (d, 1 H) 7.80 (s, 1 H). LCMS: m/e 722 (M+H).

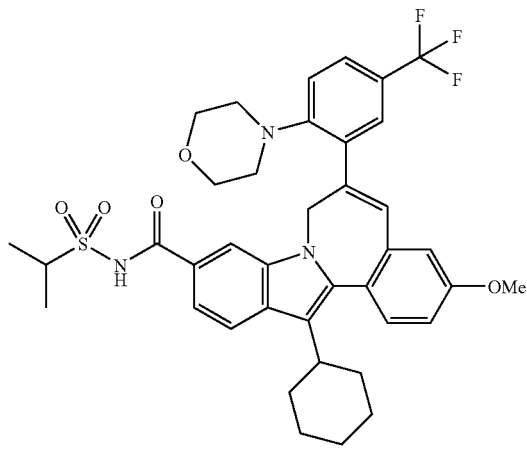

7H-indolo[2,1-a][2]benzazepine-10-carboxamide, 13-cyclohexyl-6-[2-[(cyclopropylcarbonyl)amino]phenyl]-3-methoxy-N-[(1-methylethyl)sulfonyl]-. 1H NMR (500 MHz, CHLOROFORM-D) δ ppm 0.29-1.10 (m, 4 H) 1.13-2.16 (m, 16 H) 2.51 (m, 1 H) 2.74 (m, 1 H) 3.92 (s, 3 H) 4.07 (m, 1 H) 4.22 (d, 1 H) 4.65 (br d, 1 H) 5.46 (br d, 1 H) 6.77 (m, 2 H) 6.93 (d, 1 H) 7.10 (dd, 1 H) 7.25 (m, 1 H) 7.36 (m, 1 H) 7.54 (d, 1 H) 7.88 (m, 2 H) 8.27 (d, 1 H) 8.50 (d, 1 H). LCMS: m/e 652 (M+H).

86

7H-indolo[2,1-a][2]benzazepine-10-carboxamide, 13-cyclohexyl-3-methoxy-N-[(1-methylethyl)sulfonyl]-6-[2-[2-(4-morpholinyl)ethoxy]phenyl]-. 1H NMR (500 MHz, CHLOROFORM-D) δ ppm 1.20-2.21 (m, 16 H) 2.40 (m, 1 H) 2.82 (m, 1 H) 3.00 (m, 3 H) 3.47 (m, 3 H) 3.63 (m, 3 H) 3.92 (s, 3 H) 4.03 (m, 1 H) 4.27 (m, 2 H) 4.49 (br d, 1 H) 5.00 (br d, 1 H) 6.78 (s, 1 H) 6.88 (dd, 1 H) 6.93 (d, 1 H) 7.04 (m, 2 H) 7.33 (m, 1 H) 7.41 (m, 1 H) 7.51 (d, 1 H) 7.98 (m, 3 H). LCMS: m/e 698 (M+H).

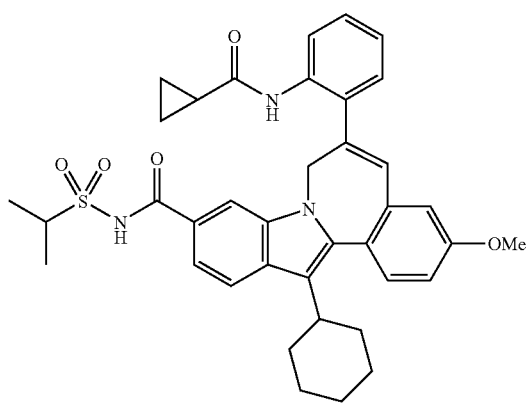

7H-indolo[2,1-a][2]benzazepine-10-carboxamide, 13-cyclohexyl-6-[2-[2-(dimethylamino)ethoxy]phenyl]-3-methoxy-N-[(1-methylethyl)sulfonyl]-. 1H NMR (500 MHz, CHLOROFORM-D) δ ppm 1.20-2.40 (m, 22 H) 2.92 (m, 2 H) 3.50 (m, 1 H) 3.92 (s, 3 H) 4.05 (m, 1 H) 4.21 (m, 2 H) 4.49 (br d, 1 H) 5.00 (br d, 1 H) 6.75 (s, 1 H) 6.87 (dd, 1 H) 6.93 (d, 1 H) 7.04 (m, 2 H) 7.25 (m, 1 H) 7.33 (m, 1 H) 7.41 (m, 1 H) 7.51 (d, 1 H) 8.00 (m, 2 H). LCMS: m/e 656 (M+H).

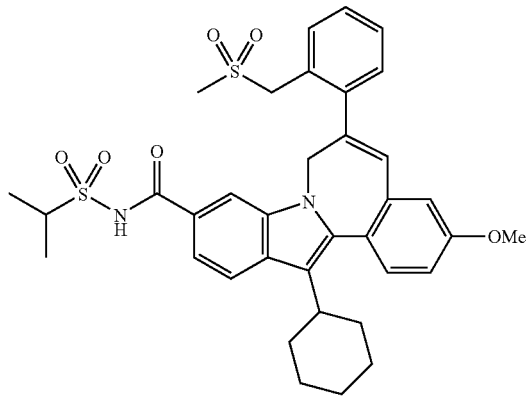

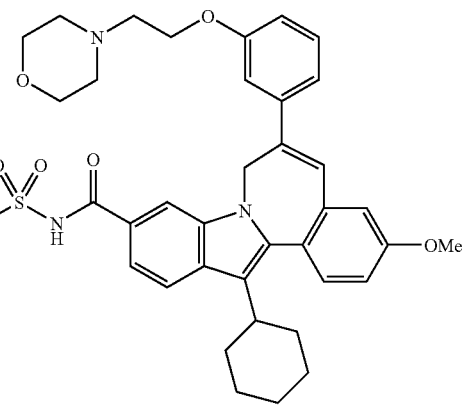

7H-indolo[2,1-a][2]benzazepine-10-carboxamide, 13-cyclohexyl-3-methoxy-N-[(1-methylethyl)sulfonyl]-6-[2-[(methylsulfonyl)methyl]phenyl]-. 1H NMR (500 MHz, CHLOROFORM-D) δ ppm 1.18-2.21 (m, 16 H) 2.45 (br s, 3 H) 2.90 (m, 1 H) 3.60 (br s, 1 H) 3.91 (s, 3 H) 4.03 (m, 1 H) 4.19 (br s, 1 H) 4.62 (br d, 1 H) 5.03 (br d, 1 H) 6.75 (s, 1 H) 6.90 (d, 1 H) 7.04 (dd, 1 H) 7.17 (m, 1 H) 7.36 (m, 2 H) 7.45 (m, 2 H) 7.88 (s, 1 H) 7.92 (m, 2 H). LCMS: m/e 661 (M+H).

7H-indolo[2,1-a][2]benzazepine-10-carboxamide, 13-cyclohexyl-3-methoxy-N-[(1-methylethyl)sulfonyl]-6-[3-[2-(4-morpholinyl)ethoxy]phenyl]-. 1H NMR (500 MHz, CHLOROFORM-D) δ ppm 1.20-2.15 (m, 16 H) 2.90 (m, 1 H) 3.03 (m, 4 H) 3.42 (m, 5 H) 3.92 (s, 3 H) 3.98 (m, 3 H) 4.50 (br d, 1 H) 4.63 (m, 1 H) 5.28 (br d, 1 H) 6.75 (dd, 1 H) 6.95 (m, 2 H) 7.01 (dd, 1 H) 7.20 (m, 2 H) 7.27 (m, 1 H) 7.50 (d, 1 H) 7.69 (d, 1 H) 7.88 (d, 1 H) 8.32 (s, 1 H).LCMS: m/e 698 (M+H).

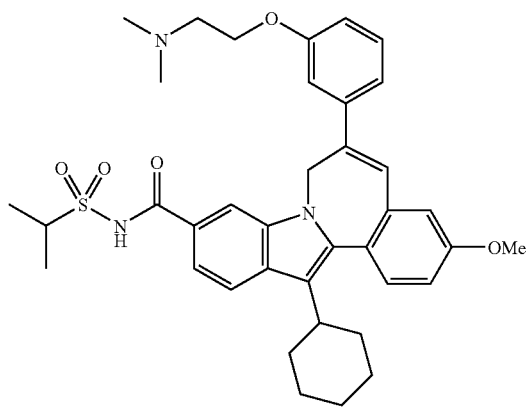

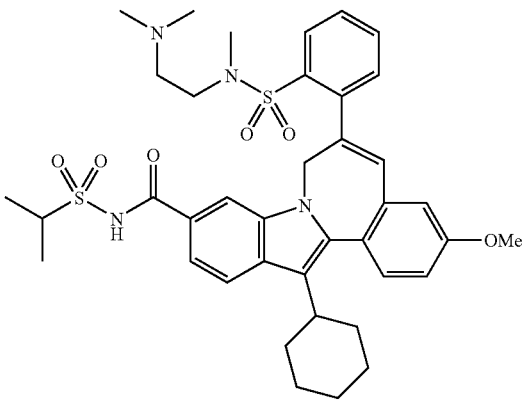

7H-indolo[2,1-a][2]benzazepine-10-carboxamide, 13-cyclohexyl-6-[3-[2-(dimethylamino)ethoxy]phenyl]-3-methoxy-N-[(1-methylethyl)sulfonyl]-. 1H NMR (500 MHz, CHLOROFORM-D) δ ppm 1.17-2.13 (m, 16 H) 2.90 (m, 1 H) 3.00 (br s, 6 H) 3.60 (m, 2 H) 3.92 (s, 3 H) 4.01 (m, 1 H) 4.29 (m, 1 H) 4.49 (br d, 1 H) 4.72 (m, 1 H) 5.45 (br d, 1 H) 6.75 (s, 1 H) 6.87 (dd, 1 H) 6.93 (d, 1 H) 7.04 (m, 2 H) 7.25 (m, 1 H) 7.33 (m, 1 H) 7.41 (m, 1 H) 7.51 (d, 1 H) 7.90 (m, 2 H). LCMS: m/e 656 (M+H).

7H-indolo[2,1-a][2]benzazepine-10-carboxamide, 13-cyclohexyl-6-[2-[[[2-(dimethylamino)ethyl]methylamino]sulfonyl]phenyl]-3-methoxy-N-[(1-methylethyl)sulfonyl]-. 1H NMR (500 MHz, CHLOROFORM-D) δ ppm 1.14-2.16 (m, 16 H) 2.64-3.58 (m, 14 H) 3.91 (s, 3 H) 4.06 (m, 1 H) 4.66 (br d, 1 H) 5.03 (br d, 1 H) 6.76 (m, 1 H) 6.99 (dd, 1 H) 7.04 (m, 2 H) 7.50 (m, 5 H) 7.91 (m, 2 H).LCMS: m/e 733 (M+H).

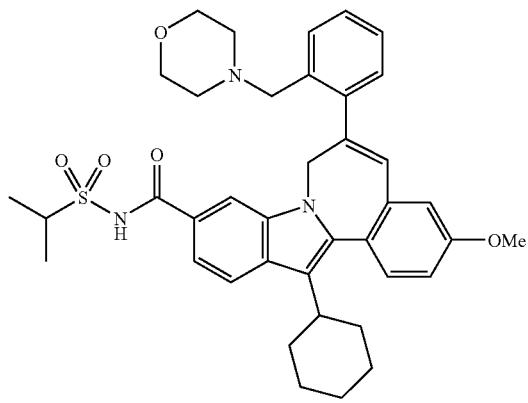

7H-indolo[2,1-a][2]benzazepine-10-carboxamide, 13-cyclohexyl-3-methoxy-N-[(1-methylethyl)sulfonyl]-6-[2-(4-morpholinylmethyl)phenyl]-. 1H NMR (500 MHz, CHLOROFORM-D) δ ppm 1.21-2.19 (m, 16 H) 2.58 (m, 2 H) 2.93 (m, 1 H) 3.11-3.59 (m, 4 H) 3.91 (s, 3 H) 3.95 (m, 4 H) 4.07 (m, 1 H) 4.70 (br d, 1 H) 5.09 (br d, 1 H) 6.63 (s, 1 H) 6.92 (d, 1 H) 7.11 (dd, 1 H) 7.40 (m, 2 H) 7.53 (m, 4 H) 7.72 (s, 1 H) 7.97 (d, 1 H).LCMS: m/e 668 (M+H).

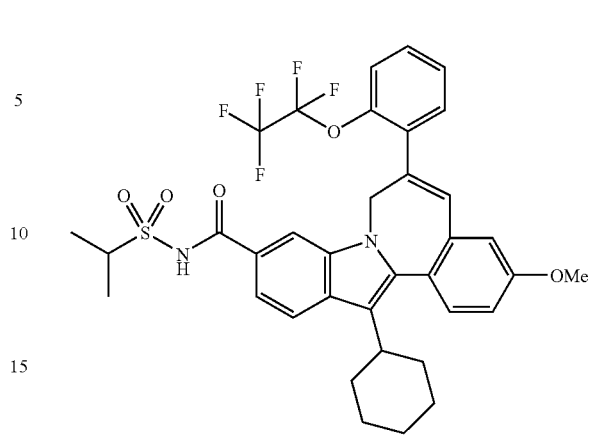

7H-indolo[2,1-a][2]benzazepine-10-carboxamide, 13-cyclohexyl-3-methoxy-N-[(1-methylethyl)sulfonyl]-6-[2-(1,1,2,2-tetrafluoroethoxy)phenyl]-. LCMS: m/e 703 (M+H). retention time 3.08 min.

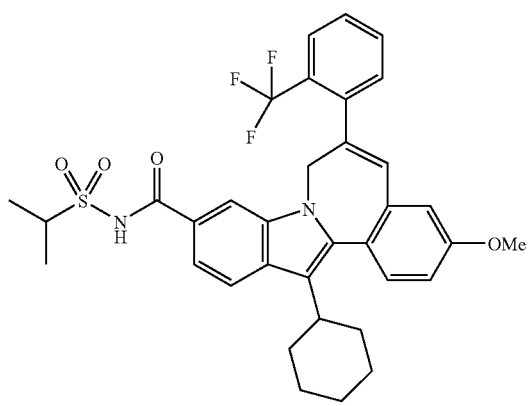

7H-indolo[2,1-a][2]benzazepine-10-carboxamide, 13-cyclohexyl-3-methoxy-N-[(1-methylethyl)sulfonyl]-6-[2-(trifluoromethyl)phenyl]-. LCMS: m/e 637 (M+H). retention time 3.04 min.

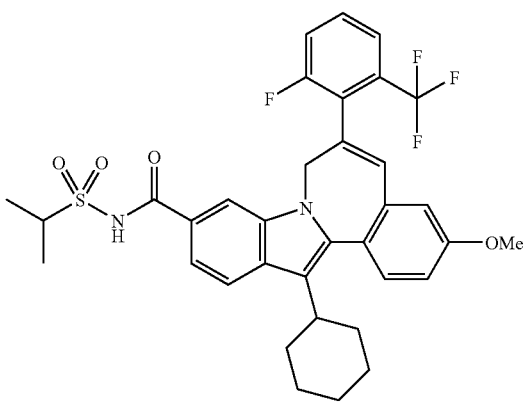

7H-indolo[2,1-a][2]benzazepine-10-carboxamide, 13-cyclohexyl-6-[2-fluoro-6-(trifluoromethyl)phenyl]-3-methoxy-N-[(1-methylethyl)sulfonyl]-. LCMS: m/e 655 (M+H). retention time 3.06 min.

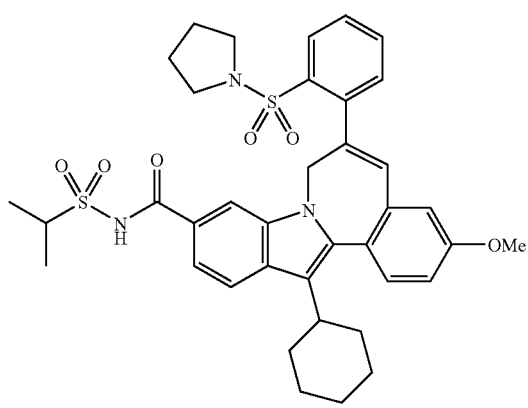

7H-indolo[2,1-a][2]benzazepine-10-carboxamide, 13-cyclohexyl-3-methoxy-N-[(1-methylethyl)sulfonyl]-6-[2-(1-pyrrolidinylsulfonyl)phenyl]-. LCMS: m/e 702 (M+H). retention time 2.98 min.

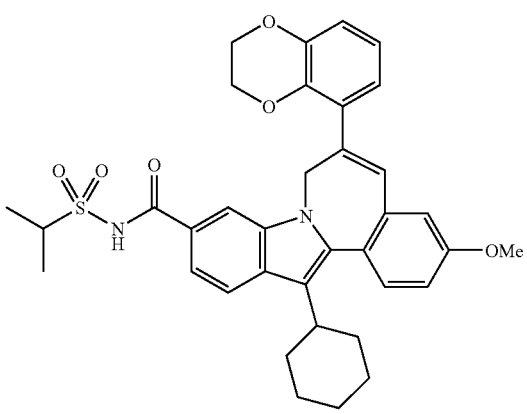

7H-indolo[2,1-a][2]benzazepine-10-carboxamide, 13-cyclohexyl-6-(2,3-dihydro-1,4-benzodioxin-5-yl)-3-methoxy-N-[(1-methylethyl)sulfonyl]-. LCMS: m/e 627 (M+H). retention time 2.99 min.

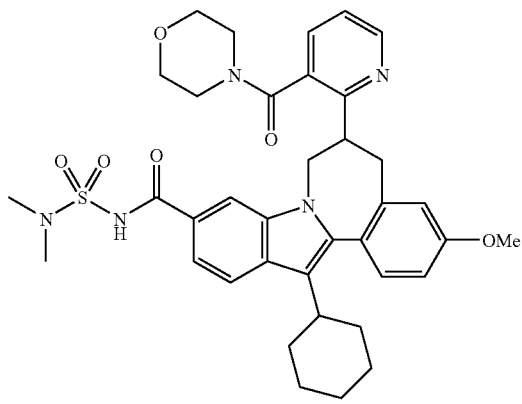

5H-indolo[2,1-a][2]benzazepine-10-carboxamide, 13-cyclohexyl-N-[(dimethylamino)sulfonyl]-6,7-dihydro-3-methoxy-6-[3-(4-morpholinylcarbonyl)-2-pyridinyl]-. To a mixture of 7H-indolo[2,1-a][2]benzazepine-10-carboxamide, 13-cyclohexyl-N-[(dimethylamino)sulfonyl]-3-methoxy-6-[3-(4-morpholinylcarbonyl)-2-pyridinyl]-(10 mg, 0.015 mmol) and 10% Pd/C (10 mg) in isopropanol (2.0 mL) was applied 1 atm of $H_2$ using a balloon. The resulting mixture was allowed to stir at 22° C. for 6 hr, filtered through celite and concentrated under reduced pressure. The resulting yellow solid was purified by prep HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. This afforded the title compound (7.4 mg, 72%) as a white paste. 1H NMR (500 MHz, CHLOROFORM-D) δ ppm 1.14-2.27 (m, 10 H) 2.89-4.05 (m, 13 H) 3.05 (s, 6 H) 3.92 (s, 3 H) 4.70 (m, 1 H) 6.92 (d, 2 H) 7.07-7.70 (m, 3 H) 7.87 (m, 2 H) 8.52 (m, 2 H). MS m/z 686 (MH$^+$).

The following compounds were synthesized by an analogous method as described above for 5H-indolo[2,1-a][2]benzazepine-10-carboxamide, 13-cyclohexyl-N-[(dimethylamino)sulfonyl]-6,7-dihydro-3-methoxy-6-[3-(4-morpholinylcarbonyl)-2-pyridinyl]-:

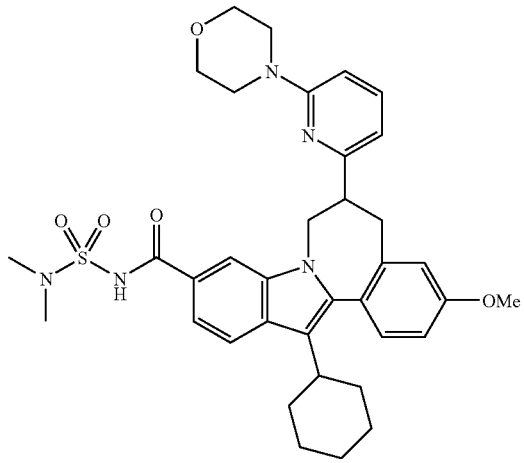

5H-indolo[2,1-a][2]benzazepine-10-carboxamide, 13-cyclohexyl-N-[(dimethylamino)sulfonyl]-6,7-dihydro-3-methoxy-6-[6-(4-morpholinyl)-2-pyridinyl]-. LCMS: m/e 658 (M+H). ret time 2.78 min.

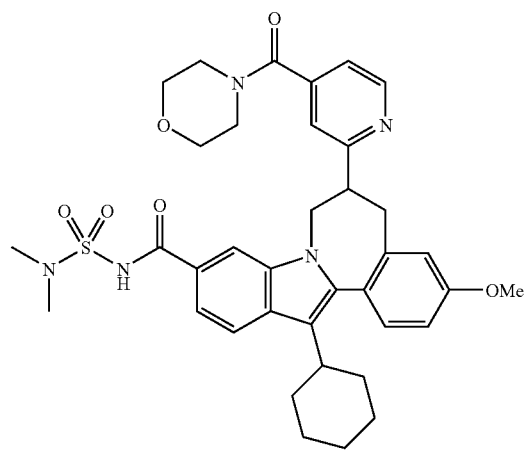

5H-indolo[2,1-a][2]benzazepine-10-carboxamide, 13-cyclohexyl-N-[(dimethylamino)sulfonyl]-6,7-dihydro-3-methoxy-6-[4-(4-morpholinylcarbonyl)-2-pyridinyl]-. LCMS: m/e 686 (M+H). ret time 2.88 min.

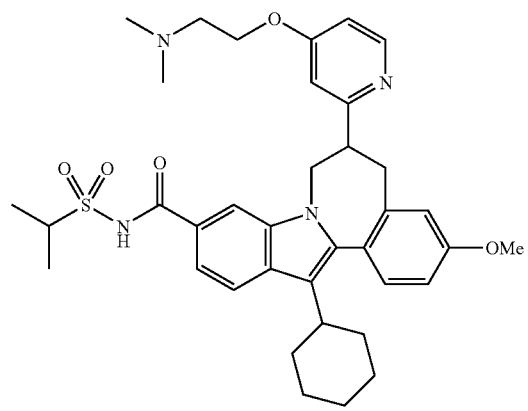

5H-indolo[2,1-a][2]benzazepine-10-carboxamide, 13-cyclohexyl-6-[3-[2-(dimethylamino)ethoxy]phenyl]-6,7-dihydro-3-methoxy-N-[(1-methylethyl)sulfonyl]-. LCMS: m/e 659 (M+H). ret time 2.69 min.

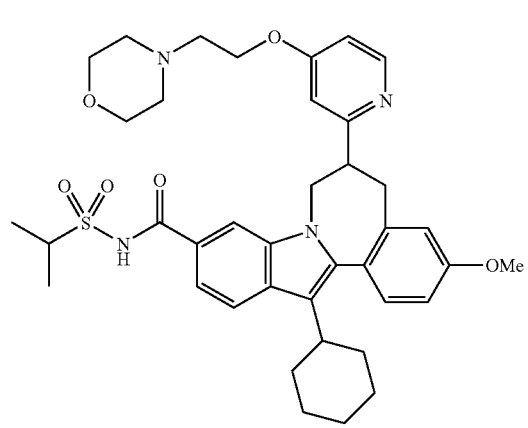

5H-indolo[2,1-a][2]benzazepine-10-carboxamide, 13-cyclohexyl-6,7-dihydro-3-methoxy-N-[(1-methylethyl)sulfonyl]-6-[3-[2-(4-morpholinyl)ethoxy]phenyl]-. LCMS: m/e 701 (M+H). ret time 2.74 min.

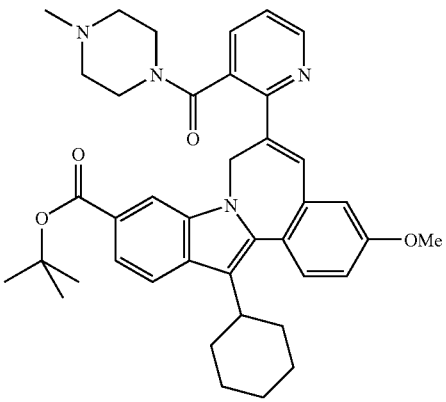

7H-indolo[2,1-a][2]benzazepine-10-carboxylic acid, 13-cyclohexyl-3-methoxy-6-[3-[(4-methyl-1-piperazinyl)carbonyl]-2-pyridinyl]-, 1,1-dimethylethyl ester. 7H-indolo[2,1-a][2]benzazepine-10-carboxylic acid, 13-cyclohexyl-6-[3-(ethoxycarbonyl)-2-pyridinyl]-3-methoxy-, 1,1-dimethylethyl ester (159 mg, 0.269 mmol) was dissolved in a 1:1 solution of THF/MeOH (10 mL) and 1M NaOH (5 mL) was added. The resulting mixture was stirred at 22° C. for 16 hr. 1M HCl (25 mL) was added and the aqueous layer was extracted with CHCl₃ (2×25 mL). The organic phase was dried over Na₂SO₄, filtered, and concentrated under reduced pressure to afford a white solid. This solid was redissolved in THF (1 mL) and carbonyldiimidazole (60 mg, 0.370 mmol) was added. The resulting solution was stirred at 22° C. under a nitrogen atmosphere for 1.5 hrs then heated to reflux for 1 hr. Upon cooling to room temperature under a nitrogen atmosphere, 1-methylpiperazine (62 mg, 0.615 mmol) and DBU (46 mg, 0.370 mmol) were added and the reaction stirred at 22° C. for 18 hr. 1M HCl (10 mL) was added and the aqueous layer was extracted with CHCl₃ (2×25 mL). The organic phase was dried over Na₂SO₄, filtered, and concentrated under reduced pressure to afford the title compound (165 mg, 95%) as a yellow paste. MS m/z 647 (MH⁺).

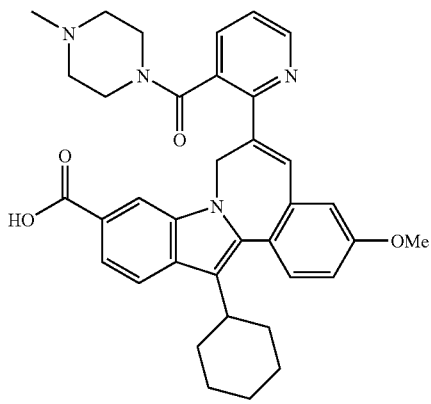

7H-indolo[2,1-a][2]benzazepine-10-carboxylic acid, 13-cyclohexyl-3-methoxy-6-[3-[(4-methyl-1-piperazinyl)carbonyl]-2-pyridinyl]-. 7H-indolo[2,1-a][2]benzazepine-10-carboxylic acid, 13-cyclohexyl-3-methoxy-6-[3-[(4-methyl-1-piperazinyl)carbonyl]-2-pyridinyl]-, 1,1-dimethylethyl ester (61 mg, 0.094 mmol) was dissolved in 1,2-dichloroethane (1 mL) and trifluoroacetic acid (1 mL). The resulting solution was stirred at 22° C. for 3 hr. The solution was concentrated under reduced pressure and purified by prep HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. This afforded the title compound to afford the title compound (36 mg, 64%) as a yellow paste. 1H NMR (500 MHz, CHLOROFORM-D) δ ppm 1.14-2.27 (m, 12 H) 2.55 (br s, 3 H) 2.90-3.30 (m, 6 H) 3.85 (s, 3 H) 4.57 (br d, 1 H) 5.74 (br d, 1 H) 6.88 (d, 1 H) 7.05 (dd, 1 H) 7.21 (m, 1H) 7.32 (m, 1H) 7.50 (d, 1 H) 7.61 (d, 1 H) 7.73 (d, 1 H) 7.84 (d, 1 H) 7.95 (s, 1 H) 8.77 (br d, 1 H). MS m/z 591 (MH⁺) retention time 2.59 min.

The following compounds were synthesized by an analogous method as described above for 7H-indolo[2,1-a][2]benzazepine-10-carboxylic acid, 13-cyclohexyl-3-methoxy-6-[3-[(4-methyl-1-piperazinyl)carbonyl]-2-pyridinyl]-:

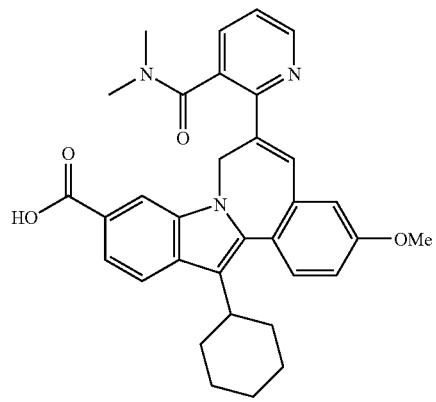

7H-indolo[2,1-a][2]benzazepine-10-carboxylic acid, 13-cyclohexyl-6-[3-[(dimethylamino)carbonyl]-2-pyridinyl]-3-methoxy-. LCMS: m/e 536 (M+H) retention time 2.64 min.

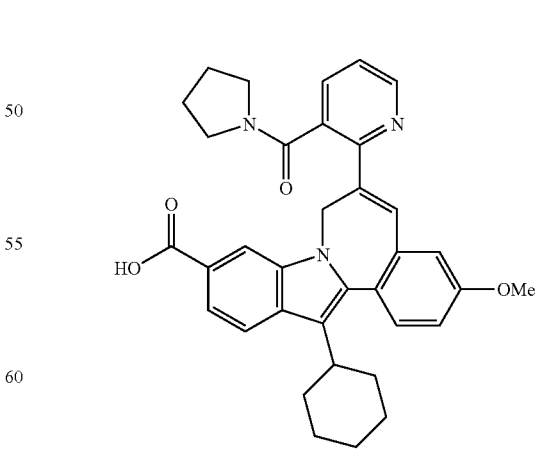

7H-indolo[2,1-a][2]benzazepine-10-carboxylic acid, 13-cyclohexyl-3-methoxy-6-[3-(1-pyrrolidinylcarbonyl)-2-pyridinyl]-. LCMS: m/e 562 (M+H) retention time 2.68 min.

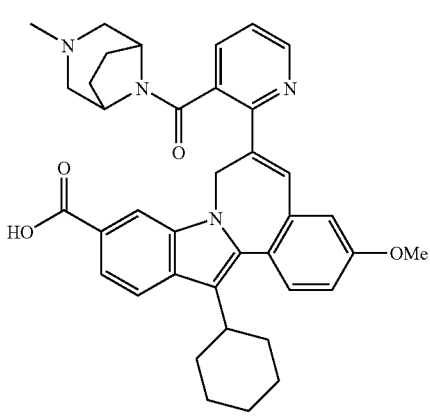

7H-indolo[2,1-a][2]benzazepine-10-carboxylic acid, 13-cyclohexyl-3-methoxy-6-[3-[(3-methyl-3,8-diazabicyclo[3.2.1]oct-8-yl)carbonyl]-2-pyridinyl]-. LCMS: m/e 617 (M+H) retention time 2.61 min.

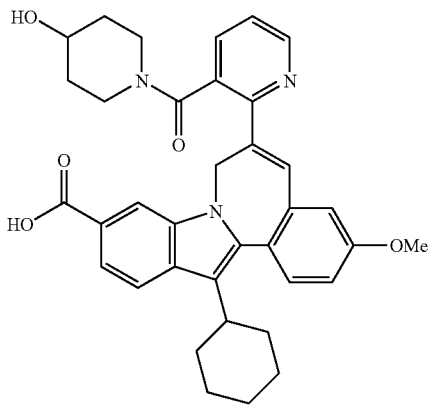

7H-indolo[2,1-a][2]benzazepine-10-carboxylic acid, 13-cyclohexyl-6-[3-[(4-hydroxy-1-piperidinyl)carbonyl]-2-pyridinyl]-3-methoxy-. LCMS: m/e 592 (M+H) retention time 2.64 min.

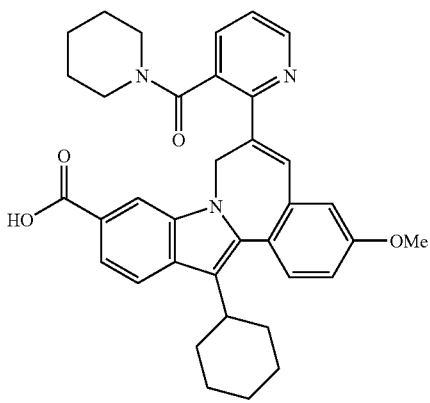

7H-indolo[2,1-a][2]benzazepine-10-carboxylic acid, 13-cyclohexyl-3-methoxy-6-[3-(1-piperidinylcarbonyl)-2-pyridinyl]-. LCMS: m/e 576 (M+H) retention time 2.69 min.

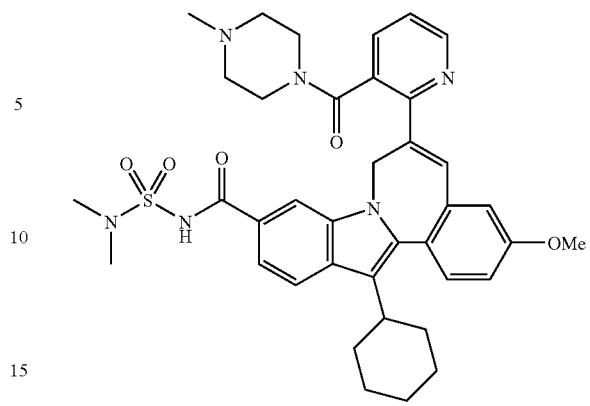

7H-indolo[2,1-a][2]benzazepine-10-carboxamide, 13-cyclohexyl-N-[(dimethylamino)sulfonyl]-3-methoxy-6-[3-[(4-methyl-1-piperazinyl)carbonyl]-2-pyridinyl]-. 7H-indolo[2,1-a][2]benzazepine-10-carboxylic acid, 13-cyclohexyl-3-methoxy-6-[3-[(4-methyl-1-piperazinyl)carbonyl]-2-pyridinyl]-(30 mg, 0.051 mmol) was dissolved in THF (1 mL) and carbonyldiimidazole (23 mg, 0.14 mmol) was added. The resulting solution was stirred at 22° C. under a nitrogen atmosphere for 1.5 hrs then heated to reflux for 1 hr. Upon cooling to room temperature under a nitrogen atmosphere, N,N-dimethylsulfamide (50 mg, 0.33 mmol) and DBU (18 mg, 0.14 mmol) were added. The reaction was heated to reflux for 1 hr and stirred at 22° C. for 18 hr. 1M HCl (10 mL) was added and the aqueous layer was extracted with CHCl₃ (2×25 mL). The organic phase was concentrated under reduced pressure and purified by prep HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. This afforded the title compound (22 mg, 61%) as a yellow paste. 1H NMR (500 MHz, CHLOROFORM-D) δ ppm 1.16-2.24 (m, 18 H) 2.56 (br s, 3 H) 2.89-3.31 (m, 6 H) 3.85 (s, 3 H) 4.01 (m, 1 H) 4.58 (br d, 1 H) 5.76 (br d, 1 H) 6.88 (d, 1 H) 7.07 (dd, 1 H) 7.19 (m, 1 H) 7.33 (m, 1 H) 7.50 (d, 1 H) 7.61 (d, 1 H) 7.73 (d, 1 H) 7.86 (d, 1 H) 7.96 (s, 1 H) 8.78 (br d, 1 H). MS m/z 697 (MH⁺). retention time 2.65 min.

The following compounds were synthesized by an analogous method as described above for 7H-indolo[2,1-a][2]benzazepine-10-carboxamide, 13-cyclohexyl-N-[(dimethylamino)sulfonyl]-3-methoxy-6-[3-[(4-methyl-1-piperazinyl)carbonyl]-2-pyridinyl]-:

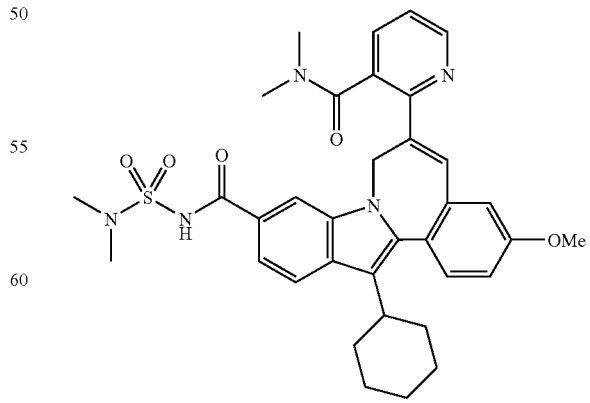

7H-indolo[2,1-a][2]benzazepine-10-carboxamide, 13-cyclohexyl-6-[3-[(dimethylamino)carbonyl]-2-pyridinyl]-N-

[(dimethylamino)sulfonyl]-3-methoxy-. LCMS: m/e 642 (M+H). retention time 2.71 min.

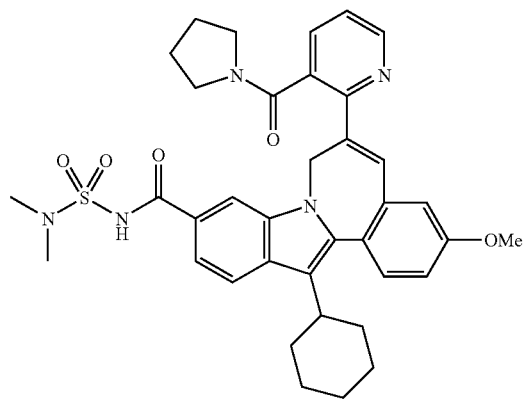

7H-indolo[2,1-a][2]benzazepine-10-carboxamide, 13-cyclohexyl-N-[(dimethylamino)sulfonyl]-3-methoxy-6-[3-(1-pyrrolidinylcarbonyl)-2-pyridinyl]-. LCMS: m/e 668 (M+H). retention time 2.78 min.

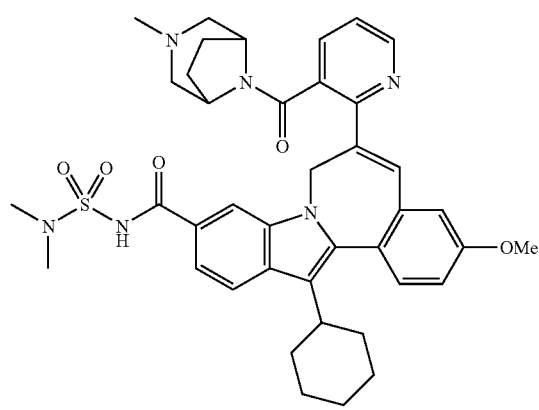

7H-indolo[2,1-a][2]benzazepine-10-carboxamide, 13-cyclohexyl-N-[(dimethylamino)sulfonyl]-3-methoxy-6-[3-[(3-methyl-3,8-diazabicyclo[3.2.1]oct-8-yl)carbonyl]-2-pyridinyl]-. LCMS: m/e 723 (M+H). retention time 2.69 min.

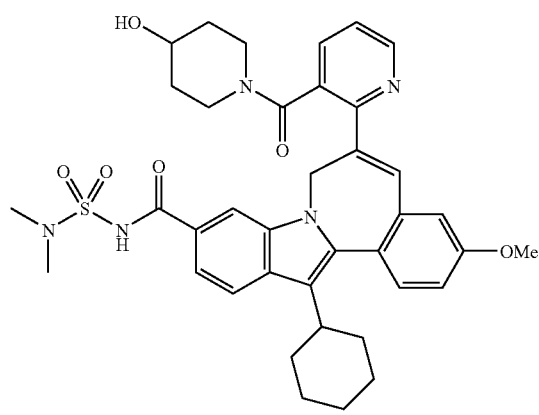

7H-indolo[2,1-a][2]benzazepine-10-carboxamide, 13-cyclohexyl-N-[(dimethylamino)sulfonyl]-6-[3-[(4-hydroxy-1-piperidinyl)carbonyl]-2-pyridinyl]-3-methoxy-. LCMS: m/e 698 (M+H). retention time 2.73 min.

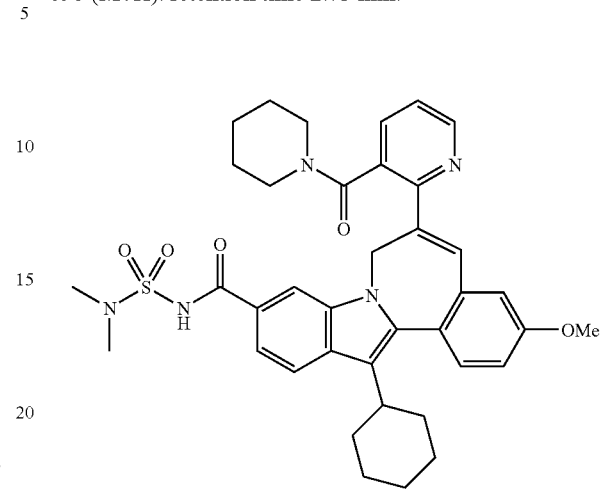

7H-indolo[2,1-a][2]benzazepine-10-carboxamide, 13-cyclohexyl-N-[(dimethylamino)sulfonyl]-3-methoxy-6-[3-(1-piperidinylcarbonyl)-2-pyridinyl]-. LCMS: m/e 682 (M+H). retention time 2.77 min.

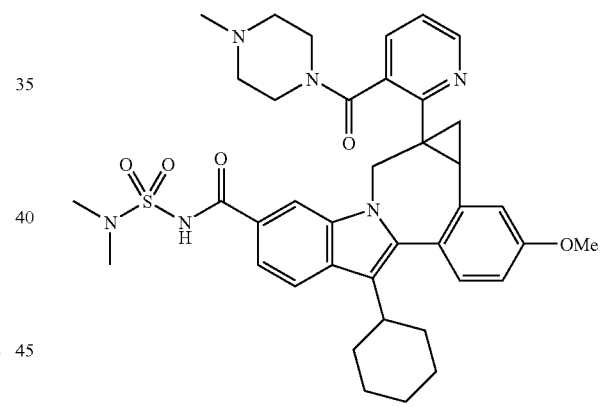

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[3-[(4-methyl-1-piperazinyl)carbonyl]-2-pyridinyl]-. To a solution of trimethylsulfoxonium iodide (20 mg, 0.092 mmol) in DMSO (1.0 mL) was added 90% NaH (2.5 mg, 0.092 mmol). This mixture was stirred at 22° C. for 15 min followed by addition of 7H-indolo[2,1-a][2]benzazepine-10-carboxamide, 13-cyclohexyl-N-[(dimethylamino)sulfonyl]-3-methoxy-6-[3-[(4-methyl-1-piperazinyl)carbonyl]-2-pyridinyl]-(16 mg, 0.023 mmol) in DMSO (1.0 mL). The resulting solution was stirred at 60° C. for 3 hr; 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC as above to afford the title compound (11 mg, 67%) as a yellow paste. MS m/z 711 (MH$^+$). retention time 2.76 min.

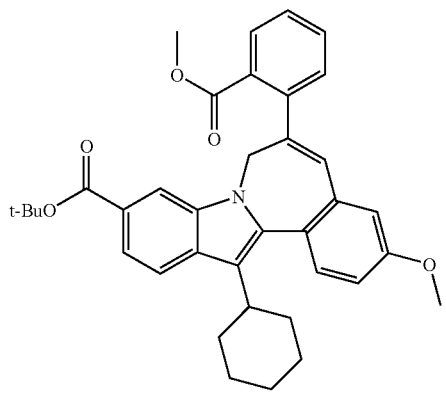

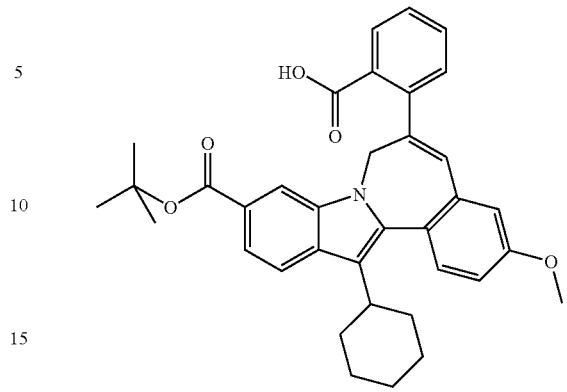

7H-indolo[2,1-a][2]benzazepine-10-carboxylic acid, 13-cyclohexyl-3-methoxy-6-[2-(methoxycarbonyl)phenyl]-, 1,1-dimethylethyl ester. 7H-indolo[2,1-a][2]benzazepine-10-carboxylic acid, 13-cyclohexyl-3-methoxy-6-(tributylstannyl)-, 1,1-dimethylethyl ester (520 mg, 0.710 mmol) was dissolved in 1,4-dioxane (6.8 ml) in a 20 ml microwave vessel with magnetic stir bar. To the reaction was added methyl 2-bromobenzoate (0.189 ml, 1.349 mmol) followed by bis(triphenylphosphine)palladium(II) chloride (35.7 mg, 0.051 mmol). The reaction was capped under a nitrogen atmosphere and immersed in a oil bath (60 C) heating to 100 C. The reaction was heated overnight (18 hr) at 100 C, then cooled to room temperature. The reaction was combined with a previous run reaction (0.349 mmol scale) and volatiles removed in vacuuo using a rotary evaporator to obtain approximately 1 g of a dark green oil. Adsorb crude reaction onto silica gel and chromatograph on 40 g of silica gel slurry packed in 40% hexanes/60% dichloromethane. The product was eluted with 40% hexanes in dichloromethane and the column flushed using 30% hexanes in dichloromethane. Pure product fractions were combined and the solvents removed in vacuuo on a rotary evaporator to yield the title compound as a yellow amorphous solid. Drying the title compound in vacuuo at room temperature overnight gave 387 mg (63%). 1H NMR (500 MHz, CHLOROFORM-D) δ ppm 0.92 (t, J=7.32 Hz, 1 H) 1.19-1.30 (m, 2 H) 1.30-1.51 (m, 5 H) 1.52-1.57 (m, 13 H) 1.58-1.72 (m, 3 H) 1.71-1.86 (m, 2 H) 1.86-2.01 (m, 1 H) 2.00-2.18 (m, 3 H) 2.84-2.96 (m, 1 H) 3.66 (s, 3 H) 3.88 (s, 3 H) 4.68 (d, J=11.60 Hz, 1 H) 4.92 (d, J=10.38 Hz, 1 H) 6.60 (s, 1 H) 6.90 (d, J=2.44 Hz, 1 H) 7.00 (dd, J=8.55, 2.44 Hz, 1 H) 7.03-7.07 (m, 1 H) 7.34-7.44 (m, 2 H) 7.51 (d, J=8.54 Hz, 1 H) 7.63 (d, J=8.55 Hz, 1 H) 7.79 (s, 1 H) 7.82 (d, J=8.55 Hz, 1 H) 7.96-8.04 (m, 1 H). LC-MS retention time 2.9 min; 578 m/z (MH+). LC data was recorded on a Shimadzu LC-10AS liquid chromatograph equipped with a Waters Xterra MS 7 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxylic acid, 6-(2-carboxyphenyl)-13-cyclohexyl-3-methoxy-, 10-(1,1-dimethylethyl) ester. 7H-indolo[2,1-a][2]benzazepine-10-carboxylic acid, 13-cyclohexyl-3-methoxy-6-[2-(methoxycarbonyl)phenyl]-, 1,1-dimethylethyl ester (381 mg, 0.660 mmol) was added to a premixed solution of tetrahydrofuran (4.7 mL), methanol (4.70 mL), and 1.0M sodium hydroxide (4.7 mL, 4.70 mmol). The reaction mixture was an oily heterogeneous mixture and 1,4-dioxane (8 ml) was added to a clear homogeneous mixture. The solution became cloudy after several minutes and an additional dioxane (2 ml) and methanol (1 ml) was added with no apparent effect on solubility state. The reaction was stirred at room temperature under a nitrogen atmosphere overnight (19 hrs). The reaction was concentrated in vacuuo at room temperature (21 C) and the reaction partitioned between ethyl acetate and 1.0N aqueous hydrochloric acid. Ethyl acetate was added to bring the total organic volume to approximately 100 ml to achieve complete solubility. The aqueous phase was extracted with ethyl acetate and the organic phases combined and washed 1N aqueous hydrochloric acid and brine. The organic layer was dried over magnesium sulfate and the volatiles were removed in vacuuo to yield a yellow film. To remove trace water and ethyl acetate the sample was dissolved in dichloromethane and volatiles removed in vacuo using a rotary evaporator. The residue was then dissolved in benzene and the volatiles removed in vacuo to yield a yellow foam/film when dried in vacuo at room temperature yielded 382 mg of the crude product as a yellow amorphous solid. LC-MS retention time 2.19 min; 562 m/z (MH−). LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

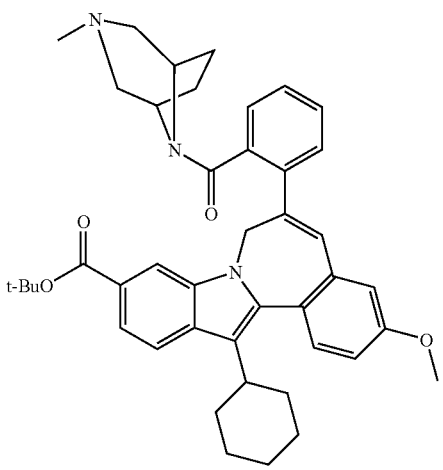

7H-indolo[2,1-a][2]benzazepine-10-carboxylic acid, 13-cyclohexyl-3-methoxy-6-[2-[(3-methyl-3,8-diazabicyclo[3.2.1]oct-8-yl)carbonyl]phenyl]-, 1,1-dimethylethyl ester. 7H-indolo[2,1-a][2]benzazepine-10-carboxylic acid, 6-(2-carboxyphenyl)-13-cyclohexyl-3-methoxy-, 10-(1,1-dimethylethyl) ester (192 mg, 0.341 mmol) was dissolved in DMF (3.4 ml) and add TBTU (208 mg, 0.647 mmol) to the reaction. The reaction was capped under a nitrogen atmosphere and stirred at room temperature for 1 hour then DMAP (214 mg, 1.752 mmol) was dissolved. The amine reagent, 3-methyl-3,8-diazabicyclo[3.2.1]octane dihydrochloride (148 mg, 0.743 mmol) was added to the reaction and the reaction was capped under a nitrogen atmosphere and stirred at room temperature overnight. The reaction was diluted with ethyl acetate and washed sequentially with 1.0N aqueous hydrochloric acid, saturated aqueous sodium bicarbonate and brine. The organic phase was dried over MgSO4, filtered and solvent removed in vacuuo. The crude product weighed 214 mg as a yellow solid after drying in vacuuo at room temperature. The product was purified on a 7 g silica gel column slurried in a solvent of 1% methanol/dichloromethane. Product fractions were combined and solvent removed in vacuuo to yield 161 mg of product as a yellow solid. HPLC analysis indicated further purification would be desired therefore the enriched product was dissolved in 4 ml DMF/acetonitrile mixture and purified by reverse phase HPLC: Typical HPLC conditions: Shimadzu high pressure liquid chromatography system employing Discovery VP software interfaced with a SCL-10A controller, SIL-10A autosampler and FRC-10A fraction collector and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 30 minutes using % A=10% acetonitrile, 90% water, 0.1% TFA % B=90% acetonitrile, 10% water, 0.1% TFA solvent system. Retention time of product=10 min. Solvents were removed from the product fractions in vacuuo using a speed-vac operating overnight using medium heat setting. The pure product fractions were combined and transferred to a vial using dichloromethane, removal of solvent in vacuuo and drying in vacuuo at room temperature yielded 102 mg (38%) of product as a yellow amorphous film. 1H NMR (500 MHz, CHLOROFORM-D) δ ppm 0.85 (m, 1 H) 1.09-1.51 (m, 6 H) 1.60 (s, 10 H) 1.65-1.96 (m, 6 H) 2.05 (s, 3 H) 2.19-2.78 (m, 5 H) 2.91 (t, J=10.99 Hz, 1H) 2.97-3.37 (m, 1 H) 3.38-3.72 (m, 2 H) 3.88 (s, 3 H) 4.20-4.84 (m, 2 H) 5.18 (s, 1 H) 6.88 (d, J=2.14 Hz, 1 H) 6.99 (s, 1 H) 7.03 (dd, J=8.70, 2.59 Hz, 1 H) 7.31-7.46 (m, 3 H) 7.50 (d, J=8.55 Hz, 2 H) 7.67 (d, J=8.24 Hz, 1 H) 7.82 (d, J=8.55 Hz, 1 H) 7.97 (s, 1 H). LC-MS retention time 2.94 min; 672 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

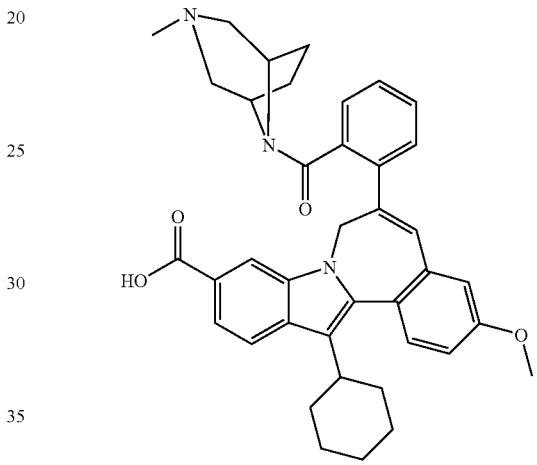

7H-indolo[2,1-a][2]benzazepine-10-carboxylic acid, 13-cyclohexyl-3-methoxy-6-[2-[(3-methyl-3,8-diazabicyclo[3.2.1]oct-8-yl)carbonyl]phenyl]-. Dissolve 7H-indolo[2,1-a][2]benzazepine-10-carboxylic acid, 13-cyclohexyl-3-methoxy-6-[2-[(3-methyl-3,8-diazabicyclo[3.2.1]oct-8-yl)carbonyl]phenyl]-, 1,1-dimethylethyl ester (99 mg, 0.147 mmol) in 1,2-dichloroethane (2 mL), then add TFA (2 mL). Cap the reaction under a nitrogen atmosphere and stir at room temperature for 2.3 hrs. Remove volatiles in vacuuo using a rotary evaporator. Dissolve the reaction residue in a mixture of dichloromethane and benzene then remove the volatiles in vacuuo and repeat dissolution and volatile removal to aid in removal of TFA. The sample was dried in vacuuo at room temperature overnight to obtain 93 mg of the title compound as a beige amorphous solid. The reaction product was carried on without further purification. 1H NMR (500 MHz, CHLOROFORM-D) δ ppm 1.15-1.33 (m, 2 H) 1.34-1.45 (m, 2 H) 1.45-1.74 (m, 3 H) 1.75-1.87 (m, J=9.16 Hz, 2 H) 1.94 (s, 1 H) 2.01-2.17 (m, J=5.80 Hz, 3 H) 2.37-2.72 (m, J=78.43 Hz, 3 H) 2.92 (t, J=12.05 Hz, 1 H) 3.13-3.77 (m, 4 H) 3.90 (s, 3 H) 4.66 (d, J=58.29 Hz, 4 H) 4.94-5.27 (m, 1 H) 6.91 (s, 1 H) 6.97 (s, 1 H) 7.04 (dd, J=8.70, 2.59 Hz, 1 H) 7.40 (d, J=7.63 Hz, 1 H) 7.45 (d, J=8.24 Hz, 2 H) 7.51 (d, J=8.55 Hz, 2H) 7.75 (d, J=5.49 Hz, 1 H) 7.87 (d, J=8.24 Hz, 1 H) 7.93-8.23 (m, 1 H). LC-MS retention time 1.68 min; 614 m/z (MH−). LC data was recorded on a Shimadzu LC-10AS liquid chromatograph equipped with a Waters Xterra MS 7 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

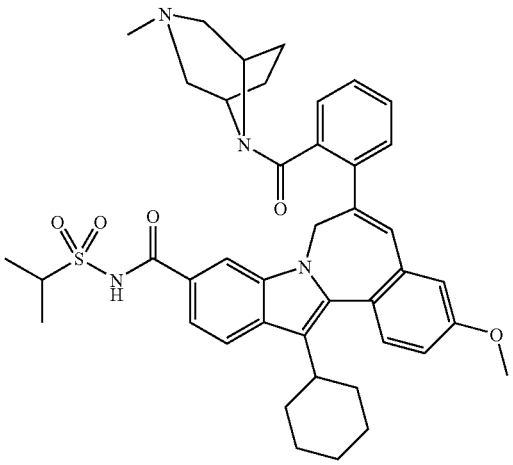

13-cyclohexyl-N-(isopropylsulfonyl)-3-methoxy-6-(2-((3-methyl-3,8-diazabicyclo[3.2.1]oct-8-yl)carbonyl)phenyl)-7H-indolo[2,1-a][2]benzazepine-10-carboxamide. In a 2 dram vial suspend 7H-indolo[2,1-a][2]benzazepine-10-carboxylic acid, 13-cyclohexyl-3-methoxy-6-[2-[(3-methyl-3,8-diazabicyclo[3.2.1]oct-8-yl)carbonyl]phenyl]-(44.5 mg, 0.072 mmol) in THF (725 μl) then add then CDI (30 mg, 0.185 mmol). The reaction was capped under a nitrogen atmosphere and stirred at room temperature for 1 hr. The reaction became a clear homogeneous solution five minutes after the addition of CDI to the reaction suspension. The reaction was then heated to 70 C in the sealed vial for 1 hr. Upon cooling the reaction to room temperature, propane-2-sulfonamide (45 mg, 0.365 mmol) was added to the reaction followed by DBU (32.7 μl, 0.217 mmol). The reaction was again capped under a nitrogen atmosphere and heated to 70 C overnight (16 hr). The reaction was partitioned between ethyl acetate and 1.0N aqueous hydrochloric acid. The organic layer was washed with 1.0N aqueous hydrochloric acid then the combined aqueous layers were back extracted with ethyl acetate. The combined organic layers were washed with brine and dried over magnesium sulfate. The drying agent was removed by filtration and the product obtained by removal of volatiles in vacuuo using a rotary evaporator to obtain 62 mg of crude product as a yellow film. The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1), 2 ml, purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 30 minutes using % A=10% acetonitrile, 90% water, 0.1% TFA % B=90% acetonitrile, 10% water, 0.1% TFA solvent system. Retention time of product was 6.74 minutes. Removal of volatiles and drying the purified product in vacuuo at room temperature yielded 27.7 mg (46%) of the title compound as a amorphous yellow solid. 1H NMR (500 MHz, CHLOROFORM-D) δ ppm 0.36 (s, 0.7 H) 1.06-1.31 (m, 2.6 H) 1.31-1.57 (m, 10.8 H) 1.59-1.71 (m, 1.1 H) 1.79 (d, J=10.07 Hz, 2.7 H) 1.90-2.15 (m, 4.8 H) 2.23 (d, J=11.90 Hz, 1.1 H) 2.35 (s, 0.9 H) 2.57 (s, 2.7 H) 2.63-2.85 (m, 2.6 H) 2.83-2.98 (m, 3.2 H) 3.06 (s, 1.3 H) 3.21 (d, J=11.60 Hz, 1.6 H) 3.34 (d, J=12.21 Hz, 1.1 H) 3.48 (s, 1.3 H) 3.66 (d, J=6.41 Hz, 1.1 H) 3.93 (s, 3.0 H) 4.00-4.17 (m, 1.2 H) 4.45 (s, 0.3 H) 4.62 (d, J=15.26 Hz, 1.0 H) 4.96 (d, J=15.87 Hz, 0.8 H) 5.16 (d, J=14.34 Hz, 0.3 H) 6.94 (d, J=16.48 Hz, 2.0 H) 7.03-7.08 (m, 1.1 H) 7.41 (d, J=7.32 Hz, 1.2 H) 7.46-7.61 (m, 4.2 H) 7.65 (d, J=8.24 Hz, 0.9 H) 7.73 (s, 0.8 H) 7.92 (d, J=8.54 Hz, 1.3 H) 10.05 (s, 0.2 H) 10.22 (s, 0.7 H). LC-MS retention time 1.91 min; 719 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

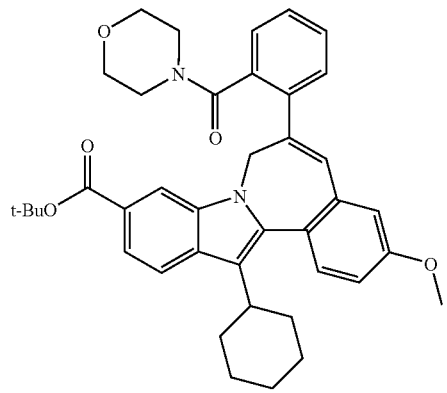

7H-indolo[2,1-a][2]benzazepine-10-carboxylic acid, 13-cyclohexyl-3-methoxy-6-[2-(4-morpholinylcarbonyl) phenyl]-, 1,1-dimethylethyl ester. In a 2 dram vial dissolve 7H-indolo[2,1-a][2]benzazepine-10-carboxylic acid, 6-(2-carboxyphenyl)-13-cyclohexyl-3-methoxy-, 10-(1,1-dimethylethyl) ester (186.6 mg, 0.331 mmol) in DMF (3.3 mL). TBTU (212 mg, 0.660 mmol) was added to the reaction and the reaction was stirred at room temperature under a nitrogen atmosphere for 1 hour. DMAP (214 mg, 1.752 mmol) was dissolved into the reaction then amine reagent, morpholine (115 μL, 1.324 mmol) was added. The reaction was capped under a nitrogen atmosphere and stirred at room temperature overnight. The reaction was diluted with ethyl acetate and washed sequentially with 1.0N aqueous hydrochloric acid, satruated aqueous sodium bicarbonate and brine. The organic phase was dried over MgSO4, filtered and solvent removed in vacuuo to obtain 198 mg of crude product as a yellow film. The crude product was dissolved in 2 ml of acetonitrile and 4 ml of DMF was added to the mixture. The product solution was purified in three 2 ml injection using reverse phase HPLC. The sample was purified on a Shimadzu high pressure liquid chromatography system employing Discovery VP software interfaced with a SCL-10A controller, SIL-10A autosampler and FRC-10A fraction collector. The sample was purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA solvent system. The retention time of the product is 17.6 minutes. The product fractions were combined and volatiles removed in vacuuo using a rotary evaporator. The purified product was transferred to a vial as a dichloromethane solution and solvent removed in vacuuo to yield a 74 mg (35%) of the title compound as a amber-orange amorphous solid. 1H NMR (500 MHz, CHLOROFORM-D) δ ppm 1.17-1.29 (br.s H) 1.31-1.50 (m, 2 H) 1.51-1.67 (m, 10 H) 1.78 (d, J=10.07 Hz, 2 H) 1.94 (d, J=7.93 Hz, 1 H) 2.08 (d, J=16.17 Hz, 4 H) 2.28-2.81 (m, 4 H) 2.83-3.12 (m, 2 H) 3.37 (br.s, 3 H) 3.75 (br.s, 1 H) 3.88 (s, 3 H) 4.59 (d, J=13.43 Hz, 1 H) 5.28 (br.s, 1 H) 6.90 (d, J=2.44 Hz, 1 H) 6.95 (s, 1 H) 7.02 (dd, J=8.55, 2.75 Hz, 1 H) 7.30 (d, J=7.32 Hz, 1 H) 7.35-7.41 (m, 1 H) 7.42-7.54 (m, 3 H) 7.63 (d, J=7.93 Hz, 1 H) 7.78-7.94 (m, 2 H). LC-MS retention time 2.69 min; 633 m/z (MH+). LC data was recorded on a Shimadzu LC-10AS liquid chromatograph equipped with a Waters Xterra MS 7 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

We claim:

1. A compound of formula I

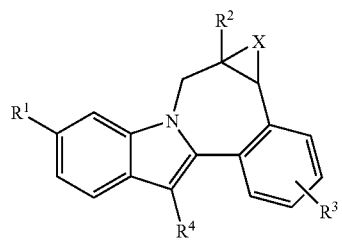

I where:

$R^1$ is $CO_2R^5$ or $CONR^6R^7$;

$R^2$ is pyridinyl, pyrazinyl, pyrimidinyl, or pyridazinyl, and is substituted with 0-1 substituents selected from the group consisting of $(R^5)_2N$, $R^{12}$, $COR^{13}$, and $SO_2R^{14}$;

or $R^2$ is phenyl and is substituted with 0-2 substituents selected from halo, alkyl, alkoxy, and haloalkoxy and is substituted with 0-1 substituents selected from the group consisting of $(R^5)_2N$, $((R^5)_2N)$alkyl$(R^5)N$, $(R^{12})$alkyl$(R^5)N$, alkylCON$(R^5)$, cycloalkylCON$(R^5)$, (methyl)oxadiazolyl, $((R^5)_2N)$alkoxy, $(R^{12})$alkoxy, $R^{12}$, $((R^5)_2N)$alkyl, $(R^{12})$alkyl, $COR^{13}$, (alkylSO$_2$)alkyl, and $SO_2R^{14}$;

or $R^2$ is indolyl, indazolyl, benzimidazolyl, benzotriazolyl, pyrrolopyridinyl, benzoxazolyl, benzothiazolyl, and is substituted with 0-2 substituents selected from halo, alkyl, haloalkyl, nitro, cyano, alkoxy, and haloalkoxy;

or $R^2$ is benzodioxolyl or dihydrobenzodioxinyl, and is substituted with 0-2 substituents selected from halo and alkyl;

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkylSO$_2$, cycloalkylSO$_2$, haloalkylSO$_2$, $(R^9)(R^{10})NSO_2$, or $(R^{11})SO_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, piperazinyl, N-alkylpiperazinyl, morpholinyl, thiomorpholinyl, homopiperidinyl, or homomorpholinyl;

$R^{12}$ is azetidinyl, pyrrolidinyl, piperidinyl, piperazinyl, morpholinyl, thiomorpholinyl, homopiperidinyl, or homomorpholinyl, and is substituted with 0-3 substituents selected from oxo and alkyl;

$R^{13}$ is hydroxy, alkoxy, amino, alkylamino, dialkylamino, azetidinyl, pyrrolidinyl, piperidinyl, hydroxypiperidinyl, piperazinyl, N-alkylpiperazinyl, morpholinyl, thiomorpholinyl, homopiperidinyl, homomorpholinyl,

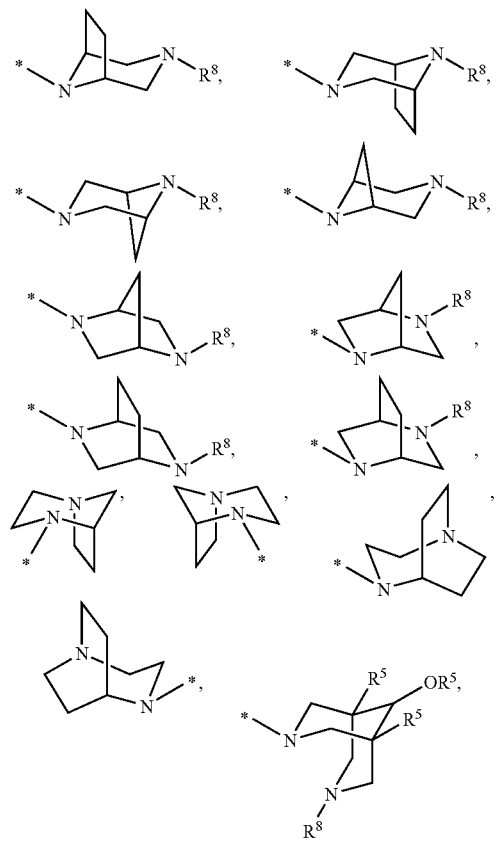

-continued

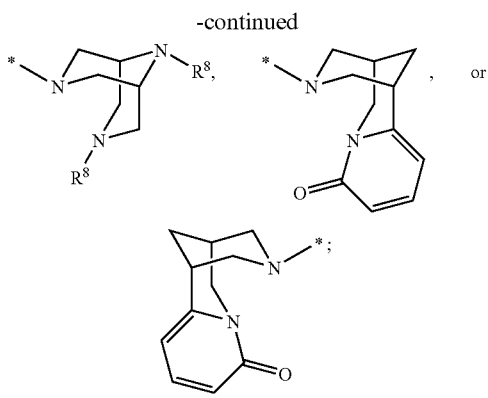

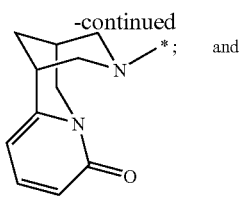

and $R^{14}$ is hydroxy, alkoxy, $(R^5)_2N$, $((R^5)_2N)$alkyl, $((R^5)_2N)$alkyl$(R^5)N$, $(R^{12})$alkyl, $(R^{12})$alkyl$(R^5)N$, azetidinyl, pyrrolidinyl, piperidinyl, hydroxypiperidinyl, piperazinyl, N-alkylpiperazinyl, morpholinyl, thiomorpholinyl, homopiperidinyl, homomorpholinyl,

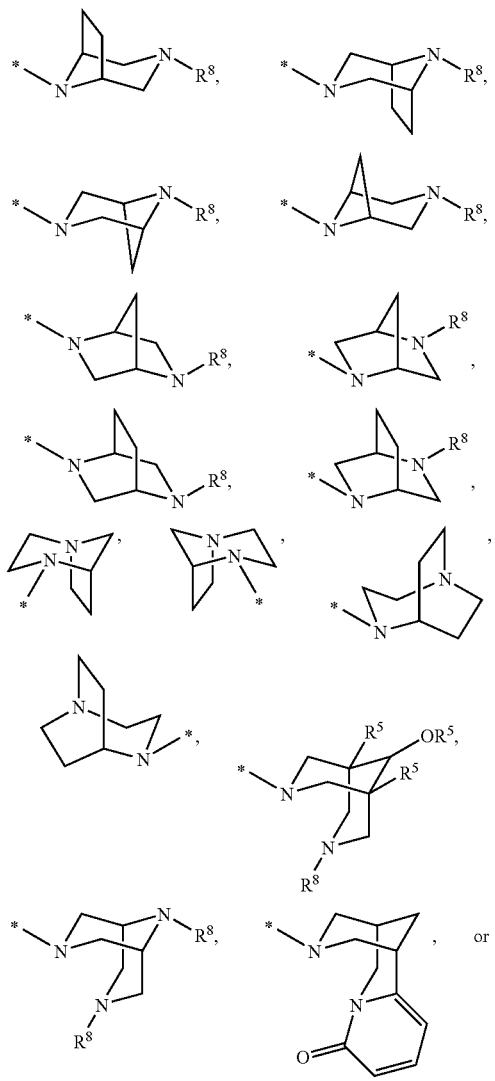

X is methylene, a bond, or absent;
or a pharmaceutically acceptable salt thereof.

2. A compound of claim 1 where
$R^1$ is $CO_2R^5$ or $CONR^6R^7$;
$R^2$ is pyridinyl, pyrazinyl, pyrimidinyl, or pyradazinyl, and is substituted with 0-1 substituents selected from the group consisting of amino, alkylamino, dialkylamino, $R^{12}$, $COR^{13}$, and $SO_2R^{14}$;
or $R^2$ is phenyl and is substituted with 0-2 substituents selected from halo, alkyl, and alkoxy and is substituted with 0-1 substituents selected from the group consisting of amino, alkylamino, dialkylamino, $R^{12}$, $COR^{13}$, and $SO_2R^{14}$;
$R^3$ is hydrogen, halo, alkyl, alkenyl, hydroxy, benzyloxy, or alkoxy;
$R^4$ is cycloalkyl;
$R^5$ is hydrogen or alkyl;
$R^6$ is hydrogen, alkyl, alkylSO$_2$, cycloalkylSO$_2$, haloalkylSO$_2$, $(R^9)(R^{10})NSO_2$, or $(R^{11})SO_2$;
$R^7$ is hydrogen or alkyl;
$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;
$R^9$ is hydrogen or alkyl;
$R^{10}$ is hydrogen or alkyl;
$R^{11}$ is azetidinyl, pyrrolidinyl, piperidinyl, piperazinyl, N-alkylpiperazinyl, morpholinyl, thiomorpholinyl, homopiperidinyl, or homomorpholinyl;
$R^{12}$ is azetidinyl, pyrrolidinyl, piperidinyl, piperazinyl, morpholinyl, thiomorpholinyl, homopiperidinyl, or homomorpholinyl, and is substituted with 0-3 substituents selected from oxo and alkyl;
$R^{13}$ is hydroxy, alkoxy, amino, alkylamino, dialkylamino, azetidinyl, pyrrolidinyl, piperidinyl, hydroxypiperidinyl, piperazinyl, N-alkylpiperazinyl, morpholinyl, thiomorpholinyl, homopiperidinyl, homomorpholinyl,

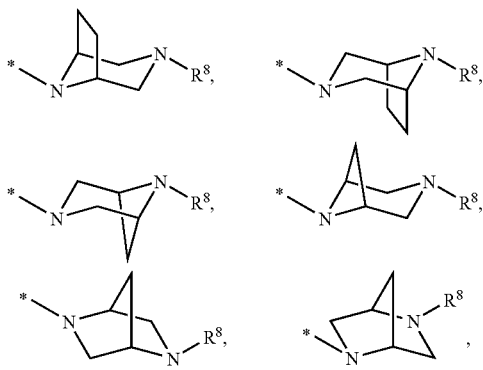

-continued

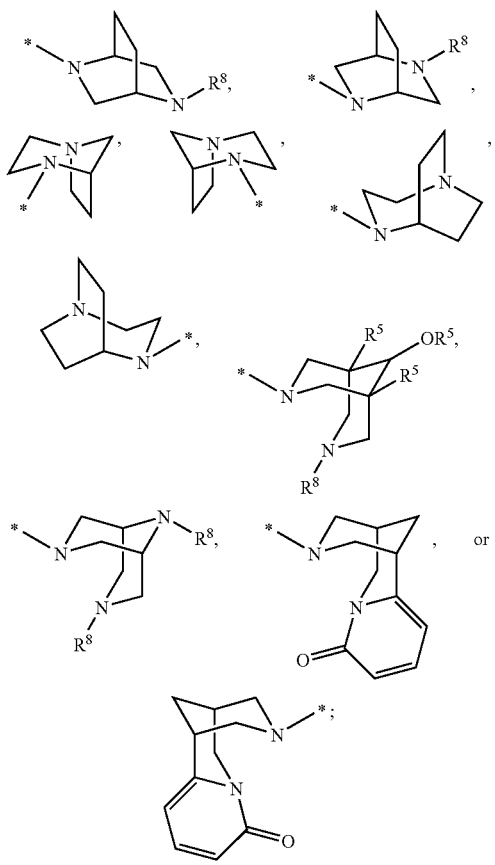

$R^{14}$ is hydroxy, alkoxy, amino, alkylamino, dialkylamino, azetidinyl, pyrrolidinyl, piperidinyl, hydroxypiperidinyl, piperazinyl, N-alkylpiperazinyl, morpholinyl, thiomorpholinyl, homopiperidinyl, homomorpholinyl,

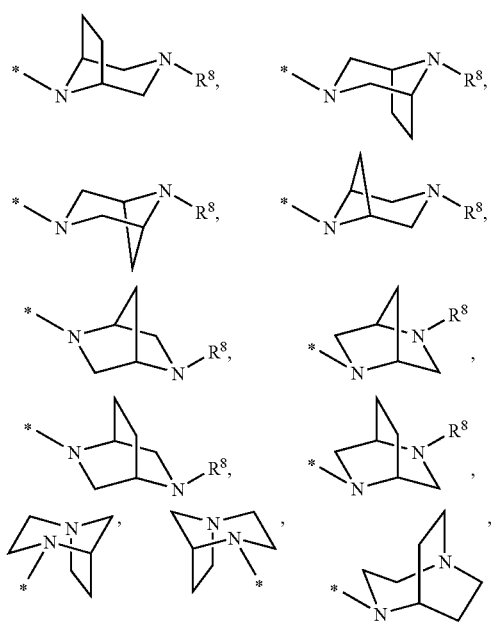

-continued

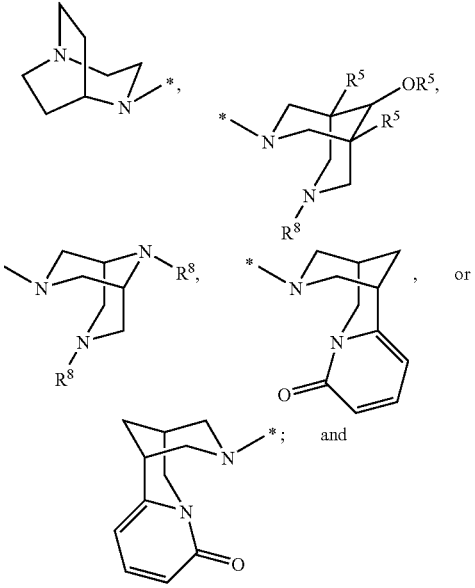

X is methylene, a bond, or absent;
or a pharmaceutically acceptable salt thereof.

3. A compound of claim 1 where $R^1$ is $CONR^6R^7$; $R^6$ is alkyl$SO_2$, cycloalkyl$SO_2$, haloalkyl$SO_2$, $(R^9)(R^{10})NSO_2$, or $(R^{11})SO_2$; and $R^7$ is hydrogen.

4. A compound of claim 1 where $R^2$ is pyridinyl, pyrazinyl, pyrimidinyl, or pyridazinyl, and is substituted with 0-1 substituents selected from the group consisting of $(R^5)_2N$, $R^{12}$, $COR^{13}$, and $SO_2R^{14}$.

5. A compound of claim 1 where $R^3$ is hydrogen.

6. A compound of claim 1 where $R^3$ is methoxy.

7. A compound of claim 1 where $R^4$ is cyclohexyl.

8. A compound of claim 1 where $R^6$ is alkyl$SO_2$, $(R^9)(R^{10})NSO_2$ or $(R^{11})SO_2$.

9. A compound of claim 1 where X is methylene.

10. A compound of claim 1 where X is a bond.

11. A compound of claim 1 where X is absent.

12. A compound selected from the group consisting of
7H-indolo[2,1-a][2]benzazepine-10-carboxylic acid, 13-cyclohexyl-3-methoxy-6-[3-(4-morpholinylcarbonyl)-2-pyridinyl]-, 1,1-dimethylethyl ester;
7H-indolo[2,1-a][2]benzazepine-10-carboxylic acid, 13-cyclohexyl-3-methoxy-6-[3-(4-morpholinylcarbonyl)-2-pyridinyl]-;
7H-indolo[2,1-a][2]benzazepine-10-carboxylic acid, 13-cyclohexyl-3-methoxy-6-[6-(4-morpholinyl)-2-pyridinyl]-;
7H-indolo[2,1-a][2]benzazepine-10-carboxylic acid, 13-cyclohexyl-3-methoxy-6-[6-(4-morpholinyl)-3-pyridazinyl]-;
7H-indolo[2,1-a][2]benzazepine-10-carboxylic acid, 13-cyclohexyl-6-[4-(dimethylamino)-2-pyrimidinyl]-3-methoxy-;
7H-indolo[2,1-a][2]benzazepine-10-carboxylic acid, 13-cyclohexyl-6-[3-(dimethylamino)-2-pyridinyl]-3-methoxy-;
7H-indolo[2,1-a][2]benzazepine-10-carboxylic acid, 13-cyclohexyl-3-methoxy-6-[4-(4-morpholinylcarbonyl)-2-pyridinyl]-;

7H-indolo[2,1-a][2]benzazepine-10-carboxylic acid, 13-cyclohexyl-3-methoxy-6-[3-(4-morpholinylsulfonyl)-2-pyridinyl]-;

7H-indolo[2,1-a][2]benzazepine-10-carboxylic, 13-cyclohexyl-3-methoxy-6-[3-[(3-methyl-3,8-diazabicyclo[3.2.1]oct-8-yl)sulfonyl]-2-pyridinyl]-;

7H-indolo[2,1-a][2]benzazepine-10-carboxylic acid, 13-cyclohexyl-6-[3-(3,3-dimethyl-2-oxo-1-azetidinyl)-2-pyridinyl]-3-methoxy-;

7H-indolo[2,1-a][2]benzazepine-10-carboxylic acid, 13-cyclohexyl-3-methoxy-6-phenyl-;

7H-indolo[2,1-a][2]benzazepine-10-carboxylic acid, 13-cyclohexyl-6-[2-difluoromethoxy)phenyl]-3-methoxy-;

7H-indolo[2,1-a][2]benzazepine-10-carboxylic acid, 13-cyclohexyl-3-methoxy-6-[2-(5-methyl-1,2,4-oxadiazol-3-yl)phenyl]-;

7H-indolo[2,1-a][2]benzazepine-10-carboxylic acid, 13-cyclohexyl-6-[2-[(dimethylamino)sulfonyl]phenyl]-3-methoxy-;

7H-indolo[2,1-a][2]benzazepine-10-carboxylic acid, 13-cyclohexyl-6-[2-[(cyclopropylcarbonyl)amino]phenyl]-3-methoxy-;

7H-indolo[2,1-a][2]benzazepine-10-carboxylic acid, 13-cyclohexyl-3-methoxy-6-[2-[2-(4-morpholinyl)ethoxy]phenyl]-;

7H-indolo[2,1-a][2]benzazepine-10-carboxylic acid, 13-cyclohexyl-6-[2-[2-(dimethylamino)ethoxy]phenyl]-3-methoxy-;

7H-indolo[2,1-a][2]benzazepine-10-carboxylic acid, 13-cyclohexyl-3-methoxy-6-[2-[(methylsulfonyl)methyl]phenyl]-;

7H-indolo[2,1-a][2]benzazepine-10-carboxylic acid, 13-cyclohexyl-6-[3-[2-(dimethylamino)ethoxy]phenyl]-3-methoxy-;

7H-indolo[2,1-a][2]benzazepine-10-carboxylic acid, 13-cyclohexyl-3-methoxy-6-[3-[2-(4-morpholinyl)ethoxy]phenyl]-;

7H-indolo[2,1-a][2]benzazepine-10-carboxylic acid, 13-cyclohexyl-6-[2-[[[2-(dimethylamino)ethyl]methylamino]sulfonyl]phenyl]-3-methoxy-;

7H-indolo[2,1-a][2]benzazepine-10-carboxylic acid, 13-cyclohexyl-3-methoxy-6-[2-(4-morpholinylmethyl)phenyl]-;

7H-indolo[2,1-a][2]benzazepine-10-carboxylic acid, 13-cyclohexyl-3-methoxy-6-[2-(1-pyrrolidinylsulfonyl)phenyl]-;

7H-indolo[2,1-a][2]benzazepine-10-carboxylic acid, 13-cyclohexyl-3-methoxy-6-[2-(1,1,2,2-tetrafluoroethoxy)phenyl]-;

7H-indolo[2,1-a][2]benzazepine-10-carboxylic acid, 13-cyclohexyl-6-(2,3-dihydro-1,4-benzodioxin-5-yl)-3-methoxy-;

7H-indolo[2,1-a][2]benzazepine-10-carboxylic acid, 13-cyclohexyl-6-(2,2-difluoro-1,3-benzodioxol-4-yl)-3-methoxy-;

7H-indolo[2,1-a][2]benzazepine-10-carboxylic acid, 13-cyclohexyl-3-methoxy-6-(7-nitro-1H-indol-5-yl)-;

7H-indolo[2,1-a][2]benzazepine-10-carboxylic acid, 13-cyclohexyl-3-methoxy-6-(7-methoxy-1H-pyrrolo[2,3-c]pyridin-4-yl)-;

7H-indolo[2,1-a][2]benzazepine-10-carboxylic acid, 13-cyclohexyl-3-methoxy-6-(2-methyl-5-benzothiazolyl)-;

7H-indolo[2,1-a][2]benzazepine-10-carboxamide, 13-cyclohexyl-N-[(dimethylamino)sulfonyl]-3-methoxy-6-[3-(4-morpholinylcarbonyl)-2-pyridinyl]-;

or a pharmaceutically acceptable salt thereof.

13. A composition comprising a compound of claim 1, or a pharmaceutically acceptable salt thereof, and a pharmaceutically acceptable carrier.

14. A method of treating hepatitis C infection comprising administering a therapeutically effective amount of a compound of claim 1 to a patient.

15. A compound selected from the group consisting of 7H-indolo[2,1-a][2]benzazepine-10-carboxamide, 13-cyclohexyl-N-[(dimethylamino)sulfonyl]-3-methoxy-6-[6-(4-morpholinyl)-2-pyridinyl]-;

7H-indolo[2,1-a][2]benzazepine-10-carboxamide, 13-cyclohexyl-N-[(dimethylamino)sulfonyl]-3-methoxy-6-[6-(4-morpholinyl)-3-pyridazinyl]-;

7H-indolo[2,1-a][2]benzazepine-10-carboxamide, 13-cyclohexyl-6-[4-(dimethylamino)-2-pyrimidinyl]-N-[(dimethylamino)sulfonyl]-3-methoxy-;

7H-indolo[2,1-a][2]benzazepine-10-carboxamide, 13-cyclohexyl-6-[3-(dimethylamino)-2-pyridinyl]-N-[(dimethylamino)sulfonyl]-3-methoxy-;

7H-indolo[2,1-a][2]benzazepine-10-carboxamide, 13-cyclohexyl-N-[(dimethylamino)sulfonyl]-3-methoxy-6-[4-(4-morpholinylcarbonyl)-2-pyridinyl]-;

7H-indolo[2,1-a][2]benzazepine-10-carboxamide, 13-cyclohexyl-N-[(dimethylamino)sulfonyl]-3-methoxy-6-[3-(4-morpholinylsulfonyl)-2-pyridinyl]-;

7H-indolo[2,1-a][2]benzazepine-10-carboxamide, 13-cyclohexyl-N-[(dimethylamino)sulfonyl]-3-methoxy-6-[3-[(3-methyl-3,8-diazabicyclo[3.2.1]oct-8-yl)sulfonyl]-2-pyridinyl]-;

7H-indolo[2,1-a][2]benzazepine-10-carboxamide, 13-cyclohexyl-N-[(dimethylamino)sulfonyl]-6-[3-(3,3-dimethyl-2-oxo-1-azetidinyl)-2-pyridinyl]-3-methoxy-;

7H-indolo[2,1-a][2]benzazepine-10-carboxamide, 13-cyclohexyl-3-methoxy-N-[(1-methylethyl)sulfonyl]-6-[2-(5-methyl-1,2,4-oxadiazol-3-yl)phenyl]-;

7H-indolo[2,1-a][2]benzazepine-10-carboxamide, 13-cyclohexyl-6-[2-(difluoromethoxy)phenyl]-3-methoxy-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-phenyl-;

7H-indolo[2,1-a][2]benzazepine-10-carboxamide, 13-cyclohexyl-6-[2-[(dimethylamino)sulfonyl]phenyl]-3-methoxy-N-[(1-methylethyl)sulfonyl]-;

7H-indolo[2,1-a][2]benzazepine-10-carboxamide, 13-cyclohexyl-6-[2-[(cyclopropylcarbonyl)amino]phenyl]-3-methoxy-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[2-[2-(4-morpholinyl)ethoxy]phenyl]-;

7H-indolo[2,1-a][2]benzazepine-10-carboxamide, 13-cyclohexyl-6-[2-[2-(dimethylamino)ethoxy]phenyl]-3-methoxy-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[2-[(methylsulfonyl)methyl]phenyl]-;

7H-indolo[2,1-a][2]benzazepine-10-carboxamide, 13-cyclohexyl-6-[3-[2-(dimethylamino)ethoxy]phenyl]-3-methoxy-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[3-[2-(4-morpholinyl)ethoxy]phenyl]-; 7H-indolo[2,1-a][2]benzazepine-10-carboxamide, 13-cyclohexyl-6-[2-[[[2-(dimethylamino)ethyl]methylamino]sulfonyl]phenyl]-3-methoxy-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[2-(4-morpholinylmethyl)phenyl]-;

7H-indolo[2,1-a][2]benzazepine-10-carboxamide, 13-cyclohexyl-3-methoxy-N-[(1-methylethyl)sulfonyl]-6-[2-(1-pyrrolidinylsulfonyl)phenyl]-;

7H-indolo[2,1-a][2]benzazepine-10-carboxamide, 13-cyclohexyl-3-methoxy-N-[(1-methylethyl)sulfonyl]-6-[2-(1,1,2,2-tetrafluoroethoxy)phenyl]-;

7H-indolo[2,1-a][2]benzazepine-10-carboxamide, 13-cyclohexyl-6-(2,3-dihydro-1,4-benzodioxin-5-yl)-3-methoxy-N-[(1-methylethyl)sulfonyl]-;

5H-indolo[2,1-a][2]benzazepine-10-carboxamide, 13-cyclohexyl-N-[(dimethylamino)sulfonyl]-6,7-dihydro-3-methoxy-6-[3-(4-morpholinylcarbonyl)-2-pyridinyl]-;

5H-indolo[2,1-a][2]benzazepine-10-carboxamide, 13-cyclohexyl-N-[(dimethylamino)sulfonyl]-6,7-dihydro-3-methoxy-6-[6-(4-morpholinyl)-2-pyridinyl]-;

5H-indolo[2,1-a][2]benzazepine-10-carboxamide, 13-cyclohexyl-N-[(dimethylamino)sulfonyl]-6,7-dihydro-3-methoxy-6-[4-(4-morpholinylcarbonyl)-2-pyridinyl]-; and 5H-indolo[2,1-a][2]benzazepine-10-carboxamide, 13-cyclohexyl-6-[3-[2-(dimethylamino)ethoxy]phenyl]-6,7-dihydro-3-methoxy-N-[(1-methylethyl)sulfonyl]-;

or a pharmaceutically acceptable salt thereof.

16. A compound selected from the group consisting of 5H-indolo[2,1-a][2]benzazepine-10-carboxamide, 13-cyclohexyl-6,7-dihydro-3-methoxy-N-[(1-methylethyl)sulfonyl]-6-[3-[2-(4-morpholinyl)ethoxy]phenyl]-;

7H-indolo[2,1-a][2]benzazepine-10-carboxylic acid, 13-cyclohexyl-3-methoxy-6-[3-[(4-methyl -1-piperazinyl)carbonyl]-2-pyridinyl]-, 1,1-dimethylethyl ester;

7H-indolo[2,1-a][2]benzazepine-10-carboxylic acid, 13-cyclohexyl-3-methoxy-6-[3-[(4-methyl -1-piperazinyl)carbonyl]-2-pyridinyl]-;

7H-indolo[2,1-a][2]benzazepine-10-carboxylic acid, 13-cyclohexyl-6-[3-[(dimethylamino)carbonyl]-2-pyridinyl]-3-methoxy-;

7H-indolo[2,1-a][2]benzazepine-10-carboxylic acid, 13-cyclohexyl-3-methoxy-6-[3-(1-pyrrolidinylcarbonyl)-2-pyridinyl]-;

7H-indolo[2,1-a][2]benzazepine-10-carboxylic acid, 13-cyclohexyl-3-methoxy-6-[3-[(3-methyl -3,8-diazabicyclo[3.2.1 ]oct-8-yl)carbonyl]-2-pyridinyl]-;

7H-indolo[2,1-a][2]benzazepine-10-carboxylic acid, 13-cyclohexyl-6-[3-[(4-hydroxy-1-piperidinyl)carbonyl]-2-pyridinyl]-3-methoxy-;

7H-indolo[2,1-a][2]benzazepine-10-carboxylic acid, 13-cyclohexyl-3-methoxy-6-[3-(1-piperidinylcarbonyl)-2-pyridinyl]-;

7H-indolo[2,1-a][2]benzazepine-10-carboxamide, 13-cyclohexyl-N-[(dimethylamino)sulfonyl]-3-methoxy-6-[3-[(4-methyl-1-piperazinyl)carbonyl]-2-pyridinyl]-;

7H-indolo[2,1-a][2]benzazepine-10-carboxamide, 13-cyclohexyl-6-[3-[(dimethylamino)carbonyl]-2-pyridinyl]-N-[(dimethylamino)sulfonyl]-3-methoxy-;

7H-indolo[2,1-a][2]benzazepine-10-carboxamide, 13-cyclohexyl-N-[(dimethylamino)sulfonyl]-3-methoxy-6-[3-(1-pyrrolidinylcarbonyl)-2-pyridinyl]-;

7H-indolo[2,1-a][2]benzazepine-10-carboxamide, 13-cyclohexyl-N-[(dimethylamino)sulfonyl]-3-methoxy-6-[3-[(3-methyl-3,8-diazabicyclo[3.2.1 ]oct-8-yl)carbonyl]-2-pyridinyl]-;

7H-indolo[2,1-a][2]benzazepine-10-carboxamide, 13-cyclohexyl-N-[(dimethylamino)sulfonyl]-6-[3-[(4-hydroxy-1-piperidinyl)carbonyl]-2-pyridinyl]-3-methoxy-;

7H-indolo[2,1-a][2]benzazepine-10-carboxamide, 13-cyclohexyl-N-[(dimethylamino)sulfonyl]-3-methoxy-6-[3-(1-piperidinylcarbonyl)-2-pyridinyl]-;

Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[3-[(4-methyl-1-piperazinyl)carbonyl]-2-pyridinyl]-;

7H-indolo[2,1-a][2]benzazepine-10-carboxylic acid, 13-cyclohexyl-3-methoxy-6-[2-[(3-methyl -3,8-diazabicyclo[3.2.1 ]oct-8-yl)carbonyl]phenyl]-, 1,1-dimethylethyl ester;

7H-indolo[2,1-a][2]benzazepine-10-carboxylic acid, 13-cyclohexyl-3-methoxy-6-[2-[(3-methyl -3,8-diazabicyclo[3.2.1 ]oct-8-yl)carbonyl]phenyl]-;

13-cyclohexyl-N-(isopropylsulfonyl)-3-methoxy-6-(2-((3-methyl-3,8-diazabicyclo[3.2.1 ]oct-8-yl)carbonyl)phenyl)-7H-indolo[2,1-a][2]benzazepine-10-carboxamide; and 7H-indolo[2,1-a][2]benzazepine-10-carboxylic acid, 13-cyclohexyl-3-methoxy-6-[2-(4-morpholinylcarbonyl)phenyl]-, 1,1-dimethylethyl ester;

or a pharmaceutically acceptable salt thereof.

* * * * *

UNITED STATES PATENT AND TRADEMARK OFFICE
CERTIFICATE OF CORRECTION

PATENT NO.        : 7,642,251 B2
APPLICATION NO.   : 12/184791
DATED             : January 5, 2010
INVENTOR(S)       : Carl P. Bergstrom et al.

It is certified that error appears in the above-identified patent and that said Letters Patent is hereby corrected as shown below:

In the Claims:

Claim 2:

Column 108, line 15, change "pyradazinyl" to -- pyridazinyl --.

Claim 12:

Column 111, line 13, change "difluoromethoxy)" to -- (difluoromethoxy) --.

Claim 15:

Column 112, lines 64 to 67, after "phenyl]-;", move "7H-indolo[2,1-a][2]benzazepine-10-carboxamide, 13-cyclohexyl-6-[2-[[[2-(dimethylamino)ethyl]methylamino]sulfonyl]phenyl]-3-methoxy-N-[(1-methylethyl)sulfonyl]-;" to next line as a separate paragraph.

Signed and Sealed this
Eighth Day of November, 2011

David J. Kappos
*Director of the United States Patent and Trademark Office*